United States Patent
Chen et al.

(10) Patent No.: US 12,065,672 B2
(45) Date of Patent: Aug. 20, 2024

(54) METHODS FOR THE PRODUCTION OF THERAPEUTIC, DIAGNOSTIC, OR RESEARCH ANTIBODIES

(71) Applicant: Wayne State University, Detroit, MI (US)

(72) Inventors: Kang Chen, Detroit, MI (US); Bo Pei, San Diego, CA (US)

(73) Assignee: Wayne State University, Detroit, MI (US)

( * ) Notice: Subject to any disclaimer, the term of this patent is extended or adjusted under 35 U.S.C. 154(b) by 370 days.

(21) Appl. No.: 17/224,047

(22) Filed: Apr. 6, 2021

(65) Prior Publication Data

US 2021/0317405 A1 Oct. 14, 2021

Related U.S. Application Data

(63) Continuation of application No. 16/118,090, filed on Aug. 30, 2018, now Pat. No. 11,001,804.

(60) Provisional application No. 62/552,292, filed on Aug. 30, 2017.

(51) Int. Cl.

| C12N 5/0781 | (2010.01) |
| C07K 14/47 | (2006.01) |
| C07K 14/495 | (2006.01) |
| C07K 14/54 | (2006.01) |
| C07K 14/57 | (2006.01) |
| C07K 14/705 | (2006.01) |
| C07K 16/06 | (2006.01) |
| C12N 15/62 | (2006.01) |

(52) U.S. Cl.
CPC ........ *C12N 5/0635* (2013.01); *C07K 14/4702* (2013.01); *C07K 14/495* (2013.01); *C07K 14/5406* (2013.01); *C07K 14/57* (2013.01); *C07K 14/70578* (2013.01); *C07K 16/06* (2013.01); *C07K 16/065* (2013.01); *C12N 15/62* (2013.01); *C07K 2317/565* (2013.01); *C07K 2319/21* (2013.01); *C07K 2319/41* (2013.01); *C07K 2319/43* (2013.01); *C12N 2310/20* (2017.05)

(58) Field of Classification Search
None
See application file for complete search history.

(56) References Cited

U.S. PATENT DOCUMENTS

2019/0062705 A1 2/2019 Chen et al.

FOREIGN PATENT DOCUMENTS

WO WO2011029126 A1 3/2011

OTHER PUBLICATIONS

Akiyama, et al., "The Tumor Necrosis Factor Family Receptors RANK and CD40 Cooperatively Establish the Thymic Medullary Microenvironment and Self-Tolerance," Immunity, vol. 29, No. 3, 2008, pp. 423-437.
Anderson, et al., "Projection of an Immunological Self Shadow Within the Thymus by the Aire Protein," Science, vol. 298, No. 5597, 2002, pp. 1395-1401.
Casellas, et al., "Mutations, Kataegis and Translocations in B Cells: Understanding AID Promiscuous Activity," Nat. Rev. Immunol., vol. 16, No. 3, 2016, pp. 164-176.
Chen, et al., "Immunoglobulin D Enhances Immune Surveillance by Activating Antimicrobial, Proinflammatory and B Cell-Stimulating Programs in Basophils," Nat. Immunol., vol. 10, No. 8, 2009, pp. 889-898.
Durandy, et al., "Hyper-Immunoglobulin M Syndromes Caused by Intrinsic B-Lymphocyte Defects," Immunol. Rev., vol. 203, No. 1, 2005, pp. 67-79.
Finnish-German APECED Consortium, "An Autoimmune Disease, APECED, Caused by Mutations in a Novel Gene Featuring Two PHD-Type Zinc-Finger Domains," Nat. Genet., vol. 17, No. 4, 1997, pp. 399-403.
Gardner, et al., "Deletional Tolerance Mediated by Extrathymic Aire-Expressing Cells," Science, vol. 321, No. 5890, 2008, pp. 843-847.
Kisand, et al., "Chronic Mucocutaneous Candidiasis in APECED or Thymoma Patients Correlates with Autoimmunity to Th17-Associated Cytokines," J. Exp. Med., vol. 207, No. 2, 2010, pp. 299-308.
Liu, et al., "Mechanism of Antigen-Driven Selection in Germinal Centres," Nature, vol. 342, No. 6252, 1989, pp. 929-931.
Malchow, et al., "Aire-Dependent Thymic Development of Tumor-Associated Regulatory T Cells," Science, vol. 339, No. 6124, 2013, pp. 1219-1224.
Maul, et al., "Uracil Residues Dependent on the Deaminase AID in Immunoglobulin Gene Variable and Switch Regions," Nat. Immunol., vol. 12, No. 1, 2011, pp. 70-76.
Meyer, et al., "AIRE-Deficient Patients Harbor Unique High-Affinity Disease-Ameliorating Autoantibodies," Cell., vol. 166, No. 3, 2016, pp. 582-595.
Muramatsu, et al., "Class Switch Recombination and Hypermutation Require Activation-Induced Cytidine Deaminase (AID), a Potential RNA Editing Enzyme," Cell, vol. 102, No. 5, 2000, pp. 553-563.
Nagamine, et al., "Positional Cloning of the APECED Gene," Nat. Genet., vol. 17, No. 4, 1997, pp. 393-398.
Non Final Office Action for U.S. Appl. No. 16/118,090, filed Jul. 13, 2020, "Methods for the Production of Therapeutic, Diagnostic, or Research Antibodies" 9 pages.

(Continued)

*Primary Examiner* — Daniel C Gamett
(74) *Attorney, Agent, or Firm* — Lee & Hayes P.C.

(57) ABSTRACT

Down-regulating autoimmune regulator (AIRE) function in B cells to produce antibodies is described. The antibodies can be class-switched, high affinity, and neutralizing, and have a high degree of somatic hypermutations, even in the framework region, as compared to antibodies produced in the absence of AIRE downregulation.

6 Claims, 65 Drawing Sheets

Specification includes a Sequence Listing.

(56) References Cited

OTHER PUBLICATIONS

Oven, et al., "AIRE Recruits P-TEFb for Transcriptional Elongation of Target Genes in Medullary Thymic Epithelial Cells," Mol. Cell. Biol., vol. 27, No. 24, 2007, pp. 8815-8823.
Patenaude, et al., "Active Nuclear Import and Cytoplasmic Retention of Activation-Induced Deaminase," Nat. Struct. Mol. Biol., vol. 16, No. 5, 2009, pp. 517-527.
Pavri, et al., "Activation-Induced Cytidine Deaminase Targets DNA at Sites of RNA Polymerase II Stalling by Interaction With Spt5," Cell., vol. 143, No. 1, 2010, pp. 122-133.
Peterlin & Price, "Controlling the Elongation Phase of Transcription With P-TEFb," Mol. Cell., vol. 23, No. 3, 2006, pp. 297-305.
Puel, et al., "Autoantibodies Against IL-17A, IL-17F, and IL-22 in Patients With Chronic Mucocutaneous Candidiasis and Autoimmune Polyendocrine Syndrome Type I," J. Exp. Med., vol. 207, No. 2, 2010, pp. 291-297.
Revy, et al., "Activation-Induced Cytidine Deaminase (AID) Deficiency Causes the Autosomal Recessive Form of the Hyper-IgM Syndrome (HIGM2)," Cell., vol. 102, No. 5, 2000, pp. 565-575.
Rosenspire & Chen, "Anergic B Cells: Precarious On-Call Warriors at the Nexus of Autoimmunity and False-Flagged Pathogens," Front. Immunol., vol. 6, No. 580, 2015, pp. 1-5.
Sale & Neuberger, "TdT-Accessible Breaks are Scattered Over the Immunoglobulin V Domain in a Constitutively Hypermutating B Cell Line," Immunity, vol. 9, No. 6, 1998, pp. 859-869.
Schroeder, et al., "Breaching Peripheral Tolerance Promotes the Production of HIV-1-Neutralizing Antibodies," J. Exp. Med., vol. 214, No. 8, 2017, pp. 2283-2302.
Trager, et al., "The Immune Response to Melanoma Is Limited by Thymic Selection of Self-Antigens," PLoS One, vol. 7, No. 4, 2012, 12 pages.
Vinuesa, et al., "Dysregulation of Germinal Centres in Autoimmune Disease," Nat. Rev. Immunol., vol. 9, No. 12, 2009, pp. 845-857.
Vuong, et al., "Specific Recruitment of Protein Kinase A to the Immunoglobulin Locus Regulates Class-Switch Recombination," Nat. Immunol., vol. 10, No. 4, 2009, pp. 420-426.
Wei, et al., "Mice Carrying a Knock-In Mutation of Aicda Resulting in a Defect in Somatic Hypermutation Have Impaired Gut Homeostasis and Compromised Mucosal Defense," Nat. Immunol., vol. 12, No. 3, 2011, pp. 264-270.
Yamano, et al., "Thymic B Cells Are Licensed to Present Self Antigens for Central T Cell Tolerance Induction," Immunity, vol. 42, No. 6, 2015, pp. 1048-1061.
Yeh, et al., "A Pathway for Tumor Necrosis Factor-Alpha-Induced Bcl10 Nuclear Translocation. Bcl10 is Up-Regulated by NF-kappaB and Phosphorylated by Akt1 and Then Complexes With Bcl3 to Enter the Nucleus," J. Biol. Chem., vol. 281, No. 1, 2006, pp. 167-175.
Zhou, et al., "A Germinal Center Checkpoint of AIRE in B Cells Limits Antibody Diversification," bioRxiv, 2024, 93 pages.

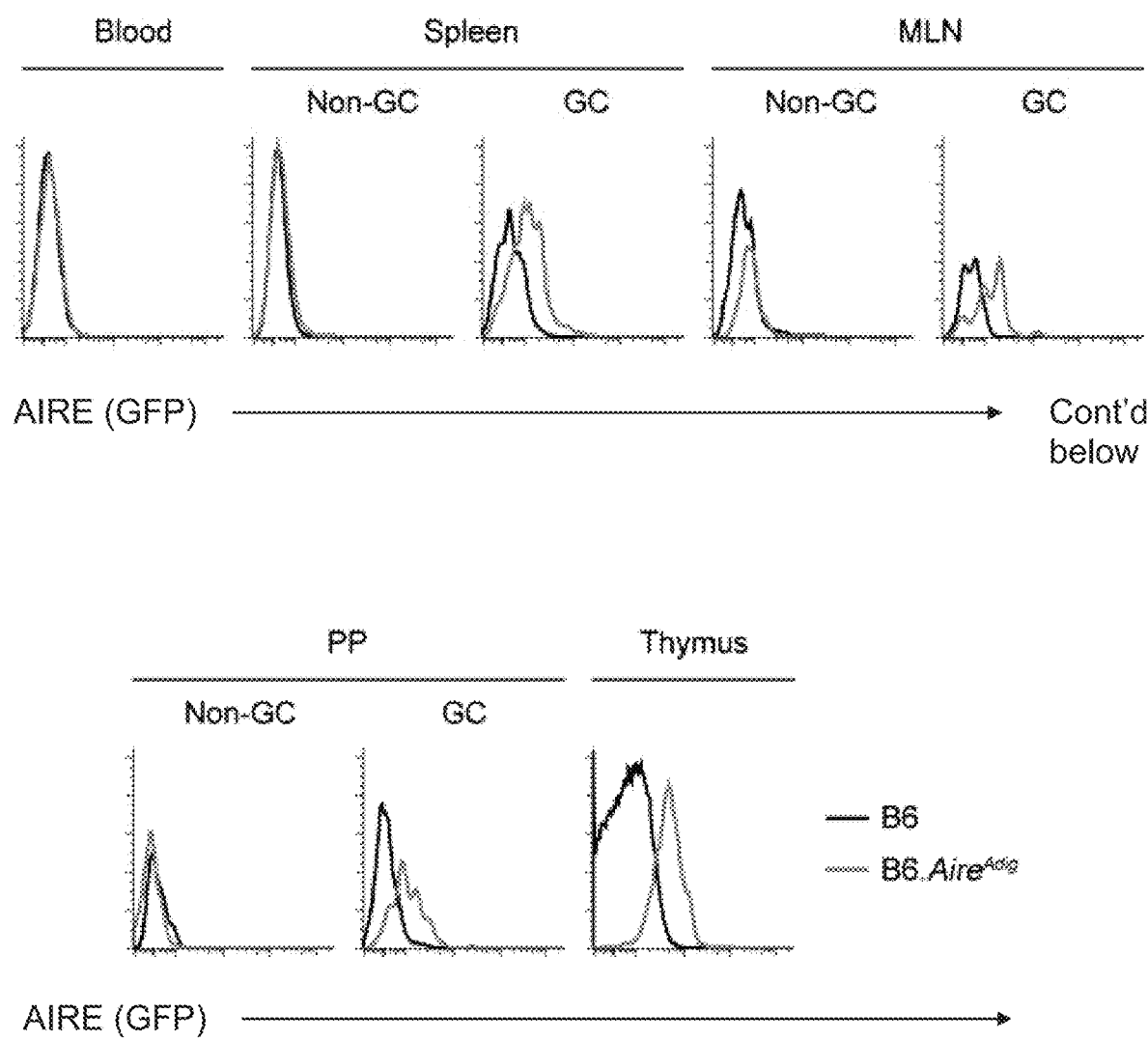

FIG. 3C
HIGM3 tonsil
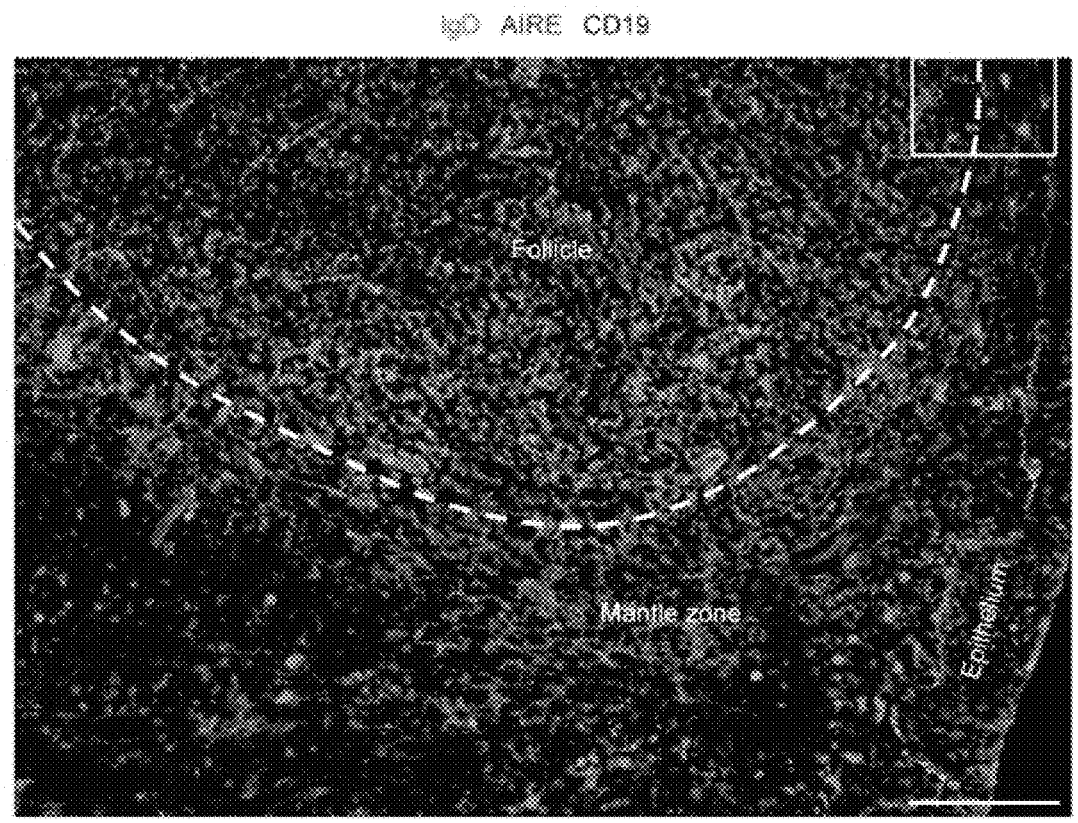
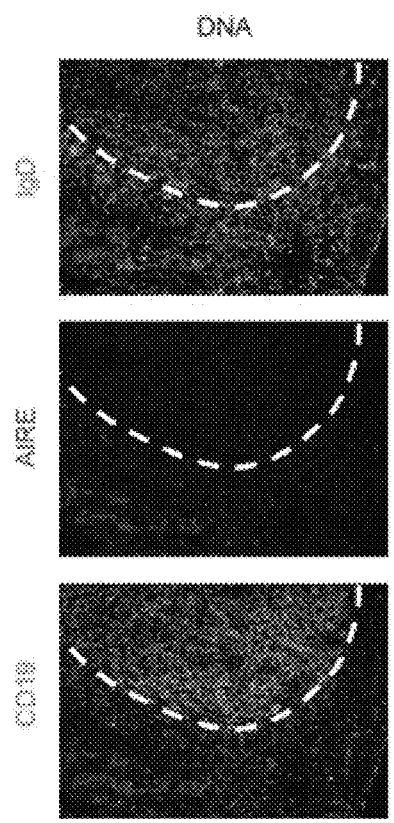

FIG. 7A (cont'd)

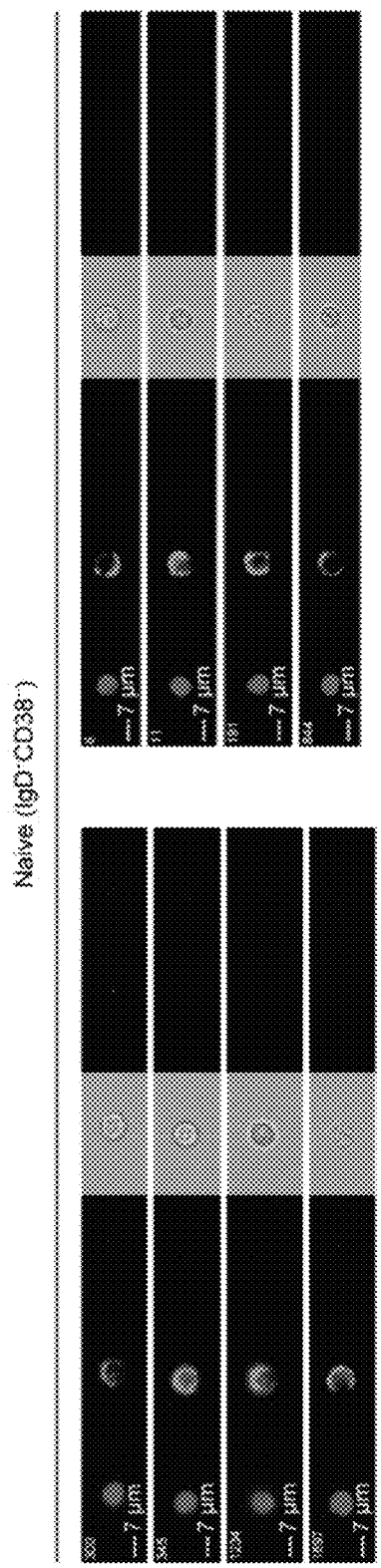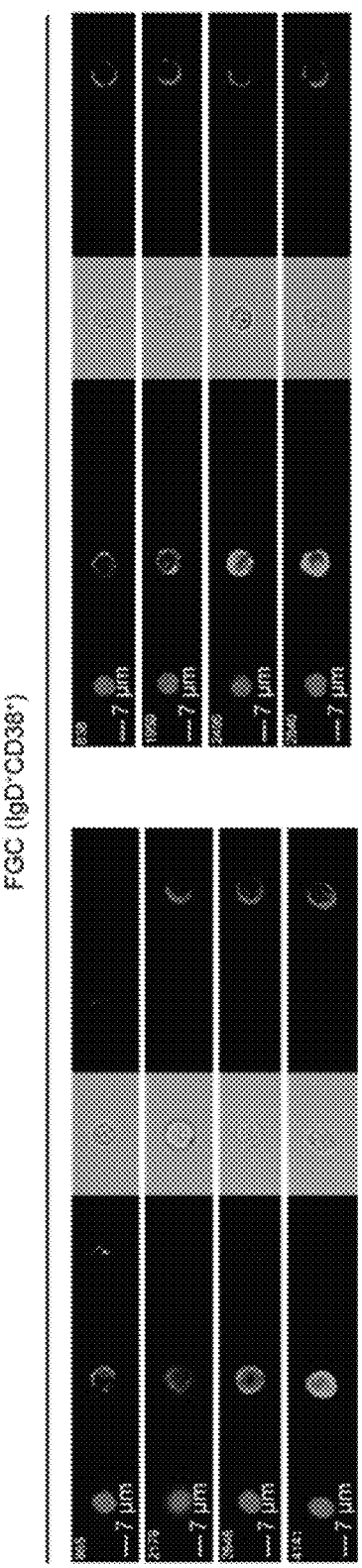
FIG. 10C
FIG. 10D

FIG. 12A a. Primers for cloning human AIRE constructs into pcDNA3.1(-)/Myc-His

| Name | Description | Remaining region | MW with tag (kDa) | Primer name and sequence (5'-3') |
|---|---|---|---|---|
| WT | Full length | 1-545 | 60.7 | — |
| M1 | ΔPHD2 | 1-430 | 48.8 | D430_R AGGAGCCAAGGTTCTGCTGACC<br>Hind-Myc_F GAAAGCTTTCTAGAACAAAAACTCATCTCA |
| M2 | ΔPHD1, PHD2 | 1-298 | 35 | D298_R CTCGTCCTCATTCTTCTGGTGGAG<br>Hind-Myc_F GAAAGCTTTCTAGAACAAAAACTCATCTCA |
| M3 | ΔSAND, PHD1, PHD2 | 1-181 | 23 | D181_R AATCCCGTTCCCGAGTGGAAG<br>Hind-Myc_F GAAAGCTTTCTAGAACAAAAACTCATCTCA |
| M4 | ΔCARD | 101-545 | 49 | EcoRV-ATG_R CATGGTGAATTCTGCAGATATCCAGC<br>D101_F CCCAAAGATGTGGACCTCAGCC |
| M5 | ΔCARD, ΔNLS | 181-545 | 41 | EcoRV-ATG_R CATGGTGAATTCTGCAGATATCCAGC<br>D181_F ATTCAGACCATGTCAGCTTCAGTCCA |
| M6 | ΔNLS | 1-100, 181-545 | 52.5 | D100_R GAAGCTGTCGACCAGGATGGGCTG<br>D181_F ATTCAGACCATGTCAGCTTCAGTCCA |
| M7 | NLS only | 101-181 | 12 | D181_R AATCCCGTTCCCGAGTGGAAG<br>Hind-Myc_F GAAAGCTTTCTAGAACAAAAACTCATCTCA |

FIG. 12B b, Primers for cloning human AID constructs into pFLAG-CMV2

| Name | Description | Remaining region | MW with tag (kDa) | Primer name and sequence (5'-3') |
|---|---|---|---|---|
| WT | Full length | 1-198 | 26.3 | AID_F ATGGACAGCCTCTTGATGAACCG<br>AID_R AAGTCCCAAAGTACGAAATGCGTC |
| M1 | E58A | 1-198 | 26.3 | AID_F ATGGACAGCCTCTTGATGAACCG<br>AID_R AAGTCCCAAAGTACGAAATGCGTC |
| M2 | NLS of AID replaced with NLS of nucleoplasmin | 1-198 | 26.3 | npNLS_top<br>AAAAGGCCGGCGGCCACGAAAAAGGCCGGCCAGGCAAAAAGAAAAAG<br>npNLS_bottom<br>CTTTTTCTTTTTGCCTGGCCGGCCTTTTTCGTGGCCGCCGGCCTTTT<br>(npNLS_top and npNLS_bottom were annealed together before ligation with the PCR product of the primer pair AID8-R and AID27-F.) |
| M3 | ΔCatalytic domain | 1-54, 95-198 | 21.4 | AID54_R GCCGTTCTTATTGCGAAGATAACCA<br>AID95_F GCCGACTTTCTGCGAGGGA |
| M4 | ΔAPOBEC-like and ΔNES domains | 1-94 | 13.8 | AID94_R CACATGTCGGGCACAGTCGTAG<br>TAG_F TAGACTGAAACTTTTTGGGGGAGGG |
| M5 | ΔNLS | 1-8; 27-198 | 24 | AID8_R CCGGTTCATCAAGAGCTGTCC<br>AID27_F ACCTACCTGTCTACGTAGTGAAGAGGC |
| M6 | G23S | 1-198 | 26.3 | AID22_R CTTAGCCCAGCGGACATTTTGA<br>AID23_F AGTCGGCGTGAAGACCTACCTGTG |

FIG. 12C

| Description | Primer name and sequence (5'-3') |
|---|---|
| c. Cloning primers for generating pCMV-Tag1-mAIRE-GFP plasmids | |
| Full length AIRE | - |
| AIREΔNLS | D106_R GTCCACATCTTTTGGGAAGCCG<br>D182_F ATTCAGAGACCATGGCCAGCTTCTGTC |
| Full length eGFP | GFP_F ATGGTGAGCAAGGGCGAGGAG<br>GFP_R CTTGTACAGCTCGTCCATGCCG |
| AIRE of AIREΔNLS in pCMV-Tag1 vector | TGA-Sal1_F TGATGACAGGTCGACCTCGAGC<br>AIRE_R GGAAGAGAAGGGTGGTGTCTCGG |

FIG. 16A

| Target | Primer name and sequence (5'–3') | |
|---|---|---|
| | Forward | Reverse |
| a. Human genes | | |
| AIRE primer pair 1 | GATGACCTGGAGTCCCTTCT | CTCATCAGAGCTGCATGTCC |
| AIRE primer pair 2 | CCAGAAGAATGAGGAGGAG | AGCCGTCACAGCAGATGAG |
| ACTB | AGAGCTACGAGCTGCCTGAC | AGCACTGTGTTGGCGTACAG |
| Iμ-Cγ1 | Iμ GTGATTAAGGAGAAACACTTTGAT | Cγ1_R CCAGGGGCTGCTGTGCCCCA |
| Iμ-Cγ3 | | Cγ3_R CCAGGGGCGCTGTGCCCCA |

FIG. 16B

| b. Mouse genes | | |
|---|---|---|
| Actb | TGCGTGACATCAAAGAGAAG | CGGATGTCAACGTCACACTT |
| Aicda | GAAAGTCACGCTGGAG | TCTCATGCCGTCCCTT |
| Iα-Cμ circle transcript | Iα CCAGGCATGGTTGAGATAGAGATAG | Cμ AATGGTGCTGGGCAGGAAGT |
| Iγ1-Cμ circle transcript | Iγ1 GGCCCTTCCAGATCTTTGAG | |
| Iμ-Cμ germline transcript | Iμ CTCTGGCCCTGCTTATTGTTG | Cμ' GAGACATTTGGAAGGACTGACT |
| Iα-Cα germline transcript | Iα CCTGSCTGTCCCCTATGAA | Cα GAGCTGGTGGGAGTGTCAGTG |
| Sμ (after ChIP) | Sμ_F TAGTAAGCGAGGCTCAAAAAGCAT | Sμ_R AGAACAGTCCAGTGTAGGCAGTAGA |
| Iμ (after ChIP) | Iμ_F GCTCAGGCTGGACTTTCGGTTGGT | Iμ_R GGAGTCAAGATGGCGATCAGAACC |
| Sγ1 (after ChIP) | Sγ1_F TATGATGGAAAGAGGGTAGCATTCACC | Sγ1_R CTCCTTCCCAATCTCCGTG |

FIG. 17A

| Antigen | Conjugation | Isotype | Clone | Manufacturer | Use |
|---|---|---|---|---|---|
| a. Antibodies to human antigens | | | | | |
| AID | — | Rat IgG2a | mAID-2 | eBioscience 14-5959 | WB |
| | — | Rabbit IgG | — | See ref 17 | IP |
| | AF647 | Rat IgG2b | EK2-5G9 | BD 565785 | FC |
| AIRE | — | Mouse IgG1 | C-2 | Santa Cruz sc-373703 | WB |
| | APC | Recombinant Human IgG | REA352 | Miltenyi Biotec 130-105-401 | IF |
| | eF570 | Rat IgG2a | TM-724 | eBioscience 41-9534 | FC |
| | PE | Recombinant Human IgG | REA352 | Miltenyi Biotec 130-105-359 | FC |
| Bcl10 | — | Mouse IgG1 | 331.3 | Santa Cruz sc-5273 | IP |
| CD19 | Biotin | Mouse IgG1 | HIB19 | Biolegend 302204 | MACS, IF |
| | eF450 | Mouse IgG1 | HIB19 | Tonbo 75-0199-T100 | FC |
| | PE | Mouse IgG1 | 4G7 | BD 349209 | FC, IF |
| | PE | Mouse IgG1 | HIB19 | BD 555413 | FC, IF |
| | PE-CF594 | Mouse IgG1 | HIB19 | BD 562321 | FC |
| | PE-Cy7 | Mouse IgG1 | HIB19 | eBioscience 25-0199 | FC |
| | QDot655 | Mouse IgG1 | SJ25C1 | Thermo Fisher Scientific Q10179 | FC |
| | BV786 | Mouse IgG1 | SJ25C1 | BD 563326 | FC |
| CD24 | APC-eF780 | Mouse IgG1 | eBioSN3 | eBioscience 47-0247 | FC |
| CD27 | AF647 | Mouse IgG1 | O323 | Biolegend 302812 | FC |
| CD38 | APC | Mouse IgG1 | HIT2 | Biolegend 303510 | FC |

FIG. 17A (cont'd)

| Antigen | Conjugation | Isotype | Clone | Manufacturer | Use |
|---|---|---|---|---|---|
| | PE-Cy7 | Mouse IgG1 | HIT2 | Biolegend 303510 | FC |
| CD45 | eF450 | Mouse IgG1 | 2D1 | eBioscience 48-9459 | FC |
| | PE-Cy7 | Mouse IgG1 | HI30 | Tonbo 60-0459 | FC |
| EpCAM | AF488 | Mouse IgG2b | 9C4 | Biolegend 324210 | IF |
| Erk1/2 | – | Mouse IgG1 | L34F12 | Cell Signalling 4696 | WB |
| p-Erk1/2 | – | Rabbit IgG | D13.14.4E | Cell Signalling 4370 | WB |
| Hsp90 | – | Rabbit IgG | C45G5 | Cell Signalling 4877 | WB |
| | Biotin | Goat IgG F(ab)2 | – | Southern Biotech 2032-08 | MACS |
| IgD | FITC | Goat IgG F(ab)2 | – | Southern Biotech 2032-02 | FC, IF |
| | FITC | Mouse IgG2a | IA6-2 | BD 555778 | FC |
| Lamin B1 | – | Rabbit IgG | – | Santa Cruz sc-20682 (H-90) | WB |
| NF-κB p65 | – | Mouse IgG1 | F6 | Santa Cruz sc-8008 | WB |
| NF-κB p65 Ser536 | – | Rabbit IgG | 1091B | R&D MAB72261 | WB |
| β-Actin | – | Mouse IgG1 | AC-15 | Sigma-Aldrich A5441 | WB |

FIG. 17B

| Antigen | Conjugation | Isotype | Clone | Manufacturer | Use |
|---|---|---|---|---|---|
| b. Antibodies to mouse antigens | | | | | |
| AID | — | Rat IgG2a | mAID-2 | eBioscience 14-5959 | WB |
| | — | Rabbit IgG | — | See ref [17] | IP, ChIP |
| | — | Rabbit IgG | — | Santa Cruz sc-33188 (H-300) | WB |
| | — | Goat IgG | — | Santa Cruz sc-17986 (O-17) | IP |
| AIRE | eF660 | Rat IgG2c | 5H12 | eBioscience 14-5934 | WB |
| | — | Rat IgG2c | 5H12 | eBioscience 50-5934 | IF |
| | APC | Recombinant Human IgG | REA352 | Miltenyi Biotec 130-105-401 | IF (can stain mouse AIRE) |
| B220 | APC-Cy7 | Rat IgG2a | RA3-6B2 | Biolegend 103224 | FC |
| BAFF-R | APC | Rat IgG1 | eBio7H22-E16 | eBioscience 17-5943 | FC |
| CD138 | Biotin | Rat IgG2a | 281-2 | Biolegend 142514 | FC |
| | PE-Cy7 | Rat IgG2a | 281-2 | Biolegend 142511 | FC |
| CD16/CD32 | — | Rat IgG2b | 2.4G2 | Tonbo 70-0161, BD 553141 | Fc Block |
| | Biotin | Rat IgG2a | 1D3 | BD 553784 | FC, IF |
| | BV650 | Rat IgG2a | 6D5 | Biolegend 115541 | FC |
| CD19 | FITC | Rat IgG2a | 1D3 | Tonbo 35-0193 | FC |
| | Pacific Blue | Rat IgG2a | 6D5 | Biolegend 115523 | FC |
| | PE-CF594 | Rat IgG2a | 1D3 | BD 562291 | FC |
| CD21 | APC | Rat IgG2b | 7G6 | BD 558658 | FC |
| CD23 | PE | Rat IgG2a | B3B4 | BD 553139 | FC |
| CD25 | APC | Rat IgG1 | PC61.5 | Tonbo 20-0251 | FC |

FIG. 17B (cont'd)

| | | | | | |
|---|---|---|---|---|---|
| CD3 | APC-Cy7 | Rat IgG2b | 17A2 | Tonbo 25-0032 | FC |
| CD38 | PE-Cy7 | Rat IgG2a | 90 | Biolegend 102717 | FC |
| | - | Rat IgG2b | GK1.5 | Biolegend 100401 | IHC, IF |
| | FITC | Rat IgG2b | GK1.5 | Biolegend 100406, BD 553729 | FC |
| CD4 | PE | Rat IgG2b | GK1.5 | Biolegend 100408 | FC |
| | PerCP-Cy5.5 | Rat IgG2b | GK1.5 | Biolegend 100434 | FC |
| CD40 | - | Hamster IgM | HM40-3 | eBioscience 16-0402 | Stim |
| | FITC | Hamster IgM | HM40-3 | BD 553723 | FC |
| CD45 | violetFluor450 | Rat IgG2b | 30-F11 | Tonbo 75-0451 | FC |
| CD62L | PE-Cy7 | Rat IgG2a | MEL-14 | BD 560516 | FC |
| CD80 | PerCP-Cy5.5 | Hamster IgG2 | 16-10A1 | BD 560526 | FC |
| CD83 | BV650 | Rat IgG1 | Michel-19 | Biolegend 121515 | FC |
| CD86 | APC | Rat IgG2a | GL-1 | BD 558703 | FC |
| CD93 | PE | Rat IgG2b | AA4.1 | Biolegend 136503 | FC |
| CXCR4 | Biotin | Rat IgG2b | 2B11 | eBioscience 13-9991 | FC |
| CXCR5 | PE | Rat IgG2b | L138D7 | Biolegend 145504 | FC |
| FAS | PE | Hamster IgG2 | Jo2 | BD 554258 | FC |
| Foxp3 | V450 | Rat IgG2b | MF23 | BD 561293 | FC |
| GAPDH | - | Rabbit IgG | 14C10 | Cell Signalling 2188 | WB |
| GL7 | AP647 | Rat IgM | GL7 | BD 561529 | FC |
| Hsp90 | - | Rabbit IgG | C45G5 | Cell Signalling 4877 | WB |
| I-A$^b$ | PerCP-Cy5.5 | Rat IgG2a | AF6-120.1 | Biolegend 116416 | FC |
| ICOSL | PE | Rat IgG2a | HK5.3 | Biolegend 107405 | FC |

FIG. 17B (cont'd)

| | | | | | |
|---|---|---|---|---|---|
| IgA | FITC | Rat IgG1 | C10-3 | BD 559354 | FC |
| IgD | HRP | Goat IgG | — | Bethyl A90-103P | ELISA |
| IgG | PE-Cy7 | Rat IgG2a | 11-26c | eBioscience 25-5993 | FC |
| IgG | ALP | Horse IgG | — | Vector Laboratories AP-2000 | ELISA |
| IgG1 | HRP | Goat IgG | — | Jackson Immunoresearch 115-035-205 | ELISA |
| IgG1 | PE-CF594 | Rat IgG1 | A85-1 | BD 562559 | FC |
| IgG2b | HRP | Goat IgG | — | Jackson Immunoresearch 115-035-207 | ELISA |
| IgG3 | HRP | Goat IgG | — | Jackson Immunoresearch 115-035-209 | ELISA |
| | — | Goat IgG F(ab)2 | — | Southern Biotech 1022-01 | Stim |
| IgM | APC | Rat IgG2a | RMM-1 | Biolegend 406509 | FC |
| | HRP | Goat IgG | — | Bethyl A90-101P | ELISA |
| IL-17A | BV650 | Rat IgG1 | TC11-18H10 | Biolegend 506929 | FC |
| IL-22 | AF647 | Goat IgG | — | Biolegend 516406 | FC |
| Ly-6G | AF647 | Rat IgG2a | 1A8 | Biolegend 127610 | IF |
| NP38a | PE | — | — | Biosearch N-5070-1 | FC |
| PD-1 | FITC | Hamster IgG | J43 | eBioscience 11-9985 | FC |
| PD-1 | PE-Cy7 | Hamster IgG | J43 | eBioscience 25-9985 | FC |
| PD-L1 | PE-Cy7 | Rat IgG2b | 10F.9G2 | Biolegend 124314 | FC |
| PD-L2 | PE | Rat IgG2a | TY25 | BD 557796 | FC |
| Pol II | — | Goat IgG | — | Bethyl A303-835A | WB |
| Pol II Ser5 | — | Rabbit IgG | — | Bethyl A304-408A | WB |
| Spt5 | — | Rabbit IgG | — | Santa Cruz sc-28678 | WB |
| TCRβ | PerCP-Cy5.5 | Hamster IgG | H57-597 | Biolegend 109227 | FC |

FIG. 17B (cont'd)

| | | | | | |
|---|---|---|---|---|---|
| IgA | FITC | Rat IgG1 | C10-3 | BD 559354 | FC |
| IgD | HRP | Goat IgG | — | Bethyl A90-103P | ELISA |
| IgG | PE-Cy7 | Rat IgG2a | 11-26c | eBioscience 25-5993 | FC |
| IgG | ALP | Horse IgG | — | Vector Laboratories AP-2000 | ELISA |
| IgG1 | HRP | Goat IgG | — | Jackson Immunoresearch 115-035-205 | ELISA |
| IgG1 | PE-CF594 | Rat IgG1 | A85-1 | BD 562559 | FC |
| IgG2b | HRP | Goat IgG | — | Jackson Immunoresearch 115-035-207 | ELISA |
| IgG3 | HRP | Goat IgG | — | Jackson Immunoresearch 115-035-209 | ELISA |
| | — | Goat IgG F(ab)2 | — | Southern Biotech 1022-01 | Stim |
| IgM | APC | Rat IgG2a | RMM-1 | Biolegend 406509 | FC |
| | HRP | Goat IgG | — | Bethyl A90-101P | ELISA |
| IL-17A | BV650 | Rat IgG1 | TC11-18H10 | Biolegend 506929 | FC |
| IL-22 | AF647 | Goat IgG | — | Biolegend 516406 | FC |
| Ly-6G | AF647 | Rat IgG2a | 1A8 | Biolegend 127610 | IF |
| NP38A | PE | — | — | Biosearch N-5070-1 | FC |
| PD-1 | FITC | Hamster IgG | J43 | eBioscience 11-9985 | FC |
| | PE-Cy7 | Hamster IgG | J43 | eBioscience 25-9985 | FC |
| PD-L1 | PE-Cy7 | Rat IgG2b | 10F.9G2 | Biolegend 124314 | FC |
| PD-L2 | PE | Rat IgG2a | TY25 | BD 557796 | FC |
| Pol II | — | Goat IgG | — | Bethyl A303-835A | WB |
| Pol II Ser5 | — | Rabbit IgG | — | Bethyl A304-408A | WB |
| Spt5 | — | Rabbit IgG | — | Santa Cruz sc-28678 | WB |
| TCRβ | PerCP-Cy5.5 | Hamster IgG | H57-597 | Biolegend 109227 | FC |

FIG. 17D

| Isotype | Conjugation | Clone | Manufacturer | Use |
|---|---|---|---|---|
| d. Isotype control antibodies | | | | |
| Goat IgG | — | — | Santa Cruz sc-2028 | IF, IP |
| | AF647 | Poly24030 | Biolegend 403006 | FC |
| Goat IgG F(ab')2 | Biotin | — | Southern Biotech 0110-08 | FC |
| | FITC | — | Southern Biotech 0110-02 | FC, IF |
| Hamster IgG2 | PE | B81-3 | BD 550085 | FC |
| | PerCP-Cy5.5 | B81-3 | BD 560562 | FC |
| Hamster IgM | FITC | G235-1 | BD 553960 | FC |
| Mouse IgG1 | AF647 | MOPC-21 | Biolegend 400155 | FC |
| | APC | MOPC-21 | BD 555751, Biolegend 400120 | FC |
| | Biotin | MOPC-21 | Biolegend 400103 | FC |
| | PE | MOPC-21 | BD 555749 | FC |
| | PE-Cy7 | MOPC-21 | BD 555872, Biolegend 400126 | FC |
| Mouse IgG2a | FITC | X39 | BD 349051 | FC |
| Rabbit IgG | — | — | Santa Cruz sc-2027 | IF, IP, ChIP |
| | — | — | R&D AF008 | IF, IP, ChIP |
| Rat IgG1 | BV650 | RTK2071 | Biolegend 400437 | FC |
| | — | RTK2758 | Biolegend 400501 | IHC |
| | APC | RTK2758 | Biolegend 400511 | FC |
| Rat IgG2a | Biotin | Rat IgG2a | eBioscience 13-4321 | FC, IF |
| | eF570 | eBR2a | eBioscience 41-4321 | FC |
| | PE | eBR2a | eBioscience 12-4321 | FC |

FIG. 17D (cont'd)

| | | | | |
|---|---|---|---|---|
| | PerCP-Cy5.5 | RTK2758 | Biolegend 400531 | FC |
| | PE-Cy7 | RTK2758 | Biolegend 400521 | FC |
| | — | eB149/10H5 | eBioscience 14-4031 | IF, IHC, WB |
| | AF647 | A95-1 | BD 557691 | FC |
| | Biotin | RTK4530 | Biolegend 400603 | FC |
| | eF660 | eB149/10H5 | eBioscience 50-4031 | FC, IF |
| | PE | A95-1 | BD 553989 | FC |
| Rat IgG2b | PE-Cy7 | RTK4530 | Biolegend 400617 | FC |
| | APC | REA293 | Miltenyi Biotec 130-104-615 | IF |
| Recombinant human IgG | PE | REA293 | Miltenyi Biotec 130-104-613 | FC |

FIG. 17E

| Secondary antibody/reagent | Conjugation | Manufacturer | Use |
|---|---|---|---|
| e, Secondary antibodies | | | |
| Anti-biotin IgG | Magnetic microbeads | Miltenyi Biotec 130-090-485 | MACS |
| Donkey anti-goat IgG | HRP | Santa Cruz sc-2020 | WB |
| | AF546 | Thermo Fisher Scientific A10036 | IF |
| Donkey anti-mouse IgG | CF647 | Sigma-Aldrich SAB4600176 | IF |
| | HRP | Santa Cruz sc-2318 | WB |
| Donkey F(ab')2 anti-rat IgG | HRP | Jackson Immunoresearch 712-036-153 | WB |
| Goat F(ab')2 anti-mouse IgG | Cy3 | Jackson Immunoresearch 115-166-006 | IF |
| | FITC | Southern Biotech 1032-02 | IF |
| Goat F(ab')2 anti-rabbit IgG | Cy3 | Jackson Immunoresearch 111-166-047 | IF |
| Goat anti-rabbit IgG | HRP | Santa Cruz sc-2004 | WB |
| | AF488 | Thermo Fisher Scientific S11223 | IF |
| | AF546 | Thermo Fisher Scientific S11225 | IF |
| Streptavidin | PerCP-Cy5.5 | BD 551419 | FC |
| | BV605 | Biolegend 405229 | FC |
| | QDot605 | Thermo Fisher Scientific Q10101MP | FC |

METHODS FOR THE PRODUCTION OF THERAPEUTIC, DIAGNOSTIC, OR RESEARCH ANTIBODIES

CROSS REFERENCE TO RELATED APPLICATIONS

This is a continuation of co-pending U.S. application Ser. No. 16/118,090, filed Aug. 30, 2018, which claims priority to U.S. Provisional Application No. 62/552,292, filed on Aug. 30, 2017. Both prior applications are incorporated by reference in their entirety as if fully set forth herein.

FIELD OF THE DISCLOSURE

The current disclosure provides down-regulating autoimmune regulator (AIRE) function in B cells to produce antibodies that can be high affinity and/or neutralizing. The antibodies produced by the methods disclosed herein can be class-switched and have a high degree of somatic hypermutations as compared to antibodies produced in the absence of AIRE downregulation.

BACKGROUND OF THE DISCLOSURE

A healthy immune system harbors a properly diversified and selected repertoire of antibodies that is critical for effective immune defense and prevention of autoimmunity. B cells play a major role in this process by producing antigen-specific antibodies against pathogens and imparting immunological memory. For the successful generation of B cell immunity, naive B cell populations with membrane immunoglobulin receptors (B cell receptors, BCRs) recognizing specific antigens are selectively activated in specialized microenvironments called germinal centers (GCs) in secondary lymphatic organs such as the lymph nodes, tonsils, and spleen.

In the weeks following antigenic stimulation in the GC, the specific antibodies that are produced by B cells increase their affinity for the antigen in a gradual and stepwise manner, termed affinity maturation. Affinity maturation involves two interrelated processes: (1) somatic hypermutation (SHM) and (2) clonal selection.

During SHM, mutations are generated in the variable, antigen-binding coding sequences (known as complementarity-determining regions (CDR)) of immunoglobulin genes. The mutation rate is up to 1,000,000 times higher than in cell lines outside of the lymphoid system. The increased mutation rate results in 1-2 mutations per CDR. These mutations alter the binding specificity and binding affinities of the resultant antibodies that are produced.

During clonal selection, B cells that have undergone SHM must compete for growth limiting resources, including the availability of antigen. Follicular dendritic cells (FDCs) of the GCs present antigen to the B cells, and only the B cells expressing BCRs with the higher affinities for the antigen are selected to survive. Over several rounds of selection, the resultant secreted antibodies produced will have effectively increased affinities for the antigen.

Beyond SHM and clonal selection, GC B cells additionally go through class switch recombination (CSR) which is a process that irreversibly rearranges the immunoglobulin (Ig) heavy chain constant region genes. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgA is similarly subdivided into subclasses including IgA1 and IgA2. Class switch recombination rearranges the immunoglobulin (Ig) heavy chain constant region genes from IgM or IgD to IgG, IgA or IgE. Class switch recombination allows effector function to change while maintaining antigenic specificity. Examples of different effector functions include antibody-dependent cell-mediated cytotoxicity (ADCC); phagocytosis; down regulation of cell surface receptors (e.g. B cell receptors); and B cell activation.

Generation of such long-lived, high affinity class-switched antibodies with neutralization functions protects individuals from re-infection following a first exposure to an antigenic pathogen. This process underlies the success of most vaccines. Antibodies also play large roles in a variety of therapeutic, diagnostic, and research uses.

SUMMARY OF THE DISCLOSURE

The current disclosure provides systems and methods that improve the ability to generate antibodies against specific antigens. The systems and methods improve the ability to generate antibodies by down-regulating the function of the molecule autoimmune regulator (AIRE) in B cells. Down-regulating AIRE function results in the production of antibodies with increased somatic hypermutation (SHM) and class switch recombination (CSR), thereby facilitating the development of antibodies for clinical and biomedical research applications.

In particular embodiments, the produced antibodies are neutralizing antibodies. In particular embodiments, neutralizing antibodies significantly reduce or block the binding of pathogens and/or their virulence molecules to a host's cellular receptors, such that the pathogens are no longer able to cause cellular damage or enter the host's cells. In particular embodiments, neutralizing antibodies are produced following increased SHM in the FR regions of antibodies. In particular embodiments, the produced antibodies are high affinity antibodies.

REFERENCE TO SEQUENCE LISTING

The nucleic acid and amino acid sequences listed below are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "2GX8746.txt" created on or about Apr. 5, 2021, with a file size of 84 KB, contains the sequence listing for this application and is hereby incorporated by reference in its entirety. In the Sequence Listing:

SEQ ID NO: 1 is the amino acid sequence of AIRE [*Homo sapiens*]: Accession: CAA08759.1.

SEQ ID NO: 2 is the nucleotide sequence of AIRE [*Homo sapiens*]: NCBI Reference Sequence: NC_000021.9.

SEQ ID NO: 3 is the amino acid sequence of AIRE [*Mus musculus*]: Accession: ADZ48462.1.

SEQ ID NO: 4 is the nucleotide sequence of AIRE [*Mus musculus*]: NCBI Reference Sequence: NC_000076.6.

SEQ ID NO: 5 is the amino acid sequence of CD40 type II isoform [*Homo sapiens*]: Accession: CAC29424.1.

SEQ ID NO: 6 is the nucleotide sequence of CD40 molecule [*Homo sapiens*]: NCBI Reference Sequence: NC_000020.11.

SEQ ID NO: 7 is the amino acid sequence of CD40 [*Mus musculus*]: Accession: AA B08705.1.

SEQ ID NO: 8 is the nucleotide sequence of CD40 antigen [*Mus musculus*]: NCBI Reference Sequence: NC_000068.7.

SEQ ID NO: 9 is the nucleotide sequence of a representative single guide RNA (sgRNA) for Exon 1 of AIRE.

SEQ ID NO: 10 is the nucleotide sequence of a representative single guide RNA (sgRNA) for Exon 3 of AIRE.

SEQ ID NOs: 11 and 12 are the amino acid sequences of representative protein tags.

SEQ ID NO: 13 AID [*Homo sapiens*]: Accession: AAM95438.1.

BRIEF DESCRIPTION OF THE DRAWINGS

Many of the drawings submitted herewith are better understood in color. Applicant considers the color versions of the drawings as part of the original submission and reserve the right to present color images of the drawings in later proceedings.

FIG. 1A, Immunofluorescence analysis of the tonsillar tissue of a healthy donor for IgD, CD19, AIRE and DAPI-stained DNA, and the thymic tissue of a healthy donor for EpCAM, AIRE and DNA. The dotted line marks the boundary between tonsil follicular mantle zone and the follicle. Bars: 20 μm. The results represent 5 healthy tonsil donors and 2 healthy thymus donors. FIG. 1B, Flow cytometric analysis of AIRE expression in tonsillar CD19$^+$IgD$^+$CD38$^-$ naive B cells, CD19$^+$IgD$^+$CD38$^+$ FGC B cells, CD19$^+$IgD$^-$CD38$^+$ GC B cells and CD19$^+$IgD$^-$CD38$^-$ memory B cells. The data represent those from 5 donors. FIG. 1C, Immunofluorescence analysis of the splenic tissue of a B6 mouse immunised with 3 doses of sheep red blood cells (SRBCs) for IgD, AIRE, CD19 and DNA, and the thymic tissue of an immunised B6 mouse for UEA-1, AIRE and DNA. Bar: 20 μm. The results represent the splenic tissues of 5 mice and the thymic tissue of 3 mice. FIG. 1D, FIG. 1E, Flow cytometric and statistical analyses of AIRE (GFP) expression in splenic and ILN viable CD19$^+$B220$^+$FAS$^+$GL7$^+$ GC B cells, CD19$^+$B220$^+$FAS$^-$GL7$^-$ non-GC B cells and CD19$^{lo}$B220$^{lo}$CD138$^+$ plasma cells (PCs) of B6 mice (shaded histograms, n=4) or B6.Aire$^{Adig}$ mice (histograms, n=4) after immunization with 5 doses of NP$_{32}$-KLH. The results represent or compare 4 B6 and 4 B6.Aire$^{Adig}$ mice. FIG. 1F, Flow cytometric analysis of CD83 and CXCR4 expression on total and GFP$^+$ splenic GC B cells of an immunised B6.Aire$^{Adig}$ mouse, showing the distribution of GFP$^+$ GC B cells in CXCR4$^{hi}$CD83$^-$ DZ and CXCR4$^{lo}$CD83$^+$ LZ B cells. The result represents 4 B6.Aire$^{Adig}$ mice. FIG. 1G, Immunofluorescence analysis of the tonsillar tissue of a HIGM3 patient for IgD, AIRE, CD19 and DNA. The dotted line marks the boundary between follicular mantle zone and the follicle. Bars: 20 μm. FIG. 1H, Flow cytometric analysis of AIRE (GFP) expression in splenic B cells of a B6 or B6.Aire$^{Adig}$ mouse treated for 3 d with medium or CD40L with or without IL-4 in the absence (vehicle) or presence of CAPE. The data represent the results from 3 B6 and 3 B6.Aire$^{Adig}$ mice. P<0.01, *P<0.001, by 2-tailed t-test.

FIGS. 2A-2H. GC B cells in secondary lymphoid tissues express AIRE. FIGS. 2A-2D, Immunofluorescence analysis of tonsillar (2A, 2B) and splenic (2C, 2D) tissues of healthy donors for IgD, AIRE, CD19 and DNA, showing the presence of AIRE in the nuclei of follicular GC B cells. Follicular IgD$^+$ plasmablasts (arrow heads) did not contain AIRE. The areas 1 and 2 outlined in FIG. 2A and FIG. 2C are shown with a higher magnification of FIG. 2B and FIG. 2D, respectively. Dotted lines mark the boundary between follicular mantle zone and the follicle. Bars: 40 μm (FIG. 2A) and 15 μm (FIG. 2B). FIG. 2E, Flow cytometric gating strategy for identifying human peripheral blood naive (IgD$^+$CD27$^-$), MZ (IgD$^+$CD27$^+$), switched memory (IgD$^-$CD27$^+$), double-negative (IgD$^-$CD27$^-$) B cells, and transitional (CD24$^{hi}$CD38$^{hi}$), mature (CD24$^{int}$CD38$^{int}$), memory (CD24$^{hi}$CD38$^-$) B cells and plasma cells (CD24$^-$CD38$^{hi}$). 2F, AIRE expression in human peripheral blood B cell subsets, as determined by flow cytometry. The result is representative of 8 healthy donors. FIG. 2G, Flow cytometric gating strategy for identifying mouse splenic non-GC (CD19$^+$B220$^+$GL7$^-$FAS$^-$), GC (CD19$^+$B220$^+$GL7$^+$FAS$^+$) B cells and plasma cells (CD19$^{lo}$ B220$^{lo}$ CD138$^+$). FIG. 2H, AIRE expression in mouse peripheral blood, splenic, MLN, PP and thymic B cells of B6.Aire$^{Adig}$ mice. The data are representative of 12 B6.Aire$^{Adig}$ and 6 B6 mice that were age- and sex-matched and housed in the same SPF room.

FIGS. 3A-3D. AIRE expression in GC B cells requires CD40 signalling. FIGS. 3A-3D, Immunofluorescence analysis of tonsillar tissues of a healthy donor and a HIGM3 patient for IgD, AIRE, CD19 and DNA, showing the lack of AIRE expression in GC B cells in the HIGM3 patient. The HIGM3 tonsil harbors giant follicles with defective follicular Ig class switch recombination (CSR) and hence showing follicular IgD staining without follicular IgD$^+$ plasmablasts, although extrafollicular and subepithelial IgD$^+$ plasmablasts are present and generated via T cell-independent mechanisms. Chen et al., *Nature Immunology* 10, 889-898 (2009). The areas outlined in FIG. 3A and FIG. 3C are shown with a higher magnification in FIG. 3B and FIG. 3D, respectively. The dotted lines outline the follicles. Bars: 100 μm (FIG. 3A, 3C) or 25 μm (FIG. 3B, 3D).

FIG. 4A, FIG. 4B, qRT-PCR and Western Blot analyses of AIRE transcript and protein levels, the protein levels of total and Ser536-phosphorylated NF-κB p65, and total and Thr202/Tyr204-phosphorylated Erk1/2 in human peripheral blood IgD$^+$ B cells treated with medium or CD40L, or CD40L and IL-4, in the presence of vehicle or CAPE for 3 d. FIG. 4C, FIG. 4D, qRT-PCR and Western Blot analyses of AIRE transcript and AIRE protein levels in human 2E2 B cells treated with medium (Control) or CD40L and IL-21 for 3 d. FIG. 4E, FIG. 4F, qRT-PCR and Western Blot analyses of Aire transcript and AIRE protein levels in mouse CH12 cells treated with anti-CD40, TGF-β1 and ng/ml IL-4 for 3 d. *P<0.05, P<0.01, *P<0.001, by 2-tailed t-test. The data represent 3-4 experiments.

FIG. 5A, Purity of Aire$^{+/+}$ and Aire$^{-/-}$ littermate donor B cells before adoptive transfer. FIG. 5B, Cell surface expression of the differentiation and activation markers CD21, CD23, CD38, CD40, CD62L, CD80, CD86, CD93, I-A$^b$, BAFF-R and immunoglobulin IgM and IgD on purified Aire$^{+/+}$ and Aire$^{-/-}$ littermate donor B cells before adoptive transfer, as determined by flow cytometry. FIG. 5C, Percentage of GL7$^+$FAS$^+$ GC B cells in the spleens of μMT recipients of either Aire$^{+/+}$ or Aire$^{-/-}$ B cells that were immunised i.p. with 5 doses of NP$_{32}$-KLH. Flow cytometry was performed 4 d after the last immunization. FIG. 5D, Cell surface expression of the co-stimulatory or co-inhibitory molecules CD80, CD86, PD-L1, PD-L2 and ICOSL on GL7$^+$FAS$^+$ GC B cells in the spleens of μMT recipients after immunizations. Shaded histograms indicate the staining using isotype-matched control antibodies. FIG. 5E, 5F, Percentage of splenic PD-1$^+$CXCR5$^+$ T$_{FH}$ cells and PD-1$^+$CXCR5$^+$Foxp3$^+$CD25$^+$ T$_{FR}$ cells in the spleens of immunised μMT recipients. The results shown represent 4 experiments, each including B cells from 3-5 age- and sex-matched littermate donor mice and 6-8 age- and sex-matched littermate μMT recipient mice. FIG. 5G, CFSE dilution in purified B cells from age- and sex-matched littermate donor Aire$^{+/+}$ and Aire$^{-/-}$ mice treated with medium (Control) or CD40L and IL-4 for 5 or 7 d. Non-viable cells were excluded from the analysis. FIG. 5H, Six-hour EdU incorporation by Aire$^{+/+}$ or B cells stimulated for 5 d with CD40L and IL-4. FIG. 5I, Apoptosis of Aire$^{+/+}$ or Aire$^{-/-}$ B cells treated with medium (Control) or CD40L and IL-4 for 3 or 7 d, as determined by Annexin V and 7-AAD staining by flow cytometry. The results shown are representative of 3 experiments, each including cells from 2-3 age- and sex-matched littermate Aire$^{+/+}$ and Aire$^{-/-}$ mice.

FIG. 6A, Flow cytometric analysis of surface IgD and IgM on NP$_{36}$-binding B cells in μMT recipients of Aire$^{+/+}$ or Aire$^{-/-}$ B cells immunised with 5 doses of NP$_{32}$-KLH. The result represents 3 age- and sex-matched μMT recipients each of B cells from 3-5 age- and sex-matched littermate donor Aire$^{+/+}$ or Aire$^{-/-}$ mice. FIG. 6B, The ratios of the titers of circulating NP$_4$-binding to NP$_{29}$-binding IgM, IgG1, IgG2b and IgG3 in immunized μMT recipient mice of Aire$^{+/+}$ or Aire$^{-/-}$ B cells. The results represent 4 experiments, each including B cells from 3-5 age- and sex-matched littermate donor mice and 6-8 age- and sex-matched littermate μMT recipient mice. FIG. 6C, Flow cytometric analysis of surface IgM, IgG1 and IgA by Aire$^{+/+}$ or Aire$^{-/-}$ mouse splenic B cells stimulated ex vivo for 4 d. The results represent 3 experiments. FIG. 6D, ELISA of IgG1 and IgA in supernatants of Aire$^{+/+}$ or Aire$^{-/-}$ mouse splenic B cells stimulated ex vivo for 5 d with anti-CD40 and IL-4 (for IgG1) or anti-CD40, TGF-β and IL-4 (for IgA). The results represent 3 experiments. FIG. 6E, 6F, Flow cytometric and statistical analyses of IgA CSR in WT and Aire$^{-/-}$ CH12 cells treated with medium (Control) or stimulated with anti-CD40, TGF-β and IL-4 for 3 d. Relative CSR (FIG. 6E) was determined as the ratio of the percentages of IgA$^+$IgM$^-$ cells in stimulated samples to control samples followed by normalization of such ratios by setting the values of WT CH12 cells to 1. The results represent or compare 3 experiments involving WT, clones 43, 53 and 69, and 11 additional experiments involving WT and clone 69. FIG. 6G, qRT-PCR analysis of the Iα-Cμ circle transcript levels in WT and Aire$^{-/-}$ CH12 cells treated with medium (Control) or stimulated with anti-CD40, TGF-β and IL-4 for 3 d. The results compare 3 experiments. FIG. 6H, Flow cytometric analysis of IgA CSR in Aire$^{-/-}$ CH12 cells (clone 69) transfected with a construct expressing either NLS-deficient AIRE-GFP (AIRE$^{ΔNLS}$-GFP) or WT AIRE-GFP (AIRE$^{WT}$-GFP) and treated with medium (Control) or stimulated with anti-CD40, TGF-β and IL-4 for 3 d. The results represent 2 experiments. *P<0.05, P<0.01, *P<0.001, by 2-tailed t-test (FIGS. 6B, 6D, 6F) or 1-tailed t-test (FIG. 6G).

FIGS. 7A-7C, DNA sequencing (right panels) of the Aire gene (SEQ ID NO: 4) showing CRISPR-introduced mutations causing frame shift in both alleles. The deleted nucleotides are shaded in dark gray (top panels) with the deletion site indicated by dark gray arrows (bottom panels) in the sequencing results. The axons of Aire are shaded in light gray, with the amino acid translation shown above the nucleotide sequence and the stop codon introduced shaded in gray and marked with an asterisk. FIG. 7D, Verification of Aire mutations in CH12 clones by PCR using primers that only anneal to the WT sequence, giving no amplification in clones 43, 47 and 53. Clone 47 has a 3-bp deletion in both Aire alleles causing a single amino acid deletion, and hence was not used in experiments. FIG. 7E, Verification of Aire mutations in both alleles of CH12 clone 69 by PCR showing no amplification using primer pair #2 which anneals to the WT but not the mutated sequence. Primer pair #1 amplifies a sequence immediately downstream of the mutation site, and primer pair #3 is specific for the single-stranded repair template used in CRISPR. FIG. 7F, Western Blot analysis of AIRE protein expression in WT and Aire$^{-/-}$ CH12 cells.

FIG. 8A, qRT-PCR analysis of the Iγ1-Cμ circle transcript level in Aire$^{+/+}$ CH12 cells and Aire$^{-/-}$ CH12 cell clones 43, 53 and 69 that were either unstimulated or stimulated with anti-CD40, TGF-β1 and IL-4 for 3 days. The result was normalised using the respective Actb transcript level, and expressed as fold of induction relative to unstimulated Aire$^{+/+}$ CH12 cells. The data are representative of three experiments. FIG. 8B, 8C, Western Blot analysis of AID in WT and Aire$^{-/-}$ CH12 cells that were either unstimulated or stimulated with anti-CD40, TGF-β1 and IL-4 for 3 d. Lamin B1 and GAPDH were used as the control for nuclear and cytoplasmic proteins, respectively. The data are representative of 2 experiments. FIG. 8D, qRT-PCR analysis of Aicda and the Iμ-Cμ and Iα-Cα germline transcript levels in Aire$^{+/+}$ CH12 cells and Aire$^{-/-}$ CH12 cell clones 43, 53 and 69 that were either unstimulated or stimulated with anti-CD40, TGF-β1 and IL-4 for 3 d. FIG. 8E, Flow cytometric analysis of apoptosis by Annexin V and 7-AAD staining of WT and Aire$^{-/-}$ CH12 cells treated with medium (Control) or stimulated with anti-CD40, TGF-β1 and IL-4 for 3 d. FIG. 8F, Percentages of late apoptotic (Annexin V$^+$7-AAD$^+$) and early apoptotic (Annexin V$^+$7-AAD$^-$) in WT and Aire$^{-/-}$ CH12 cells treated with medium (Control) or stimulated with anti-CD40, TGF-β1 and IL-4 for 3 d. *P<0.05, by 2-tailed t-test. The data represent 4 experiments.

FIG. 9A, Imaging flow cytometric analysis of AIRE and AID in tonsillar IgD$^-$CD38$^+$ GC B cells of a healthy donor. Bars: 7 μm. The results represent 3 donors. FIG. 9B, FIG. 9C, Co-IP of AIRE and AID in tonsillar CD19$^+$ total, IgD$^+$ naive and FGC and CD19$^+$IgD$^-$ GC and memory B cells of a healthy donor, and in splenic CD19$^+$ B cells of a B6 mouse after 3 doses of immunization with SRBCs. The results are representative of tonsils of 4 donors and spleens of 3 mice. FIG. 9D, The domain structures of recombinant WT and mutant human AIRE and AID molecules. Dotted lines indicated the deleted regions in the mutant proteins. FIG. 9E, Co-IP of WT AID and WT or mutant AIRE in HKB-11 cells 24 h after transfection of plasmid(s) encoding WT AID and WT or mutant AIRE proteins. FIG. 9F, The domain structures of recombinant WT and mutant human AID molecules. FIG. 9G, Co-IP of WT AIRE and WT or mutant AID in HKB-11 cells 24 h after transfection of plasmid(s) encoding WT AIRE and WT or mutant AID proteins. The results in FIG. 9E and FIG. 9G are representative of 3 experiments. FIG. 9H, A dot blot assay for the genomic uracil content in WT and Aire$^{-/-}$ CH12 cells after 48 or 72 h of treatment without or with anti-CD40, TGF-β and IL-4. The results represent 3 experiments. FIG. 9I, ChIP-qPCR analysis for the interaction of AID with Sμ, Iµ and Sγ1 regions in WT and Aire$^{-/-}$ CH12 cells after 72 h of treatment without or with anti-CD40, TGF-β and IL-4. The results represent 3 experiments. FIG. 9J, Co-IP of AID with pSer5-Pol II, total Pol II, Spt5 and AIRE in WT and Aire$^{-/-}$ CH12 cells after 72 h of treatment without or with anti-CD40, TGF-β and IL-4. The results represent 3 experiments. *P<0.05, P<0.01, *P<0.001, by 2-tailed t-test.

FIGS. 10A-10F. AIRE and AID co-localize in the nuclei of GC B cells. FIG. 10A, The gating strategy to identify tonsillar naive (IgD$^+$CD38$^-$), founder GC (FGC) (IgD$^+$CD38$^+$), GC (IgD$^-$CD38$^+$) and switched memory (IgD$^-$CD38$^-$) B cells and switched plasma cells (PCs) (IgD$^-$CD38$^{hi}$) on the imaging flow cytometer. The plot displays MACS-purified CD19$^+$ tonsillar B cells. FIGS. 10B-10F, Imaging flow cytometry of AIRE and AID in tonsillar GC, naive, FGC, switched memory B cells and switched PCs of a healthy donor. DNA was counterstained with DAPI. Samples stained with isotype-matched control antibodies were used to define the fluorescence baseline for AIRE and AID. Four representative cells in each population stained with AIRE and AID or with isotype control antibodies were shown. Bars: 7 µg.

FIG. 11A, Co-IP of AIRE and AID in splenic B cells of immunised WT or Aicda$^{-/-}$ mice. The data represent 2 experiments. FIG. 11B, Western Blot analysis of Bcl10 in cytoplasmic and nuclear extracts of Ramos B cells unstimulated or stimulated with TNF for 24 h. FIG. 11C, Co-IP of AID and AIRE or Bcl10 in Ramos B cells unstimulated or stimulated with TNF for 24 h. The data in FIG. 11B and FIG. 11C represent 3 experiments. FIG. 11D, The principle of the uracil dot blot assay for the quantitation of genomic uracil. In stimulated Aire$^{+/+}$ or Aire$^{-/-}$ B cells, AID deaminates C to U in Ig V and S regions. U is excised by either endogenous Uracil N-glycosylase (UNG) or exogenously added *Escherichia coli* Uracil DNA glycosylase (UDG) during the assay to generate abasic sites (asterisk), which exist in an equilibrium between the closed and open ring forms. The active aldehyde in the open ring form reacts with the biotinylated aldehyde-reactive probe (Biotin-ARP), allowing biotinylation of the abasic site. Quantitation of biotinylated abasic sites with fluorochrome- or HRP-conjugated streptavidin after DNA dot blot by imaging or ELISA gives genomic U content. An increase in genomic U in Aire$^{-/-}$ B cells indicates increased activity of AID in the absence of AIRE. FIG. 11E, A representative standard calibration curve of the fluorescence intensity vs. uracil number of the assay.

FIGS. 12A-12C. Primers for cloning human AIRE and AID constructs.

FIG. 13A, The sorting and sequencing strategies for Aire$^{+/+}$ and Aire$^{-/-}$ donor B cells in µMT recipients after immunizations with 5 doses of NP$_{32}$-KLH. NP-specific B cells were sorted based on NP$_{36}$ binding. FIG. 13B, The SHM landscape across IgHV, including FR2, CDR2, FR3, CDR3 and FR4, of NP$_{36}$-binding IgM$^-$IgD$^-$ or IgM$^+$IgD$^+$ Aire$^{+/+}$ and Aire$^{-/-}$ donor B cells in µMT recipients after immunizations with NP$_{32}$-KLH. The result represents 3 µMT recipients of Aire$^{+/+}$ donor B cells and 3 µMT recipients of Aire$^{-/-}$ donor B cells.

FIG. 14A, Frequencies of C-to-T transitions in SHMs in IgHV of NP-specific IgG$^+$, IgA$^+$ or IgE$^+$ splenic B cells from µMT recipient mice of Aire$^{+/+}$ or Aire$^{-/-}$ B cells after 5 doses of immunizations with NP$_{32}$-KLH. FIG. 14B, qRT-PCR analysis of the fold induction of Iµ-Cγ1 and Iµ-Cγ3 post-switch transcript levels in peripheral blood IgD$^+$CD27$^-$ naïve B cells from healthy subjects (n=5) or APS-1 patients (n=5) stimulated for 3 d with CD40L and IL-4 or IFN-γ over the respective unstimulated control B cells. FIGS. 14C, 14D, GMS stain of cutaneous *C. albicans* and skin fungal burden (CFU per mg of tissue) in µMT recipient mice of Aire$^{+/+}$ or Aire$^{-/-}$ donor B cells 4 d after infection. Bars: 1 mm (FIG. 14C, upper panels) or 100 µm (FIG. 14C, lower panels). FIG. 14E, Levels of autoantibodies binding to IL-17A, IL-17F and IL-22 in the sera of µMT recipient mice of Aire$^{+/+}$ or Aire$^{-/-}$ donor B cells 4 d after infection. FIG. 14F, Flow cytometric analysis of IL-17A and IL-22 expression in cutaneous CD4$^+$ T cells of µMT recipient mice of Aire$^{+/+}$ or Aire$^{-/-}$ donor B cells 4 d after infection and after ex vivo re-stimulation. FIG. 14G, Immunofluorescence analysis of Ly-6G (red) and DNA (blue) in cutaneous tissues surrounding the *C. albicans* infection site in µMT recipient mice of Aire$^{+/+}$ or Aire$^{-/-}$ donor B cells 4 d after infection. The results in FIGS. 14C-14G represent 1 of 2 experiments, with 4 mice per group in each experiment. FIG. 14H, A simplified schematic of AIRE-mediated GC checkpoint of antibody diversification in B cells. At the T-B cell border of secondary lymphoid organs, B cells present antigens to and receive co-stimulation from DC-activated T cells, which also induce AIRE expression in B cells via CD40. The activated B cells enter the GC DZ and undergo SHM, proliferation and subsequent affinity selection by interacting with antigens on the surface of follicular dendritic cells (FDCs) in LZ. Low-affinity B cells will undergo apoptosis, whereas high-affinity B cells receive help from T follicular helper (TFH) cells to undergo CSR, and subsequently either re-enter the SHM-proliferation cycle in the DZ or exit the GC as plasma cells or memory B cells. AIRE in B cells limits autoantibody generation by restraining excessive AID activity in the GC. *P<0.05, **P<0.01, by 1-tailed t-test (FIGS. 14A, 14B left panel, FIGS. 14D, 14E) or 1-tailed Mann-Whitney U test (b right panel).

FIG. 15A, Flow cytometric gating strategy for identifying mouse skin viable CD45$^+$TCRγδ$^+$TCRβ$^-$γδ T cells, CD45$^+$TCRγδ$^-$TCRβ$^+$CD3$^+$CD4$^+$CD4$^+$ T cells and CD45$^+$TCRγδ$^-$TCRβ$^+$CD3$^+$CD4$^-$ CD8$^+$ T cells. FIG. 15B, IHC of CD4$^+$ T cells in cutaneous tissues surrounding the infection site in µMT recipient mice of Aire$^{+/+}$ or Aire$^{-/-}$ donor B cells 4 d after infection. Bars: 100 µm. FIG. 15C, Flow cytometric analysis of IL-17A and IL-22 expression in cutaneous CD8$^+$ and γδ T cells of µMT recipient mice of Aire$^{+/+}$ or Aire$^{-/-}$ donor B cells 4 d after infection. Data represent 2 experiments.

FIGS. 16A, 16B. qRT-PCR primers used in Example 1.

FIGS. 17A, 17B, 17D, 17E. Antibodies used in Example 1.

DETAILED DESCRIPTION

Figure 1A:
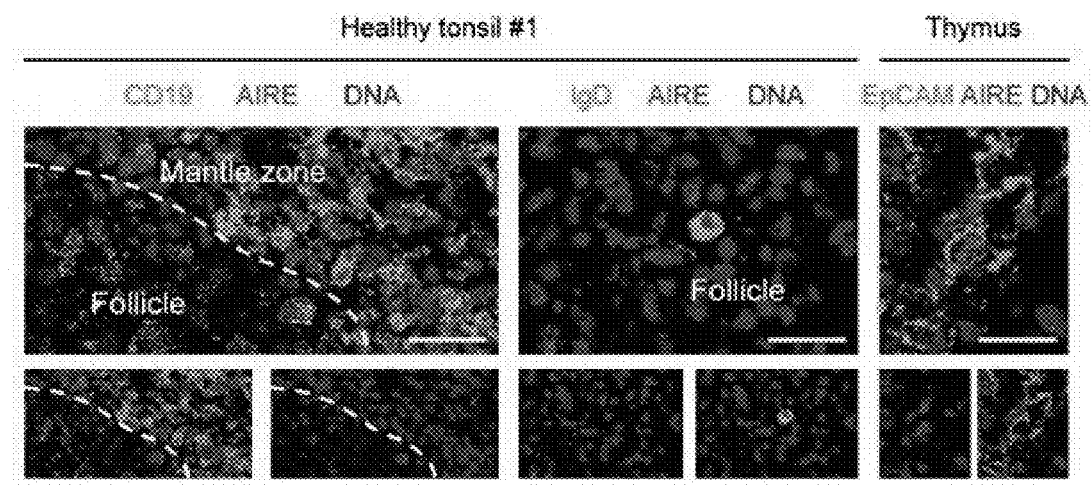
FIGS. 1A-1H. GC B cells express AIRE in a CD40-dependent manner.

A healthy immune system harbors a properly diversified and selected repertoire of antibodies that is critical for effective immune defense and prevention of autoimmunity. Mature B cells undergo antigen-driven antibody diversification via somatic hypermutation (SHM) and class-switch recombination (CSR) mediated by the enzyme activation-induced cytidine deaminase (AID) in germinal centers (GCs) of secondary lymphoid organs. Muramatsu et al., *Cell* 102, 553-563, (2000); Revy et al., *Cell* 102, 565-575, (2000).

Uncontrolled AID function can precipitate autoimmunity and cancer. Vinuesa et al., *Nature reviews. Immunology* 9, 845-857, (2009); Casellas et al. *Nature reviews. Immunology* 16, 164-176, (2016). Mutations in the autoimmune regulator (AIRE) gene, which normally promotes central and peripheral T cell tolerance (Anderson et al., *Science* 298, 1395-1401, (2002); Gardner et al., *Science* 321, 843-847, (2008); Malchow et al., *Science* 339, 1219-1224, (2013)), cause autoimmune polyglandular syndrome type 1 (APS-1) (Nagamine et al., *Nature genetics* 17, 393-398, (1997); Finnish-German, *Nature genetics* 17, 399-403, (1997)) associated with aberrant production of autoantibodies by B cells, organ-specific autoimmunity and increased susceptibility to mucocutaneous *Candida albicans* infection. Anderson et al., *Science* 298, 1395-1401, (2002).

The current disclosure provides that AIRE in GC B cells inhibits immunoglobulin affinity maturation (e.g., SHM) and CSR. When AIRE function is down-regulated, antigen-specific B cells develop into antibody-secreting plasma cells that produce antibodies with increased affinity and/or neutralization function. The down-regulation of AIRE improves antibody production not only in cultured B cells, but also in mouse models with AIRE deficiency. Moreover, in AIRE-deficient mice, there is an increased population of helper T cells (Tfh). Tfh cells are a type of T cell that specializes in promoting GC B cells to produce high affinity class-switched antibodies and evoking a more rapid memory B cell response to previously encountered antigens.

The systems and methods of the disclosure can be used for the generation of antibodies in both the primary immune response and the recall immune response in vivo as well as in B cell cultures in vitro. Uses of generated antibodies include therapeutic uses (e.g., antibody-based therapeutics for cancer, autoimmune, and inflammatory diseases) and diagnostic and/or research uses (e.g., flow cytometry, imaging, immunohistochemistry, western blot).

Particular embodiments include increasing SHM and CSR during antibody production by selecting a first population of B cells with down-regulated AIRE function; and contacting the selected B cell population with an antigen; thereby increasing SHM and CSR during antibody production. In particular embodiments, the increase can be in relation to antibodies produced by selecting a second population of B cells with normal AIRE function; and contacting the second selected B cell population with the same antigen under comparable conditions.

Figure 6A:
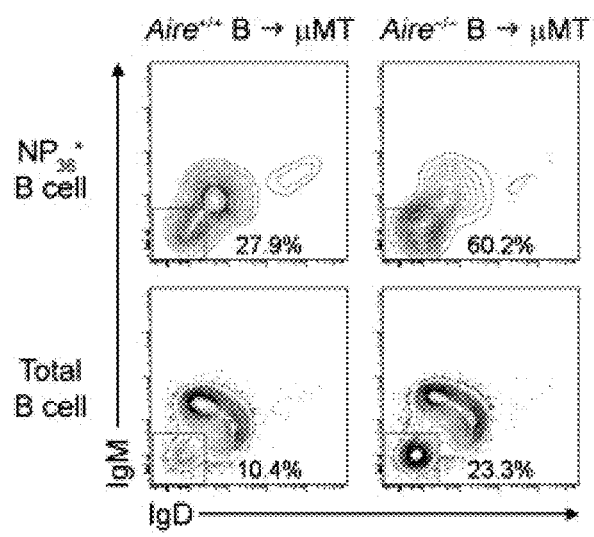
FIGS. 6A-6H. AIRE in B cells inhibits Ig diversification.
Figure 6B:
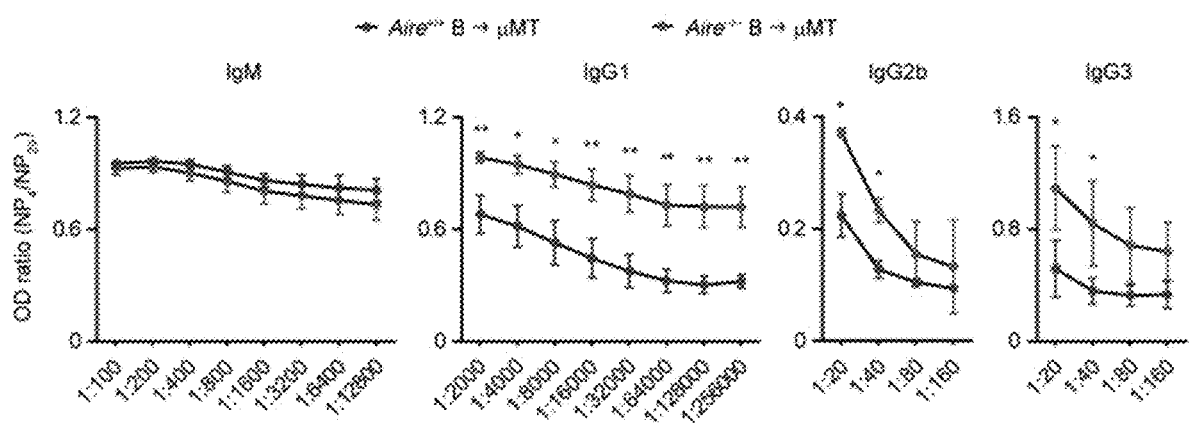
Figure 6C:
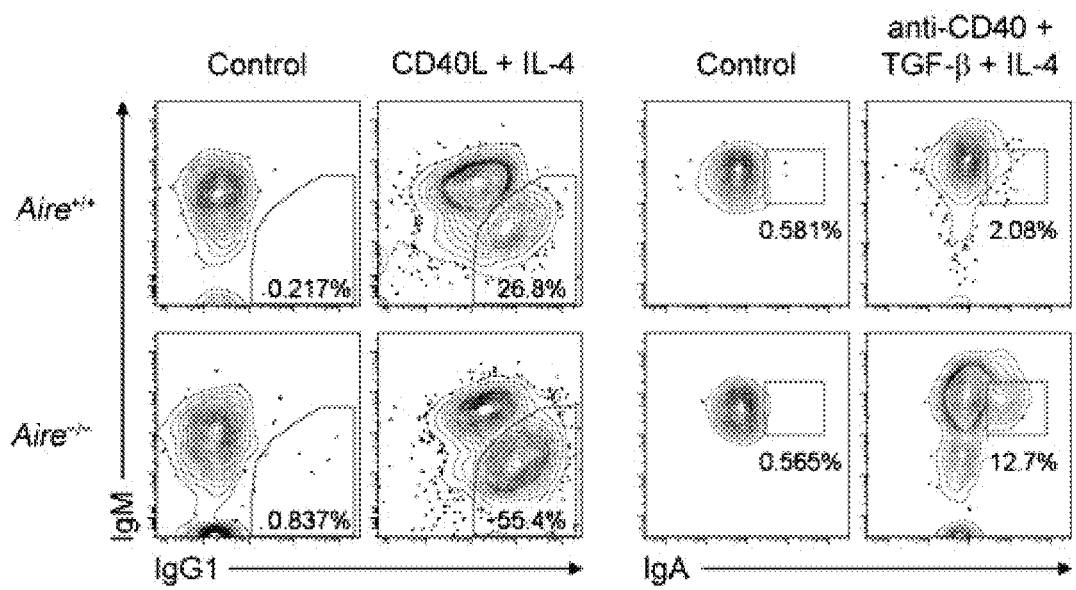

In particular embodiments, increased SHM can be confirmed by the methods used to generate the data presented in FIG. 6B. Briefly, antigens of a lower oligomeric number (in this case $NP_4$) and those of a higher oligomeric number (in this case $NP_{29}$) are coated onto the wells of microtiter plates. Samples containing the antibodies whose affinity is to be determined are applied to the coated microtiter plates. Antibodies of high affinity would be able to bind to the antigens with a lower oligomeric number, and those of both high and low affinity would be able to bind to the antigens with a higher oligomeric number. The ratios of binding to the lower oligomeric antigens to the higher oligomeric antigens would be an indication of the proportion of high-affinity antibodies in a given sample. In particular embodiments, the increase can be a statistically-significant increase.

In particular embodiments, increased CSR can be confirmed by the methods used to generate the data presented in FIGS. 6C, 6D, 6E, 6F and 6G. Briefly, the expression of cell surface immunoglobulin is measured by flow cytometry. A reduction in IgM, the antibody expressed before CSR, and an increase in various subclasses of IgG, IgA or IgE expression on the cell surface indicates CSR. In addition, the secretion of the various classes of IgG, IgA or IgE into the supernatant would also increase after the B cells are class switched. In particular embodiments, the changes can be statistically-significant changes.

In particular embodiments, "under comparable conditions" refers to experimental conditions under which one of ordinary skill the art would expect similar results (i.e., lack of a statistically significant difference between groups), but for an experimental variable.

Particular embodiments include methods of producing neutralizing antibodies against a pathogen by selecting a population of B cells with down-regulated AIRE function; and contacting the selected B cell population with an antigen of the pathogen; thereby producing neutralizing antibodies against the pathogen.

Function as a neutralizing antibody can be shown through the ability to block or reduce cellular function as measured by flow cytometry. In particular embodiments percent neutralization can refer to a percent decrease in infectivity in the presence of an antibody, as compared to pathogen infectivity in the absence of the antibody. For example, if half as many cells in a sample become infected in the presence of an antibody, as compared to in the absence of the antibody, this can be calculated as 50% neutralization. In particular embodiments neutralizing antibodies result in at least 40% neutralization, at least 50% neutralization, at least 60% neutralization, at least 70% neutralization, at least 80% neutralization, or at least 90% neutralization. In particular embodiments, antibodies produced according to the disclosure can block infection by a pathogen (i.e., 100% neutralization).

Particular embodiments include methods of producing antibodies with high affinity for an antigen by selecting a population of B cells with down-regulated AIRE function; and contacting the selected B cell population with the antigen; thereby producing antibodies with high affinity for the antigen.

In particular embodiments, high affinity can be confirmed by an increased ratio of binding to $NP_4$ to $NP_{29}$ of the antibodies made by Aire$^{-/-}$ B cells than those made by Aire$^{+/+}$ B cells under comparable conditions. In particular embodiments, the increased ratio can be statistically-significant.

Particular embodiments include kits for producing antibodies with increased SHM and CSR including: a B cell population with down-regulated AIRE function; and an antigen.

Particular embodiments include kits for producing antibodies with increased SHM and CSR including: a B cell population; gene editing agents to down-regulate AIRE function and/or CD40 function in the B cell population; and an antigen.

Aspects of the current disclosure are now described in more detail.

Embodiments disclosed herein include utilizing B cells with down-regulated AIRE activity. In particular embodiments, B cells may naturally have down-regulated AIRE function, as compared to a reference level. Reference levels can include "normal" or "control" levels or values, defined according to, e.g., discrimination limits or defining thresholds, in order to define down-regulated AIRE function. The reference level can include AIRE function levels typically found in natural B cells not associated with a condition that includes down-regulated AIRE function. Other terms for "reference levels" include "index," "baseline," "standard," "healthy," etc. In particular embodiments, "reference level" can refer to a standardized control value for normal AIRE function which represents levels not associated with any pathological disease or condition.

In particular embodiments, B cells may have experimentally down-regulated AIRE function. In these embodiments, normal AIRE function refers to AIRE function observed in the absence of an experimental procedure to down-regulate AIRE function. Down-regulated AIRE function refers to AIRE function following an experimental procedure to down-regulate AIRE function. The different levels can be compared to confirm down-regulated AIRE function, as is understood by one of ordinary skill in the art.

Any method to down-regulate AIRE function can be used. Particular embodiments can utilize gene-editing agents. As used herein, gene editing agents modify or affect a B cell's endogenous genome. In particular embodiments, the modification includes removal or disruption of an endogenous gene such that the endogenous gene's encoded protein is no longer expressed, expressed to a reduced degree, expressed as an incomplete protein, an unstable protein, an incorrectly folded protein and/or a nonfunctional protein. For example, as disclosed herein, AIRE mutants missing one or more of the N-terminal caspase activation and recruitment domain (CARD) and/or nuclear localization signal (NLS) lose the ability to interact with AID. Thus, these forms of AIRE are down-regulated. The current disclosure also provides that AIRE expression in B cells is dependent on CD40 signaling. Accordingly, AIRE function can be down-regulated by interfering with CD40 expression and/or signaling.

Particular embodiments utilize CRISPR-Cas to down-regulate AIRE. CRISPR-Cas systems include CRISPR repeats and a set of CRISPR-associated genes (Cas).

The CRISPR repeats (clustered regularly interspaced short palindromic repeats) include a cluster of short direct repeats separated by spacers of short variable sequences of similar size as the repeats. The repeats range in size from 24 to 48 base pairs and have some dyad symmetry which implies the formation of a secondary structure, such as a hairpin, although the repeats are not truly palindromic. The spacers, separating the repeats, match exactly the sequences from prokaryotic viruses, plasmids, and transposons. The Cas genes encode nucleases, helicases, RNA-binding proteins, and a polymerase that unwind and cut DNA. Cas1, Cas2, and Cas9 are examples of Cas genes.

The source of CRISPR spacers indicate that CRISPR-Cas systems play a role in adaptive immunity in bacteria. There are at least three types of CRISPR-Cas immune system reactions, and Cas1 and Cas2 genes are involved in spacer acquisition in all three. Spacer acquisition, involving the capture and insertion of invading viral DNA into a CRISPR locus occurs in the first stage of adaptive immunity. More particularly, spacer acquisition begins with Cas1 and Cas2 recognizing invading DNA and cleaving a protospacer, which is ligated to the direct repeat adjacent to a leader sequence. Subsequently, single strand extension repairs take place and the direct repeat is duplicated.

The next stage of CRISPR-related adaptive immunity involves CRISPR RNA (crRNA) biogenesis, which occurs differently in each type of CRISPR-Cas system. In general, during this stage, the CRISPR transcript is cleaved by Cas genes to produce crRNAs. In the type I system, Cas6e/Cas6f cleaves the transcript. The type II system employs a trans-activating (tracr) RNA to form a dsRNA, which is cleaved by Cas9 and RNase III. The type III system uses a Cash homolog for cleavage.

In the final stage of CRISPR-related adaptive immunity, processed crRNAs associate with Cas proteins to form interference complexes. In type I and type II systems, the Cas proteins interact with protospacer adjacent motifs (PAMs), which are short 3-5 bp DNA sequences, for degradation of invading DNA, while the type III systems do not require interaction with a PAM for degradation. In the type III-B system, the crRNA basepairs with the mRNA, instead of the targeted DNA, for degradation.

CRISPR-Cas systems thus function as an RNAi-like immune system in prokaryotes. The CRISPR-Cas technology has been exploited to inactivate genes in human cell lines and cells. As an example, the CRISPR-Cas9 system, which is based on the type II system, has been used as an agent for genome editing.

The type II system requires three components: Cas9, crRNA, and tracrRNA. The system can be simplified by combining tracrRNA and crRNA into a single synthetic single guide RNA (sgRNA).

At least three different Cas9 nucleases have been developed for genome editing. The first is the wild type Cas9 which introduces double strand breaks (DSBs) at a specific DNA site, resulting in the activation of DSB repair machinery. DSBs can be repaired by the non-homologous end-joining (NHEJ) pathway or by homology-directed repair (HDR) pathway. The second is a mutant Cas9, known as the Cas9D10A, with only nickase activity, which means that it only cleaves one DNA strand and does not activate NHEJ. Thus, the DNA repairs proceed via the HDR pathway only. The third is a nuclease-deficient Cas9 (dCas9) which does not have cleavage activity but is able to bind DNA. Therefore, dCas9 is able to target specific sequences of a genome without cleavage. By fusing dCas9 with various effector domains, dCas9 can be used either as a gene silencing or activation tool.

Other gene-editing agents may also be used. For example, particular embodiments can utilize transcription activator-like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or by homologous recombination (HR) with an exogenous double-stranded donor DNA fragment.

As indicated, TALENs have been engineered to bind a target sequence and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. The FokI domain functions as a dimer requiring two constructs with unique DNA binding domains for sites on the target sequence. The FokI cleavage domain cleaves within a five or six base pair spacer sequence separating the two inverted half-sites.

Particular embodiments can utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the MegaTAL only requires the delivery of a single peptide chain for functional activity.

Particular embodiments can utilize zinc finger nucleases (ZFNs) as gene editing agents. ZFNs are a class of site-specific nucleases engineered to bind and cleave DNA at specific positions. ZFNs are used to introduce DSBs at a specific site in a DNA sequence which enables the ZFNs to target unique sequences within a genome in a variety of different cells. Moreover, subsequent to DSB, homologous recombination or non-homologous end joining takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease.

Particular embodiments may also utilize interfering RNA-type mechanisms to down-regulate AIRE.

SEQ ID NOs: 1-4 (see FIG. 18) provide exemplary human and mouse AIRE protein and gene sequences. SEQ ID NO: 4 provides an exemplary AIRE gene sequence reflecting GenBank NC_000076.6. SEQ ID NOs: 5-8 provide exemplary human and mouse CD40 protein and gene sequences. Additional nucleic acid sequences encoding AIRE and CD40 proteins can be identified by those of ordinary skill in the art, and can include one or more of various sequence polymorphisms, mutations, and/or sequence variants (e.g., splice variants or codon optimized variants). Sequence information provided by public databases can be used to identify additional gene and protein sequences that can be used with the systems and methods disclosed.

Available prediction software can be used to generate guide RNA sequences to use in the aforementioned gene-editing methods. The utilized guide RNA sequences will be rare or unique in the genome to minimize or eliminate interaction with potential off-target sites. Particular embodiments can utilize the following two single guide RNA (sgRNA) sequences: AIREsg2 (Exon 1) 5'GCACCGCACCGAGATCGCGG(TGG)3' (SEQ ID NO: 9) and AIRE sg3 (Exon 3) 5'ACCTAAACCAGTCCCG-GAAA(GGG)3' (SEQ ID NO: 10).

Embodiments disclosed herein include producing antibodies by exposing B cells with down-regulated AIRE function to antigens. Any antigen can be used. Particular examples include bacterial antigens, viral antigens, fungal antigens, and cancer antigens.

Exemplary bacterial antigens include anthrax protective antigen, lipopolysaccharides, toxin A (tcdA), toxin B (tcdB), capsular polysaccharides, diphtheria toxin, α-crystallin, mycolic acid, heat shock protein 65 (HSP65), hemagglutinin, pertactin, FIM2, FIM3, adenylate cyclase, pneumolysin, pneumococcal capsular polysaccharides, type 3 secretion system (T3SS), PcrV protein, PsI exopolysaccharide, rompA, α toxin, and tetanus toxin.

Exemplary viral antigens include envelope glycoprotein B, CMV pp65, EBV EBNAI, EBV P18, EBV P23, the S, M, and L proteins of hepatitis B virus, the pre-S antigen of hepatitis B virus, HBCAG DELTA, HBV HBE, hepatitis C viral RNA, HCV NS3, HCV NS4, HIV gp32, HIV gp41, HIV gp120, HIV gp160, HIV P17/24, HIV P24, HIV P55 GAG, HIV P66 POL, HIV TAT, HIV GP36, the Nef protein, hemagglutinin, neuraminidase, the measles virus fusion protein, rabies glycoprotein, rabies nucleoprotein, the respiratory syncytial viral fusion protein VP7sc, protein E1, and protein E2.

Exemplary fungal antigens include spherule antigens, capsular polysaccharides, heat shock protein 60 (HSP60), gp63, lipophosphoglycan, merozoite surface antigens, sporozoite surface antigens, circumsporozoite antigens, gametocyte/gamete surface antigens, the blood-stage antigen pf 155/RESA, glutathione-S-transferase, paramyosin, trichophytin, SAG-1, and p30.

Exemplary cancer antigens include CD19, CD20, CD33, CD133, ERBB2, GD2, HER2, mesothelin, PSCA, PSMA, ROR1, and WT1.

Particular embodiments disclosed herein include producing antibodies by exposing B cells with down-regulated AIRE function to antigens and adjuvants. An adjuvant refers to a material that enhances the immune response to an antigen. The precise mode of action is not understood for all adjuvants, but such lack of understanding does not prevent their use.

Any adjuvant can be used within the teachings of the current disclosure. Exemplary adjuvants include Toll-like receptor ligands, squalene-based adjuvants, alum, STING agonists, and cytokines.

Exemplary Toll-like receptor ligands include CpG, Cpg-28, Polyriboinosinic polyribocytidylic acid (Poly(I:C)), α-galactoceramide, MPLA, Motolimod, imiquimod, MGN1703, and Hiltonol.

Squalene is a triterpene that can be derived from certain plant sources, such as rice bran, wheat germ, amaranth seeds, and olives, as well as from animal sources, such as shark liver oil. Examples of squalene-based adjuvants include MF59® (Novartis, Basel, Switzerland) and Addavax™ (InvivoGen, San Diego, CA).

Alum refers to a family of salts that contain two sulfate groups, a monovalent cation, and a trivalent metal, such as aluminum or chromium. Alum is an FDA approved adjuvant.

"STING" is an abbreviation of "stimulator of interferon genes". Exemplary STING agonists include c-AIMP; (3',2') c-AIMP; (2',2')c-AIMP; (2',3')c-AIMP; c-AIMP(S); c-(dAMP-dIMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)](POM)2; and DMXAA.

Naturally occurring antibody structural units include a tetramer. Each tetramer includes two pairs of polypeptide chains, each pair having one light chain and one heavy chain.

The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific antigen epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

As indicated previously, SMH occurs in the CDR regions including the 3 heavy chain CDRs and the 3 light chain CDRs. Systems and methods disclosed herein can result in an increased mutation rate in CDR regions and/or FR regions (see, e.g., FIG. 13B). Thus, as used herein, increased SHM can include increased SHM in CDR regions and/or FR regions. An important feature of many neutralizing antibodies (e.g., HIV-1 neutralizing antibodies) is the increased number of mutations in FR regions (which is usually not mutated or poorly mutated during "regular" SHM (i.e., SHM in the absence of AIRE downregulation). Particular embodiments disclosed herein include producing antibodies with increased FR mutations.

The carboxy-terminal portion of each chain defines a constant region that can be responsible for effector function. Examples of effector functions include: C1q binding and complement dependent cytotoxicity (CDC); antibody-dependent cell-mediated cytotoxicity (ADCC); phagocytosis; down regulation of cell surface receptors (e.g. B cell receptors); and B cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgA is similarly subdivided into subclasses including IgA1 and IgA2. As indicated previously, CSR rearranges the immunoglobulin (Ig) heavy chain constant region genes from IgM or IgD to an IgG, IgA or IgE.

A human antibody is one which includes an amino acid sequence which corresponds to that of an antibody produced by a human or a human cell or derived from a non-human source that utilizes human antibody repertoires or other human antibody-encoding sequences.

Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an antigen to a transgenic animal that has been modified to produce intact human antibodies or intact antibodies with human variable regions in response to antigenic challenge. Such animals contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Traditional strategies for hybridoma development using mice, llamas, chicken, rats, hamsters, rabbits, etc. can also be used.

If produced antibodies are not human, such antibodies can be humanized. A "humanized" antibody refers to a chimeric antibody including amino acid residues from non-human CDRs and amino acid residues from human FRs. In particular embodiments, a humanized antibody will include substantially all of at least one, and typically two, variable domains, in which all or substantially all of the CDRs correspond to those of a non-human antibody, and all or substantially all of the FRs correspond to those of a human antibody. A humanized antibody optionally may include at least a portion of an antibody constant region derived from a human antibody. A "humanized form" of an antibody, e.g., a non-human antibody, refers to an antibody that has undergone humanization.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

A human consensus framework is a framework which represents the most commonly occurring amino acid residues in a selection of human immunoglobulin variable light ($V_L$) or variable heavy ($V_H$) framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

Once antibodies have been generated, their CDRs can be identified. Definitive delineation of a CDR and identification of residues including the binding site of an antibody can be accomplished by solving the structure of the antibody and/or solving the structure of the antibody-antigen complex. In particular embodiments, this can be accomplished by methods such as X-ray crystallography.

CDRs from antibodies produced according to the methods disclosed herein can be utilized in a variety of binding domain formats. For example, particular embodiments can include binding fragments of an antibody, e.g., Fv, Fab, Fab', F(ab')$_2$, Fc, and single chain Fv fragments (scFvs) or any biologically effective fragments of an immunoglobulin that bind specifically to targeted antigen.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody, but lack the constant regions. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird et al., Science 242 (1988) 423-426; Huston et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including $V_L$, $V_H$, CL and CH1 domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger et al., Proc. Natl. Acad. Sci. USA 90:6444-6448, 1993. Dual affinity retargeting antibodies (DART™; based on the diabody format but featuring a C-terminal disulfide bridge for additional stabilization (Moore et al., Blood 117, 4542-51, 2011)) can also be formed. Antibody fragments can also include isolated CDRs. For a review of antibody fragments, see Hudson et al., Nat. Med. 9:129-134, 2003.

Unless otherwise indicated, the term "antibody" includes antibodies including two full-length heavy chains and two full-length light chains, the fragments as described above, and variants. Furthermore, unless explicitly excluded, antibodies can include monoclonal antibodies, human or humanized antibodies, bispecific antibodies, polyclonal antibodies, linear antibodies, minibodies, domain antibodies, synthetic antibodies, chimeric antibodies, antibody fusions, and fragments thereof, respectively.

A monoclonal antibody refers to an antibody obtained from a population of substantially homogeneous antibodies, i.e., the individual antibodies including the population are identical and/or bind the same antigen epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes of an antigen, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, monoclonal antibodies can be made by a variety of techniques, including the hybridoma method, recombinant DNA methods, and methods utilizing transgenic animals containing all or part of the human immunoglobulin loci.

Variants of antibodies can include those having one or more conservative amino acid substitutions or one or more non-conservative substitutions that do not adversely affect the binding of the antibody.

In particular embodiments, a conservative amino acid substitution may not substantially change the structural characteristics of the reference antibody (e.g., a replacement amino acid should not tend to break a helix that occurs in the reference sequence, or disrupt other types of secondary structure that characterizes the reference sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N.Y. (1991)); and Thornton et al., Nature, 354:105 (1991).

In particular embodiments, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

In particular embodiments, a $V_L$ region can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared to an antibody produced and characterized according to methods disclosed herein. An insertion, deletion or substitution may be anywhere in the $V_L$ region, including at the amino- or carboxy-terminus or both ends of this region, provided that each CDR includes zero changes or at most one, two, or three changes and provided an antibody including the modified $V_L$ region can still specifically bind its target antigen with an affinity similar to the reference antibody.

In particular embodiments, a $V_H$ region can be derived from or based on a disclosed $V_H$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with when compared to an antibody produced and characterized according to methods disclosed herein. An insertion, deletion or substitution may be anywhere in the $V_H$ region, including at the amino- or carboxy-terminus or both ends of this region, provided that each CDR includes zero changes or at most one, two, or three changes and provided an antibody including the modified $V_H$ region can still specifically bind its target epitope with an affinity similar to the reference antibody.

In particular embodiments, one or more amino acid modifications may be introduced into the Fc region of an antibody, thereby generating an Fc region variant. The Fc region variant may include a human Fc region sequence (e.g., a human IgG1, IgG2, IgG3 or IgG4 Fc region) including an amino acid modification (e.g. a substitution) at one or more amino acid positions.

In particular embodiments, variants have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live.

Antibodies produced according to the methods disclosed herein have high affinity for their target antigens. In particular embodiments "affinity" refers to the strength of the sum total of noncovalent interactions between a single binding site of an antibody and its target antigen. Unless indicated otherwise, "binding affinity" refers to intrinsic binding affinity which reflects a 1:1 interaction between members of a binding pair (i.e., antibody and target antigen). The affinity of an antibody for its target antigen can generally be represented by the dissociation constant (Kd) or the association constant ($K_A$). Affinity can be measured by common methods known in the art.

In particular embodiments, binding affinities can be assessed in relevant in vitro conditions, such as a buffered salt solution approximating physiological pH (7.4) at room temperature or 37° C.

In particular embodiments, "high affinity" means that the antibody associates with its target antigen with a dissociation constant (1(D) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the antibody does not bind to other biomolecules present, (e.g., it binds to other biomolecules with a dissociation constant (KD) of $10^{-4}$ M or more, in particular embodiments of from $10^{-4}$ M to 1 M).

In particular embodiments, "high affinity" means that the antibody associates with its target antigen with an affinity constant (i.e., association constant, $K_A$) of $10^7$ $M^{-1}$ or more, in particular embodiments of from $10^5$ $M^{-1}$ to $10^{13}$ $M^{-1}$, in particular embodiments of from $10^5 M^{-1}$ to $10^{10}$ $M^{-1}$, in particular embodiments of from $10^5$ $M^{-1}$ to $10^8$ $M^{-1}$, in particular embodiments of from $10^7$ $M^{-1}$ to $10^{13}$ $M^{-1}$, or in particular embodiments of from $10^7$ $M^{-1}$ to $10^8$ $M^{-1}$. The term can be further used to indicate that the antibody does not bind to other biomolecules present, (e.g., it binds to other biomolecules with an association constant ($K_A$) of $10^4$ $M^{-1}$ or less, in particular embodiments of from $10^4$ $M^{-1}$ to 1 $M^{-1}$).

In particular embodiments, "high affinity" is relative to an antibody produced in the absence of AIRE down-regulation.

In particular embodiments, developed antibodies can be produced from a gene using a protein expression system. Protein expression systems can utilize DNA constructs (e.g., chimeric genes, expression cassettes, expression vectors, recombination vectors) including a nucleic acid sequence encoding the protein or proteins of interest operatively linked to appropriate regulatory sequences. In particular embodiments, such DNA constructs are not naturally occurring DNA molecules and are useful for introducing DNA into host-cells to express selected proteins of interest. In particular embodiments, a DNA construct that encodes an antibody can be inserted into cells (e.g., bacterial, mammalian, insect, etc.), which can produce the antibody encoded by the DNA construct.

Operatively linked refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N.Y., 1989.

Expression control sequences are DNA sequences involved in any way in the control of transcription or translation. Suitable expression control sequences and methods of making and using them are well known in the art. Expression control sequences generally include a promoter. The promoter may be inducible or constitutive. It may be naturally occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979.

The promoter may include, or be modified to include, one or more enhancer elements. In particular embodiments, the promoter will include a plurality of enhancer elements. Promoters including enhancer elements can provide for higher levels of transcription as compared to promoters that do not include them.

For efficient expression, the coding sequences can be operatively linked to a 3' untranslated sequence. In particular embodiments, the 3' untranslated sequence can include a transcription termination sequence and a polyadenylation sequence. The 3' untranslated region can be obtained, for example, from the flanking regions of genes.

In particular embodiments, a 5' untranslated leader sequence can also be employed. The 5' untranslated leader sequence is the portion of an mRNA that extends from the 5' CAP site to the translation initiation codon.

In particular embodiments, a "hisavi" tag can be added to the N-terminus or C-terminus of a gene by the addition of nucleotides coding for the Avitag amino acid sequence, "GLNDIFEAQKIEWHE" (SEQ ID NO: 11), as well as the 6× histidine tag coding sequence "HHHHHH (SEQ ID NO: 12)". The Avitag avidity tag can be biotinylated by a biotin ligase to allow for biotin-avidin or biotin-streptavidin based interactions for protein purification, as well as for immunobiology (such as immunoblotting or immunofluorescence) using anti-biotin antibodies. The 6× histidine tag allows for protein purification using $Ni^{-2+}$ affinity chromatography.

In particular embodiments, the DNA constructs can be introduced by transfection, a technique that involves introduction of foreign DNA into the nucleus of eukaryotic cells. In particular embodiments, the proteins can be synthesized by transient transfection (DNA does not integrate with the genome of the eukaryotic cells, but the genes are expressed for 24-96 hours). Various methods can be used to introduce the foreign DNA into the host-cells, and transfection can be achieved by chemical-based means including by the calcium phosphate, by dendrimers, by liposomes, and by the use of cationic polymers. Non-chemical methods of transfection include electroporation, sono-poration, optical transfection, protoplast fusion, impalefection, and hydrodynamic delivery. In particular embodiments, transfection can be achieved by particle-based methods including gene gun where the DNA construct is coupled to a nanoparticle of an inert solid which is then "shot" directly into the target-cell's nucleus. Other particle-based transfection methods include magnet assisted transfection and impalefection.

EXEMPLARY EMBODIMENTS

Exemplary Embodiments—Set 1

1. A method of increasing somatic hypermutation (SHM) and class switch recombination (CSR) during antibody production including selecting a first population of B cells with down-regulated autoimmune regulator (AIRE) function; and contacting the first selected B cell population with an antigen; thereby increasing SHM and CSR during antibody production wherein the increase is in relation to antibodies produced by selecting a second population of B cells with normal AIRE function; and contacting the second selected B cell population with the same antigen under comparable conditions.
2. A method of embodiment 1 further including contacting the first selected B cell population and the second selected B cell population with an adjuvant.
3. A method of embodiment 1 or 2 further including isolating the produced antibodies with increased SHM and CSR.
4. A method of any of embodiments 1-3 further including determining the CDR sequences of the produced antibodies with increased SHM and CSR.
5. A method of any of embodiments 1-4 further including modifying B cells to down-regulate AIRE function.
6. A method of embodiment 5 wherein the modifying produces the selected population of B cells of embodiment 1.
7. A method of embodiment 5 or 6 wherein the modifying includes AIRE gene editing and/or CD40 gene editing.
8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.
9. A method of any of embodiments 5-8 wherein the AIRE gene editing includes contacting the modified B cells with SEQ ID NO: 9 and SEQ ID NO: 10.
10. A method of any of embodiments 5-8 wherein the modifying results in AIRE protein that does not interact with AID.
11. A method of embodiment 10 wherein the AIRE protein lacks its caspase activation and recruitment domain (CARD) and/or its nuclear localization signal (NLS).
12. A method of embodiment 10 wherein the AIRE protein lacks amino acids 110-114 and 131-133 or lacks amino acids 101-180.
13. A method of any of embodiments 1-12 wherein the selected first and second B cell populations are within different but comparable in vitro culture conditions.
14. A method of embodiment 13 further including stimulating the first and second B cell populations within the in vitro culture conditions.
15. A method of embodiment 14 wherein the stimulating includes adding CD40L, IL-4, IFN-γ or TGF-β
16. A method of any of embodiments 1-12 wherein the selected first and second B cell populations are in vivo in a subject.
17. A method of embodiment 16 wherein the in vivo selected B cell populations are within a mouse, llama, chicken, rat, hamster, or rabbit.
18. A method of embodiment 16 or 17 further including administering the selected first population of B cells to the subject.
19. A method of embodiment 18 wherein the selected first population of B cells are $AIRE^{-/-}$.
20. A method of embodiment 17 wherein the mouse produces human antibodies.
21. A method of any of embodiments 1-20 wherein the produced antibodies are human antibodies.
22. A method of any of embodiments 1-20 wherein the produced antibodies are non-human antibodies.
23. A method of embodiment 22 further including humanizing the produced antibodies.
24. A method of any of embodiments 1-23 wherein the antigen is a viral antigen, a bacterial antigen, a fungal antigen, or a cancer antigen.
25. A method of any of embodiments 2-24 wherein the adjuvant is a Toll-like receptor ligand, a squalene-based adjuvant, alum, a STING agonist, and/or a cytokine.
26. A method of any of embodiments 1-25 wherein the increased SHM is within CDR regions, FR regions, or CDR regions and FR regions.

Exemplary Embodiments—Set 2

1. A method of producing a neutralizing antibody including selecting a population of B cells with down-regulated autoimmune regulator (AIRE) function; and contacting the selected B cell population with an antigen; thereby producing a neutralizing antibody.
2. A method of embodiment 1 further including contacting the selected B cell population with an adjuvant.
3. A method of embodiment 1 or 2 further including isolating the neutralizing antibody.
4. A method of any of embodiments 1-3 further including determining the CDR sequences of the neutralizing antibody.

5. A method of any of embodiments 1-4 further including modifying B cells to down-regulate AIRE function.
6. A method of embodiment 5 wherein the modifying produces the selected population of B cells of embodiment 1.
7. A method of embodiment 5 or 6 wherein the modifying includes AIRE gene editing and/or CD40 gene editing.
8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.
9. A method of any of embodiments 5-8 wherein the AIRE gene editing includes contacting the modified B cells with SEQ ID NO: 9 and SEQ ID NO: 10.
10. A method of any of embodiments 5-8 wherein the modifying results in AIRE protein that does not interact with AID.
11. A method of embodiment 10 wherein the AIRE protein lacks its caspase activation and recruitment domain (CARD) and/or its nuclear localization signal (NLS).
12. A method of embodiment 10 wherein the AIRE protein lacks amino acids 110-114 and 131-133 or lacks amino acids 101-180.
13. A method of any of embodiments 1-12 wherein the selected B cell population is within in vitro culture conditions.
14. A method of embodiment 13 further including stimulating the B cell population within the in vitro culture conditions.
15. A method of embodiment 14 wherein the stimulating includes adding CD40L, IL-4, IFN-γ or TGF-β
16. A method of any of embodiments 1-12 wherein the selected B cell population is in vivo in a subject.
17. A method of embodiment 16 wherein the in vivo selected B cell population is within a mouse, llama, chicken, rat, hamster, or rabbit.
18. A method of embodiment 16 or 17 further including administering the selected B cell population to the subject.
19. A method of embodiment 18 wherein the selected B cell population is AIRE$^{-/-}$.
20. A method of embodiment 17 wherein the mouse produces a human neutralizing antibody.
21. A method of any of embodiments 1-20 wherein the produced neutralizing antibody is a human neutralizing antibody.
22. A method of any of embodiments 1-20 wherein the produced neutralizing antibody is a non-human neutralizing antibody.
23. A method of embodiment 22 further including humanizing the produced neutralizing antibody.
24. A method of any of embodiments 1-23 wherein the antigen is a viral antigen, a bacterial antigen, a fungal antigen, or a cancer antigen.
25. A method of any of embodiments 2-24 wherein the adjuvant is a Toll-like receptor ligand, a squalene-based adjuvant, alum, a STING agonist, and/or a cytokine.

Exemplary Embodiments—Set 3

1. A method of producing antibodies with high affinity for an antigen including selecting a population of B cells with down-regulated autoimmune regulator (AIRE) function; and contacting the selected B cell population with the antigen; thereby producing antibodies with high affinity for the antigen.

2. A method of embodiment 1 further including contacting the selected B cell population with an adjuvant.
3. A method of embodiment 1 or 2 further including isolating the produced antibodies.
4. A method of any of embodiments 1-3 further including determining the CDR sequences of the produced antibodies.
5. A method of any of embodiments 1-4 further including modifying B cells to down-regulate AIRE function.
6. A method of embodiment 5 wherein the modifying produces the selected population of B cells of embodiment 1.
7. A method of embodiment 5 or 6 wherein the modifying includes AIRE gene editing and/or CD40 gene editing.
8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.
9. A method of any of embodiments 5-8 wherein the AIRE gene editing includes contacting the modified B cells with SEQ ID NO: 9 and SEQ ID NO: 10.
10. A method of any of embodiments 5-9 wherein the modifying results in AIRE protein that does not interact with AID.
11. A method of embodiment 10 wherein the AIRE protein lacks its caspase activation and recruitment domain (CARD) and/or its nuclear localization signal (NLS).
12. A method of embodiment 11 wherein the AIRE protein lacks amino acids 110-114 and 131-133 or lacks amino acids 101-180.
13. A method of any of embodiments 1-13 wherein the selected B cell population is within an in vitro culture.
14. A method of embodiment 13 further including stimulating the B cell population within the in vitro culture conditions.
15. A method of embodiment 14 wherein the stimulating includes adding CD40L, IL-4, IFN-γ or TGF-β.
16. A method of any of embodiments 1-15 wherein the selected B cell population is in vivo.
17. A method of embodiment 16 wherein the in vivo selected B cell populations are within a mouse, llama, chicken, rat, hamster, or rabbit.
18. A method of embodiment 16 or 17 further including administering the selected first population of B cells to the subject.
19. A method of embodiment 18 wherein the selected first population of B cells are AIRE$^{-/-}$.
20. A method of embodiment 17 wherein the mouse produces human antibodies.
21. A method of any of embodiments 1-20 wherein the produced antibodies are human antibodies.
22. A method of any of embodiments 1-21 wherein the produced antibodies are non-human antibodies.
23. A method of embodiment 22 further including humanizing the produced antibodies.
24. A method of any of embodiments 1-23 wherein the antigen is a viral antigen, a bacterial antigen, a fungal antigen, or a cancer antigen.
25. A method of any of embodiments 2-24 wherein the adjuvant is a Toll-like receptor ligand, a squalene-based adjuvant, alum, a STING agonist, and/or a cytokine.

Exemplary Embodiments—Set 4

1. A kit for antibodies including: a B cell population with down-regulated AIRE function; and an antigen.
2. A kit of embodiment 1 further including an adjuvant.

3. A kit of embodiment 1 or 2 further including CD40L, IL-4, IFN-γ and/or TGF-β.
4. A kit of any of embodiments 1-3 wherein the B cell population is in vitro.
5. A kit of any of embodiments 1-3 wherein the B cell population is in vivo.
6. A kit of any of embodiments 1-3 including an in vitro B cell population with down-regulated AIRE function and an in vivo B cell population with down-regulated AIRE function.
7. A kit of any of embodiments 1-6 wherein the B cell population is AIRE$^{-/-}$.
8. A kit of any of embodiments 1-6 wherein the B cell population expresses an AIRE protein that does not interact with AID.
9. A kit of embodiment 8 wherein the AIRE protein lacks its caspase activation and recruitment domain (CARD) and/or its nuclear localization signal (NLS).
10. A kit of embodiment 9 wherein the AIRE protein lacks amino acids 110-114 and 131-133 or lacks amino acids 101-180.
11. A kit of embodiment 5 or 6 wherein the in vivo B cell population is within a mouse, llama, chicken, rat, hamster, or rabbit.
12. A kit of embodiment 11 wherein the mouse produces human antibodies.
13. A kit of any of embodiments 1-12 wherein the antigen is a viral antigen, a bacterial antigen, a fungal antigen, or a cancer antigen.
14. A kit of any of embodiments 2-13 wherein the adjuvant is a Toll-like receptor ligand, a squalene-based adjuvant, alum, a STING agonist, and/or a cytokine.

Exemplary Embodiments—Set 5

1. A kit for producing antibodies including: a B cell population; gene editing agents to down-regulate AIRE function and/or CD40 function in the B cell population; and an antigen.
2. A kit of embodiment 1 further including an adjuvant.
3. A kit of embodiment 1 or 2 further including CD40L, IL-4, IFN-γ and/or TGF-β.
4. A kit of any of embodiments 1-3 wherein the B cell population is in vitro.
5. A kit of any of embodiments 1-3 wherein the B cell population is in vivo.
6. A kit of any of embodiments 1-3 including an in vitro B cell population with down-regulated AIRE function and an in vivo B cell population with down-regulated AIRE function.
7. A kit of any of embodiments 1-6 wherein the B cell population is AIRE$^{-/-}$.
8. A kit of any of embodiments 1-6 wherein the B cell population expresses an AIRE protein that does not interact with AID.
9. A kit of embodiment 8 wherein the AIRE protein lacks its caspase activation and recruitment domain (CARD) and/or its nuclear localization signal (NLS).
10. A kit of embodiment 9 wherein the AIRE protein lacks amino acids 110-114 and 131-133 or lacks amino acids 101-180.
11. A kit of embodiment 5 or 6 wherein the in vivo B cell population is within a mouse, llama, chicken, rat, hamster, or rabbit.
12. A kit of embodiment 11 wherein the mouse produces human antibodies.
13. A kit of any of embodiments 1-12 wherein the antigen is a viral antigen, a bacterial antigen, a fungal antigen, or a cancer antigen.
14. A kit of any of embodiments 2-13 wherein the adjuvant is a Toll-like receptor ligand, a squalene-based adjuvant, alum, a STING agonist, and/or a cytokine.
15. A kit of any of embodiments 1-14 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.
16. A kit of any of embodiments 1-15 wherein the gene editing agents include SEQ ID NO: 9 and/or SEQ ID NO: 10.

Also provided is use of a method or kit of any of the preceding embodiments to increase SHM mutations in the FR regions of antibodies.

Example 1. AIRE Inhibits AID-Mediated Antibody Diversification in Germinal Centre B Cells and Limits Autoimmunity Example 1 shows that AIRE is expressed in GC B cells in a CD40-dependent manner, interacts via its caspase activation and recruitment domain (CARD) and nuclear localization signal (NLS) with AID, and negatively regulates AID-mediated antibody diversification. AIRE-deficient mouse B cells undergo elevated CSR and affinity maturation after antigenic stimulation, which correlates with enhanced generation of genomic uracil, elevated Ig SHM, augmented AID targeting to Ig switch regions and increased interaction of AID with transcriptionally stalled RNA polymerase II (Pol II). Consistently, naive B cells of APS-1 patients undergo increased CSR upon stimulation ex vivo. Mice with AIRE deficiency in B cells have elevated levels of autoantibodies against T helper 17 ($T_H17$) effector cytokines and heightened skin *C. albicans* burden after infection, which recapitulates APS-1 patients. The disclosed results define a previously unknown but crucial B cell-intrinsic AIRE-dependent GC checkpoint of antibody diversification that limits autoimmunity, and illuminate new approaches of generating high-affinity neutralizing antibodies for therapeutic, diagnostic and research applications.

Figure 1B:
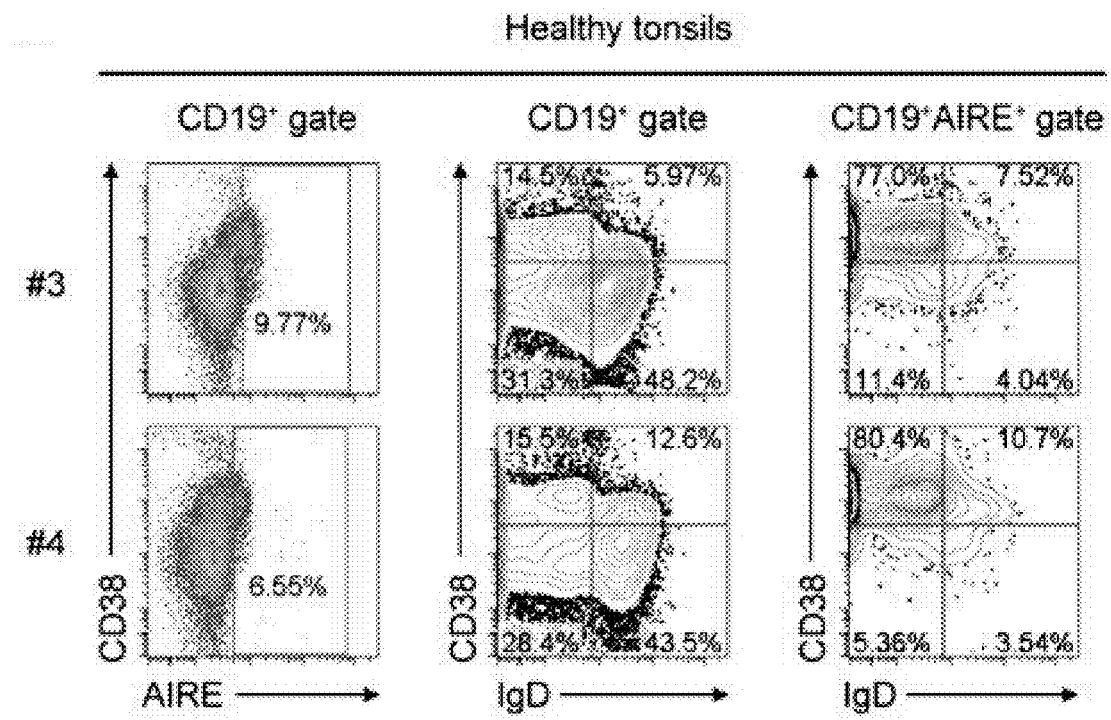
Figure 1C:
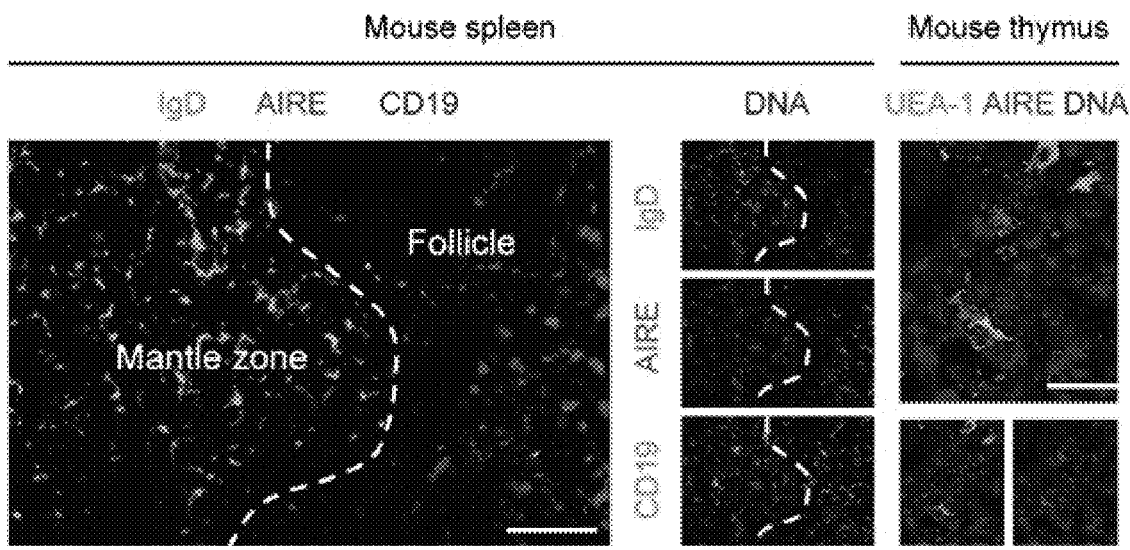
Figure 1D:
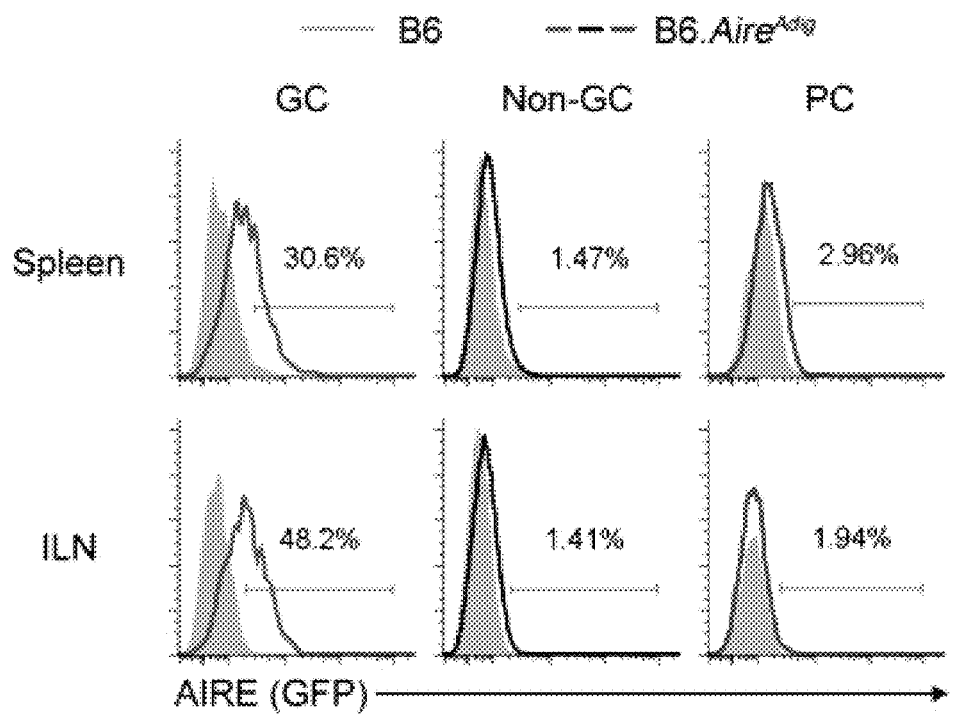
Figure 1E:
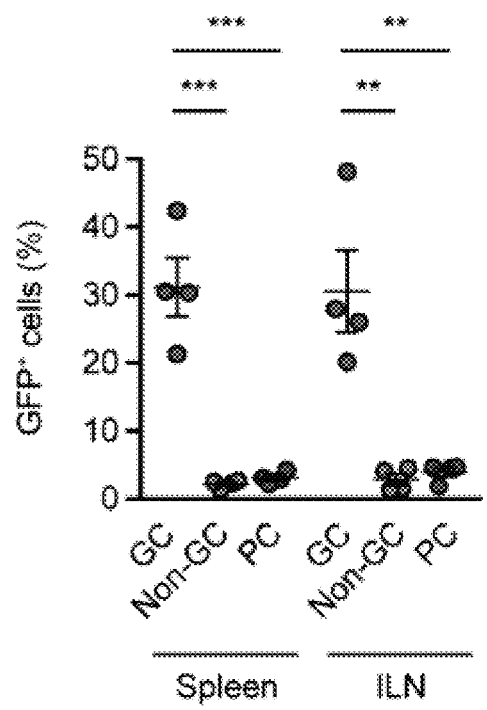
Figure 2A:
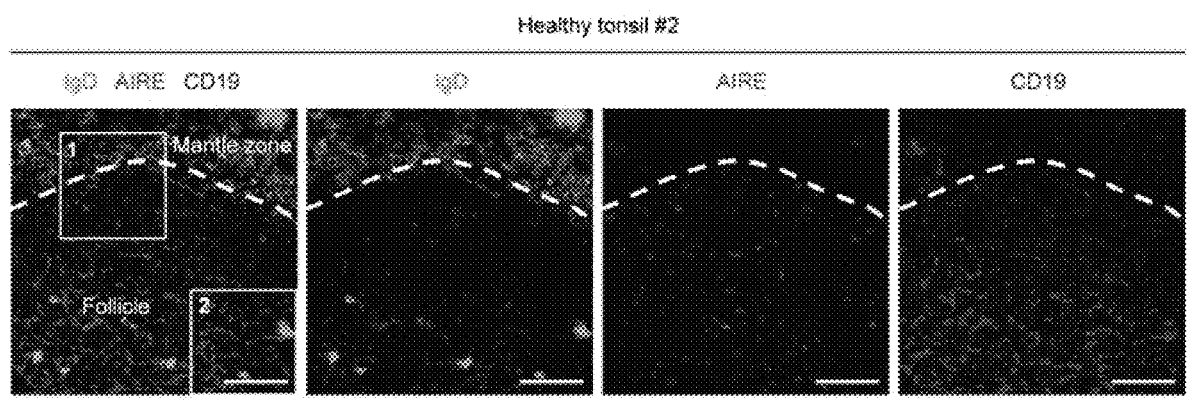
Figure 2B:
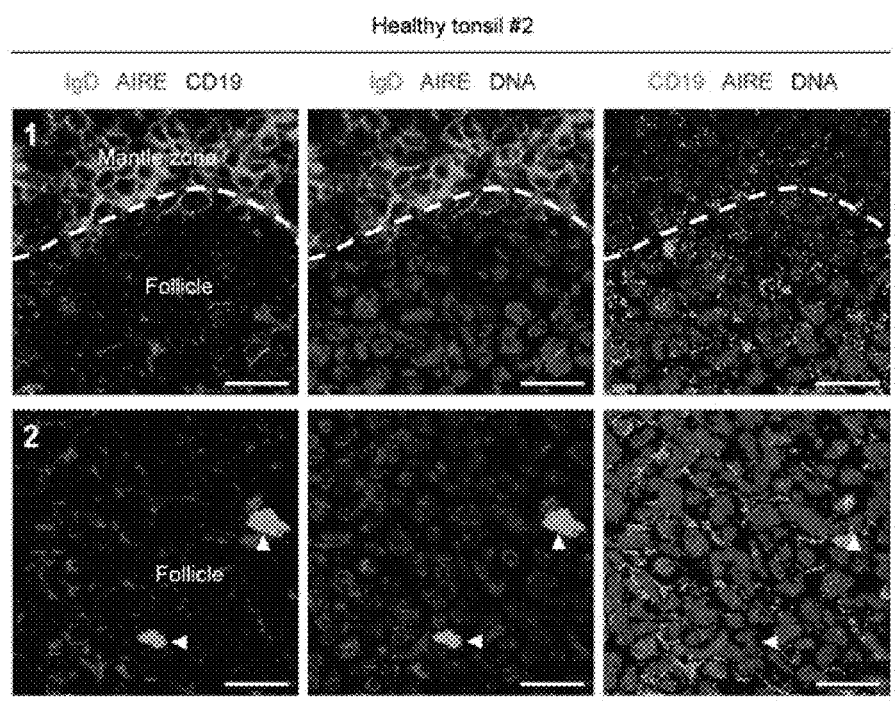
Figure 2C:
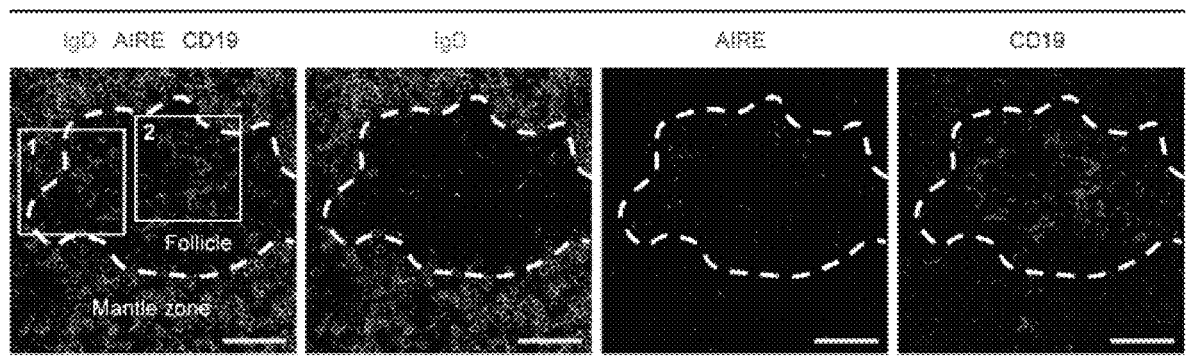
Figure 2D:
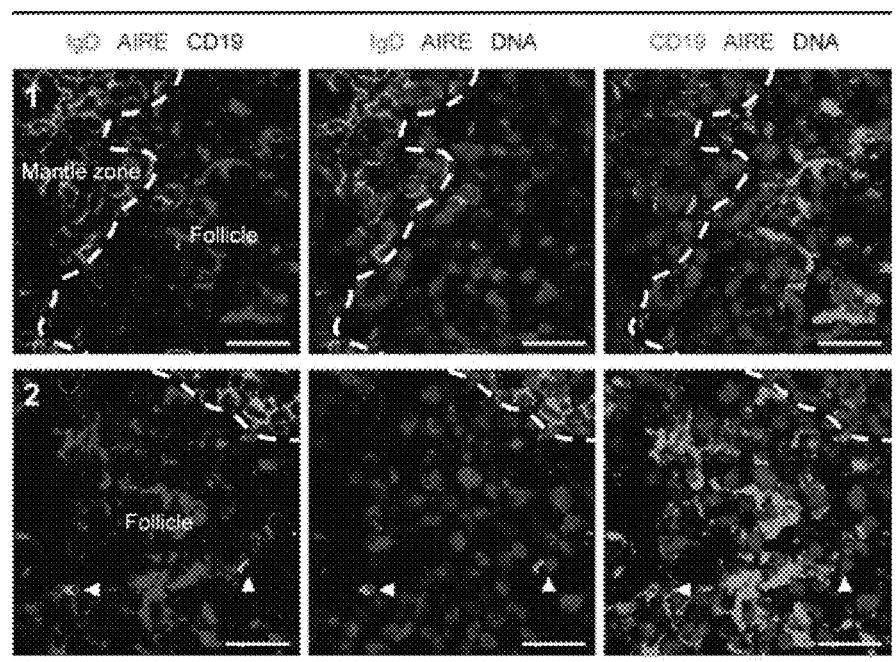
Figure 2E:
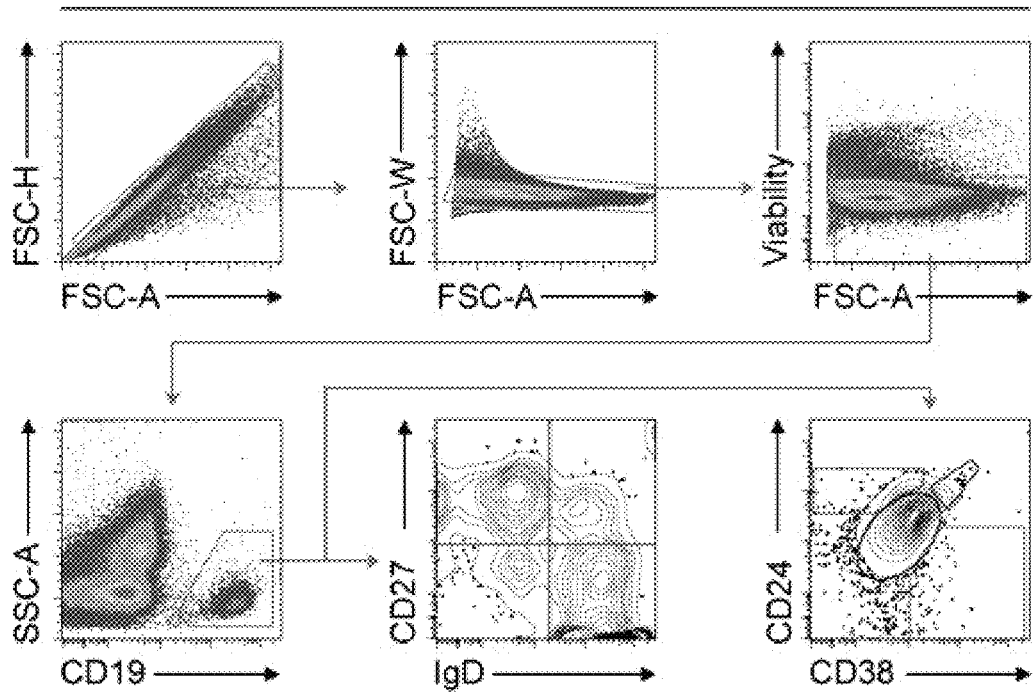
Figure 2F:
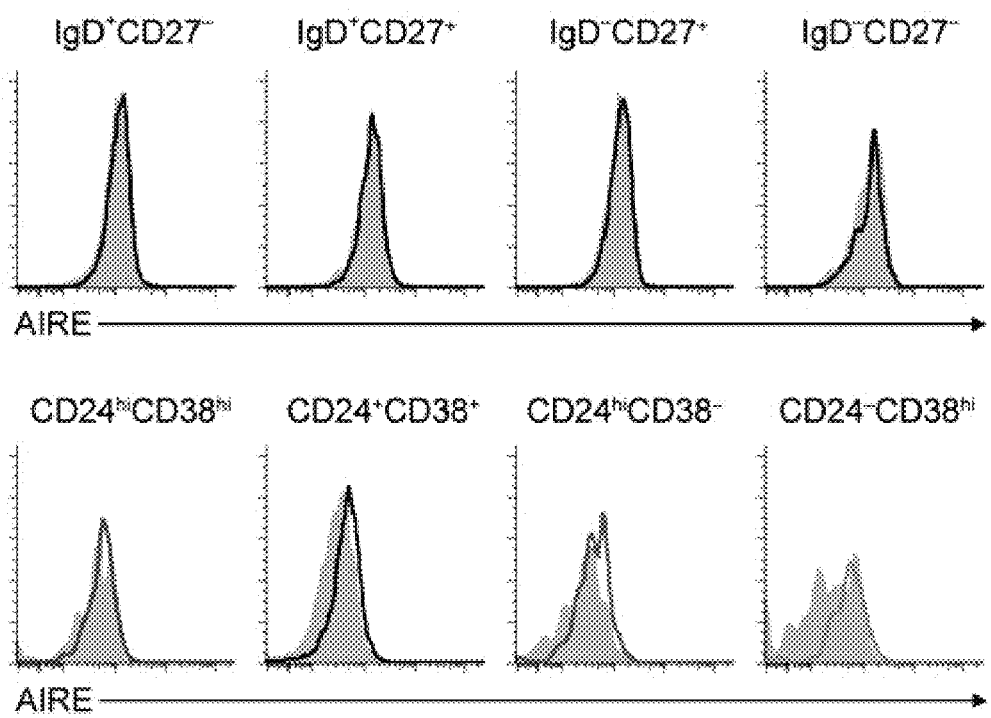
Figure 2G:
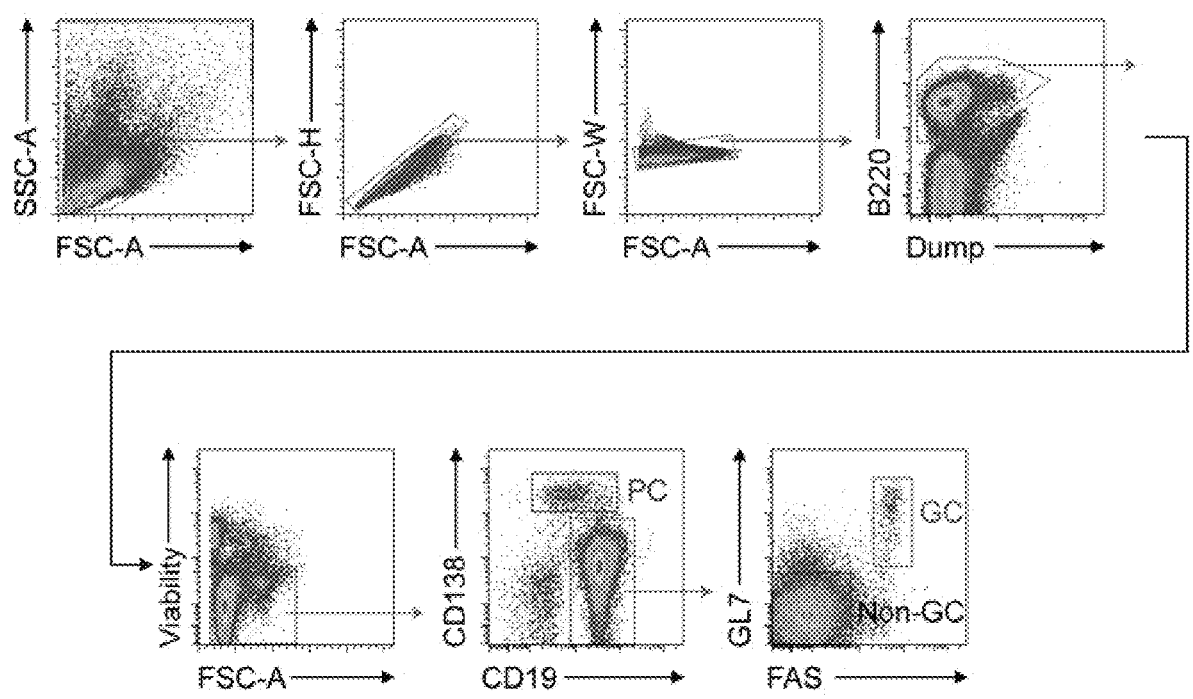

AIRE is essential to central and peripheral T cell tolerance, which consequently regulates humoral immunity. Anderson et al., *Science* 298, 1395-1401, (2002); Gardner et al., *Science* 321, 843-847, (2008); Malchow et al., *Science* 339, 1219-1224, (2013). To determine whether AIRE has a B cell-intrinsic function in humoral immunity, AIRE expression in B cells of human secondary lymphoid tissues was examined by immunofluorescence using an antibody that detects AIRE in the nuclei of thymic medullary epithelial cells (mTECs) (FIG. 1A). IgD$^-$ B cells were identified inside tonsillar and splenic follicles that harbored nuclear AIRE (FIG. 1A, FIGS. 2A-2D). In contrast, tonsillar IgD$^+$ B cells in the mantle zone and IgD$^+$ plasmablasts in GCs and extrafollicular areas (Chen et al., *Nature immunology* 10, 889-898, (2009)) expressed little or no AIRE (FIG. 1A, FIGS. 2A-2D). Peripheral blood IgD$^+$CD27$^-$ or CD24$^+$CD38$^{lo}$ naive, IgD$^+$CD27$^+$ circulating marginal zone, IgD$^-$CD27$^+$ or CD24$^{hi}$CD38$^-$ memory, IgD$^-$CD27$^-$ atypical memory and CD24$^{hi}$CD38$^{hi}$ transitional B cells as well as CD24$^-$CD38$^{hi}$ plasma cells (PCs) did not express AIRE either (FIGS. 2E,2F). Consistent with their follicular localization, tonsillar AIRE$^+$ B cells were mostly IgD$^-$CD38$^+$ GC B cells (FIG. 1B). AIRE expression was similarly found in B cells in the splenic follicles of immunized mice (FIG. 1C).

Figure 1F:
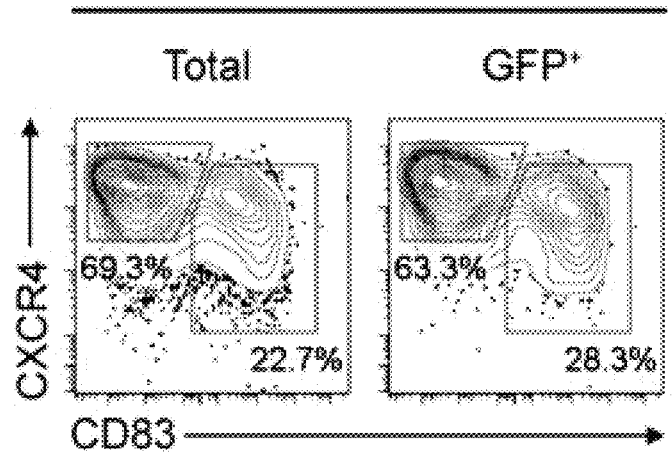

In the Aire$^{Adig}$ reporter mice (Gardner et al., Science 321, 843-847, (2008)), B cell AIRE expression was detected in FAS$^+$GL7$^+$ GC B cells in the spleen, inguinal lymph nodes (ILNs), mesenteric lymph nodes (MLNs) and Peyer's patches (PPs) and in thymic B cells, but not in FAS$^-$GL7$^-$ non-GC B cells or CD138$^+$ PCs in these tissues or in peripheral blood B cells (FIGS. 1D, 1E, FIGS. 2G, 2H), and there was no preferential distribution of AIRE in CXCR4$^+$CD83$^-$ dark zone (DZ) vs. CXCR4$^{lo}$CD83$^+$ light zone (LZ) B cells (FIG. 1F). These data indicate that AIRE expression in GC B cells is a conserved characteristic of human and mouse secondary lymphoid tissues.

Figure 1G:
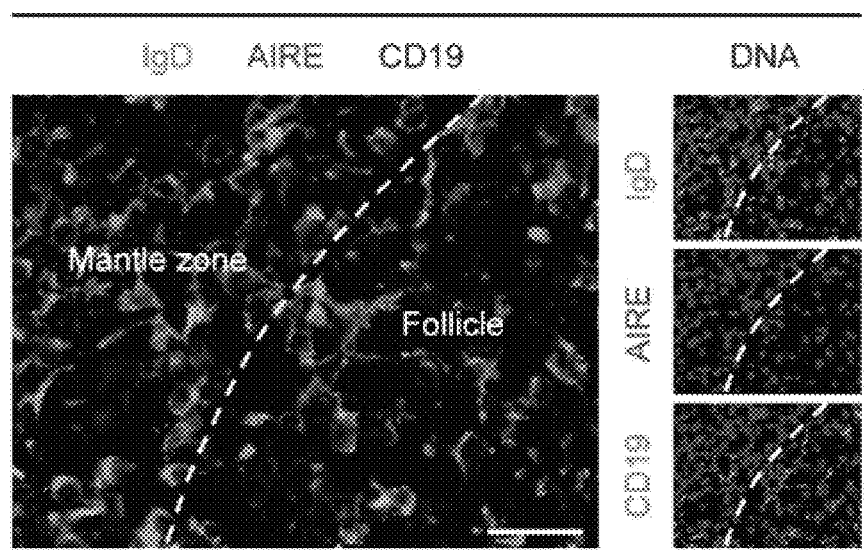
Figure 1H:
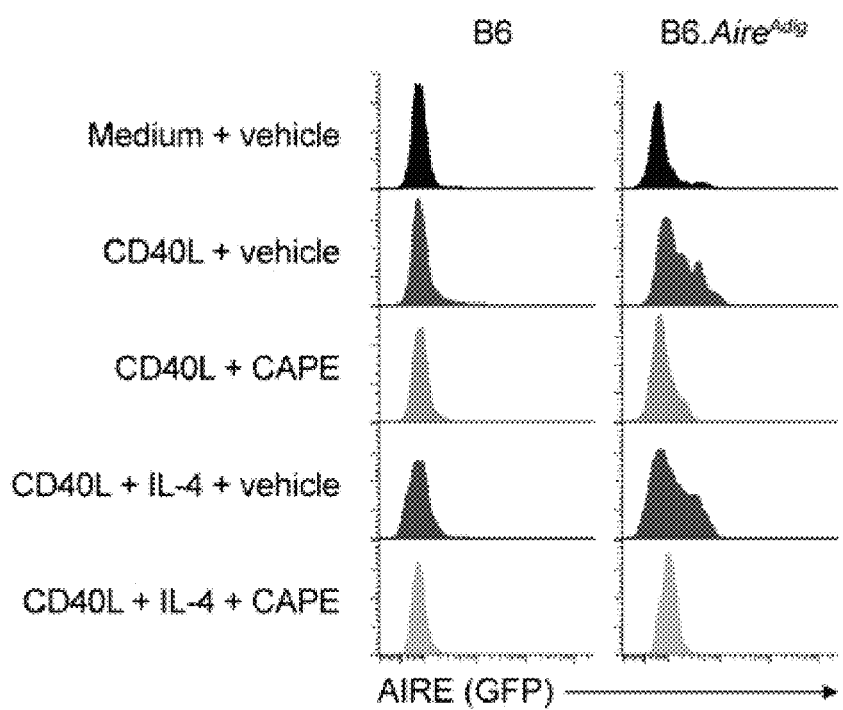
Figure 3A:
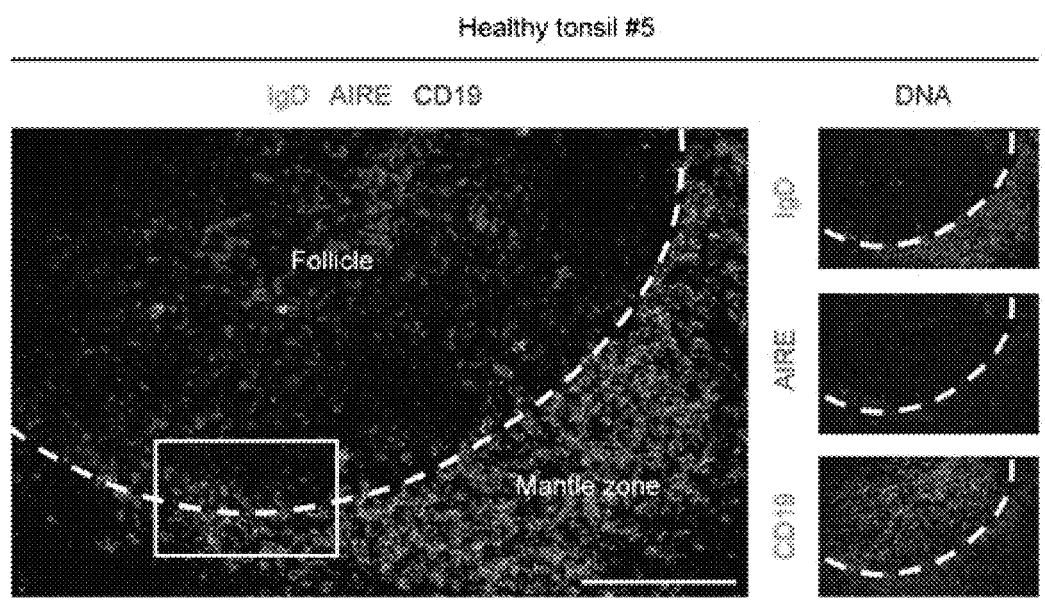
Figure 3B:
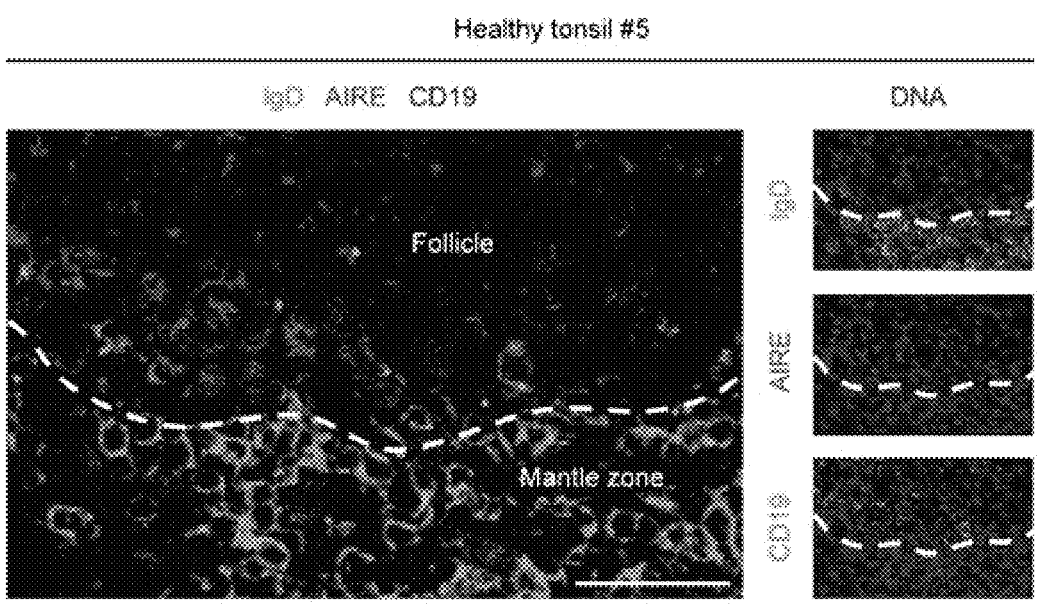
Figure 3D:
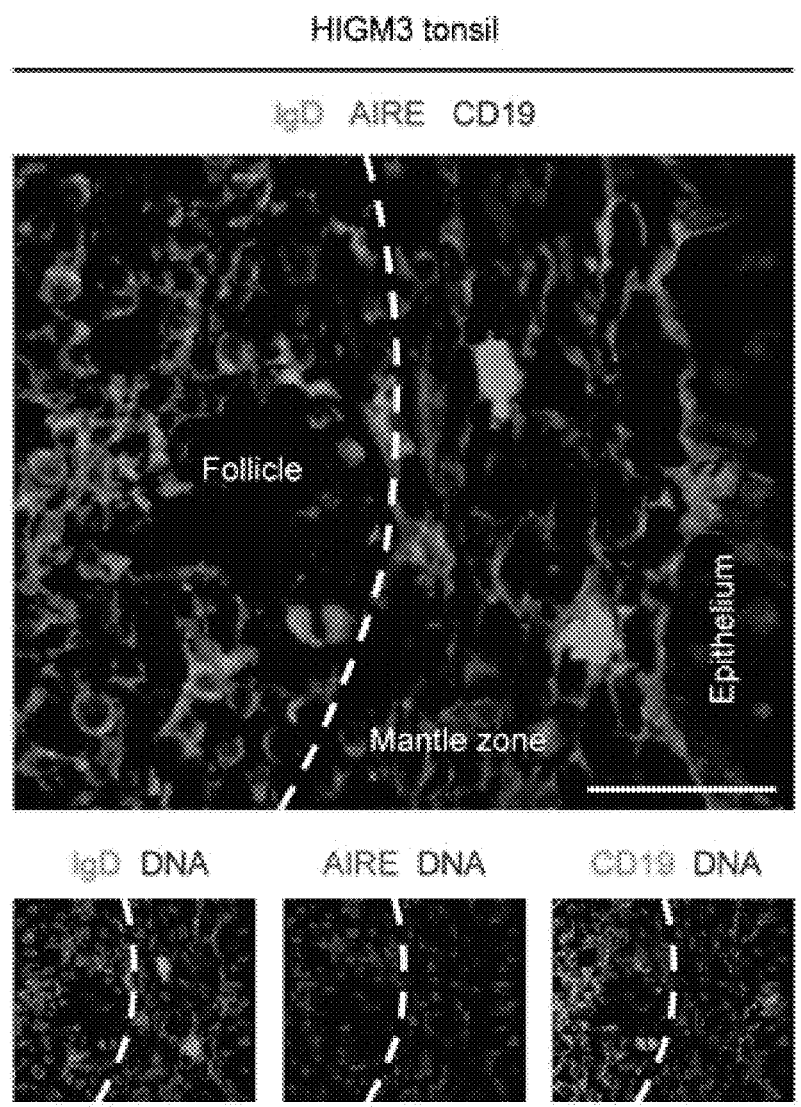
Figure 4A:
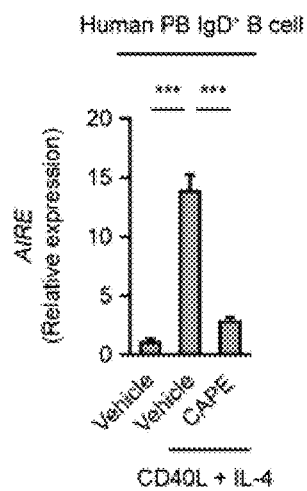
FIGS. 4A-4F. AIRE expression in B cells is induced by CD40 ligation in vitro.
Figure 4B:
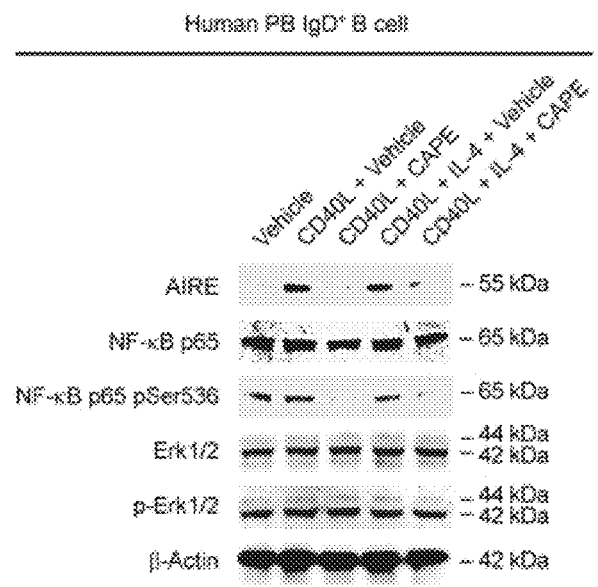
Figure 4C:
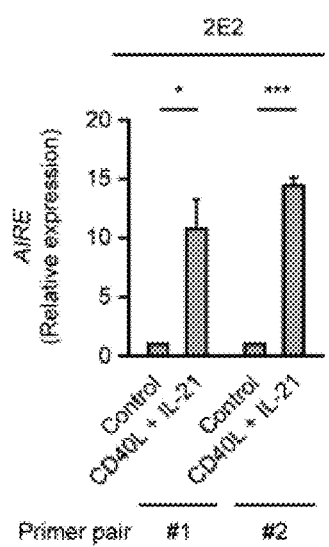
Figure 4D:
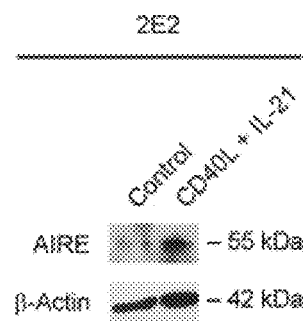
Figure 4E:
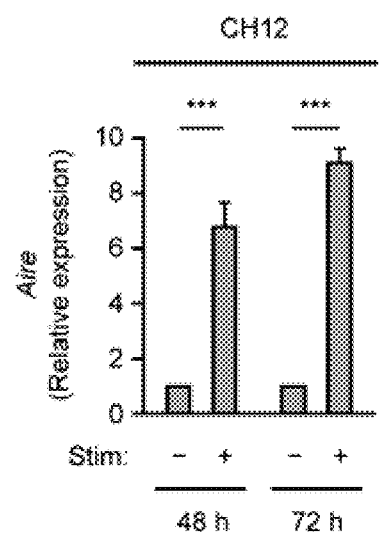
Figure 4F:
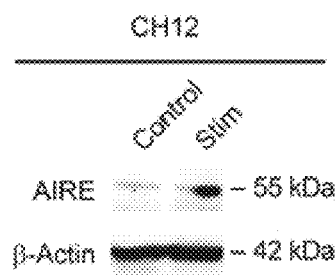

It was further sought to identify the regulation of GC B cell AIRE expression and examined the role of CD40 signalling, which is critical for T cell-dependent GC B cell responses (Liu et al., Nature 342, 929-931, (1989)) and was previously reported to promote AIRE expression by mTECs and thymic B cells. Akiyama et al., Immunity 29, 423-437, (2008); Yamano et al., Immunity 42, 1048-1061, (2015). In contrast to the prominent AIRE expression in tonsillar follicular B cells of healthy subjects (FIG. 1A, FIGS. 2A, 2B, FIGS. 3A, 3B), tonsillar follicular B cells of a patient with the rare primary immunodeficiency hyper-IgM syndrome type 3 (HIGM3), which is caused by loss-of-function mutations in the CD40 gene (Durandy et al., Immunological reviews 203, 67-79, (2005)), did not express AIRE (FIG. 1G, FIGS. 3C, 3D). AIRE mRNA and protein levels were induced in human peripheral blood IgD$^+$ B cells upon stimulation with CD40 ligand (CD40L) alone or with IL-4, which was inhibited by caffeic acid phenethyl ester (CAPE), a selective inhibitor of nuclear factor-kappa B (NF-κB) (Natarajan et al., Proceedings of the National Academy of Sciences of the United States of America 93, 9090-9095, (1996)), the transcription factor activated by CD40 (FIGS. 4A, 4B). Similarly, mouse splenic B cells expressed AIRE upon CD40L stimulation ex vivo, which was abrogated by CAPE (FIG. 1H). In addition, human 2E2 and mouse CH12 cells, two B cell lines that undergo CD40L-induced CSR in vitro, had increased AIRE mRNA and protein expression upon CD40 ligation (FIGS. 4C-4F). Therefore, CD40 signalling is required for AIRE expression in GC B cells in vivo and promotes AIRE expression by B cells in vitro.

Figure 5A:
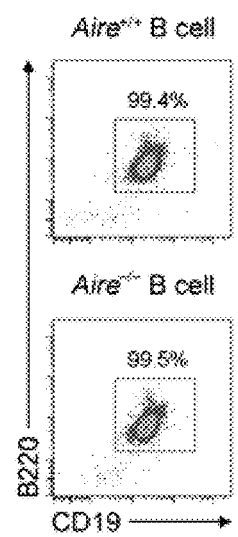
FIGS. 5A-5I. Aire$^{+/+}$ and Aire$^{-/-}$ B cells had a similar phenotype before transfer and entered GC reaction equally in immunised μMT recipients in vivo, and exhibited similar proliferation and apoptosis during ex vivo stimulation.
Figure 5B:
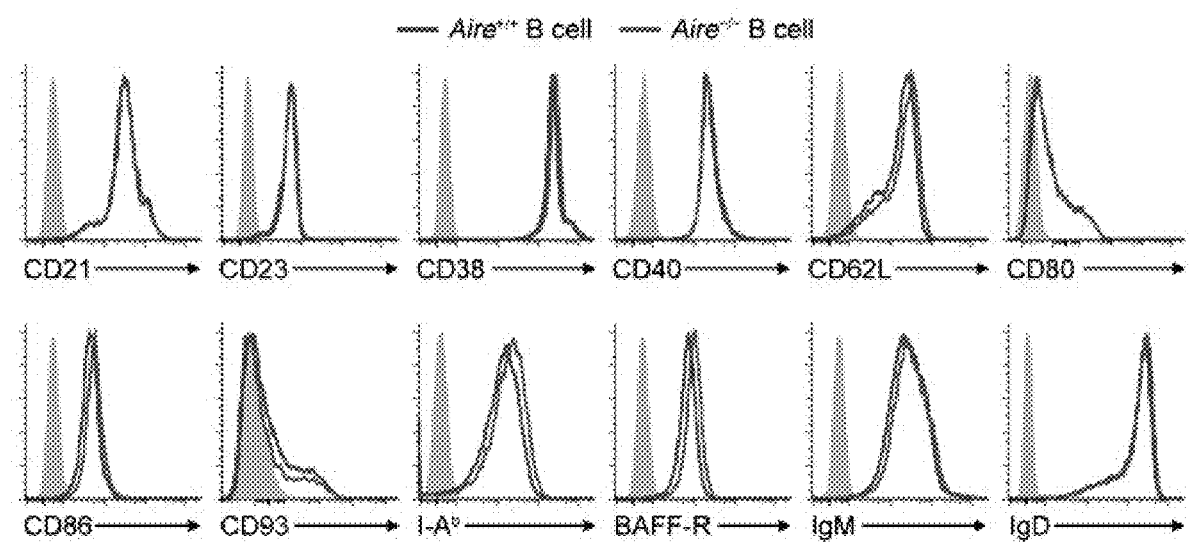
Figure 5C:
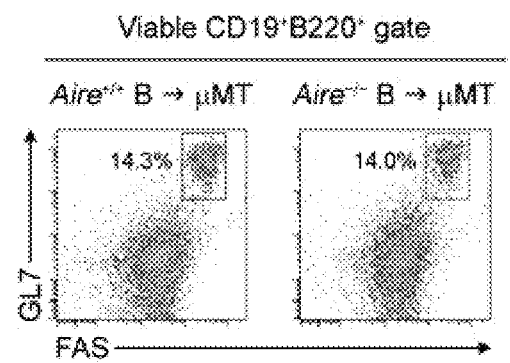
Figure 5D:
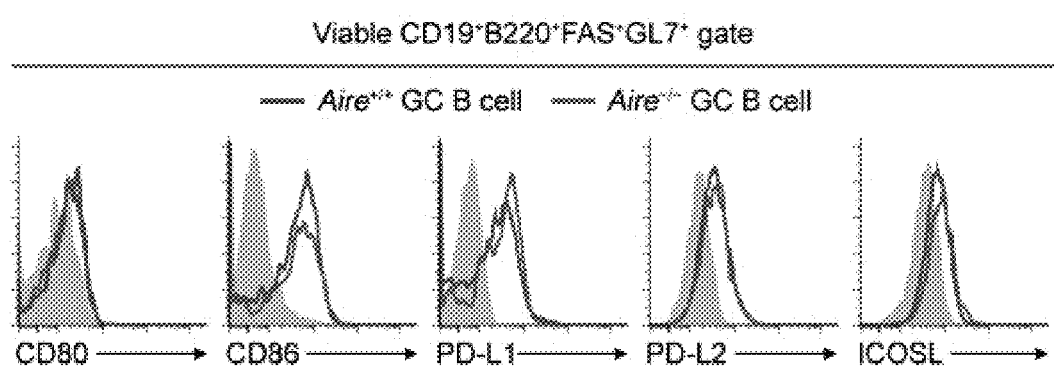
Figure 5E:
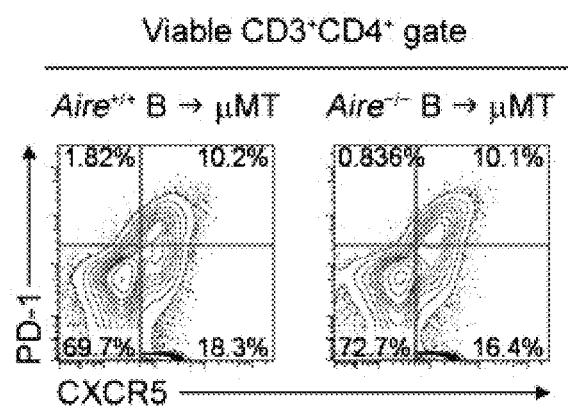
Figure 5F:
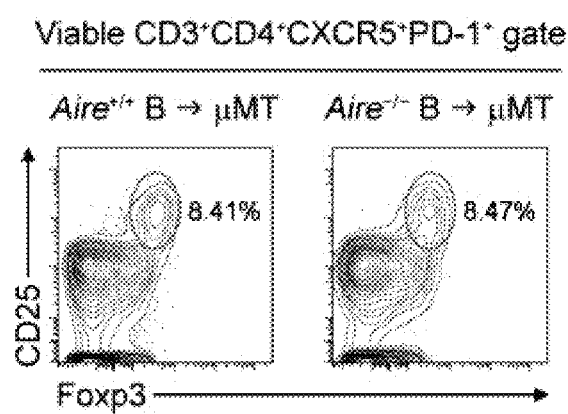

The B cell-deficient μMT recipient mice reconstituted with resting B cells from either Aire$^{+/+}$ or Aire$^{-/-}$ naive donor mice (FIG. 5A) was employed to determine the B cell-intrinsic function of AIRE in antibody response. Before adoptive transfer, Aire$^{+/+}$ and Aire$^{-/-}$ donor B cells exhibited a similar phenotype (FIG. 5B). Following repeated systemic immunization with the T cell-dependent antigen NP$_{32}$-KLH, Aire$^{+/+}$ and Aire$^{-/-}$ donor B cells equally entered the splenic GC compartment (FIG. 5C) and showed similar expression of major co-stimulatory and co-inhibitory molecules (FIG. 5D), but NP-specific Aire$^{-/-}$ donor B cells exhibited elevated CSR by harboring a much higher fraction of IgM$^-$IgD$^-$ cells than NP-specific Aire$^{+/+}$ donor B cells (FIG. 6A), and underwent increased affinity maturation by producing IgG1, IgG2b and IgG3, but not IgM, of higher NP$_4$ to NP$_{29}$ binding ratios (FIG. 6B). Of note, μMT recipients of Aire$^{+/+}$ and Aire$^{-/-}$ B cells had a similar proportion of CXCR5$^+$PD-1$^+$ follicular helper T (T$_{FH}$) cells (FIG. 5E) and Foxp3$^+$CD25$^+$ follicular regulatory T (T$_{FR}$) cells in the spleen (FIG. 5F). These results suggest that AIRE inhibits antibody CSR and SHM in a GC B cell-intrinsic manner.

Figure 5G:
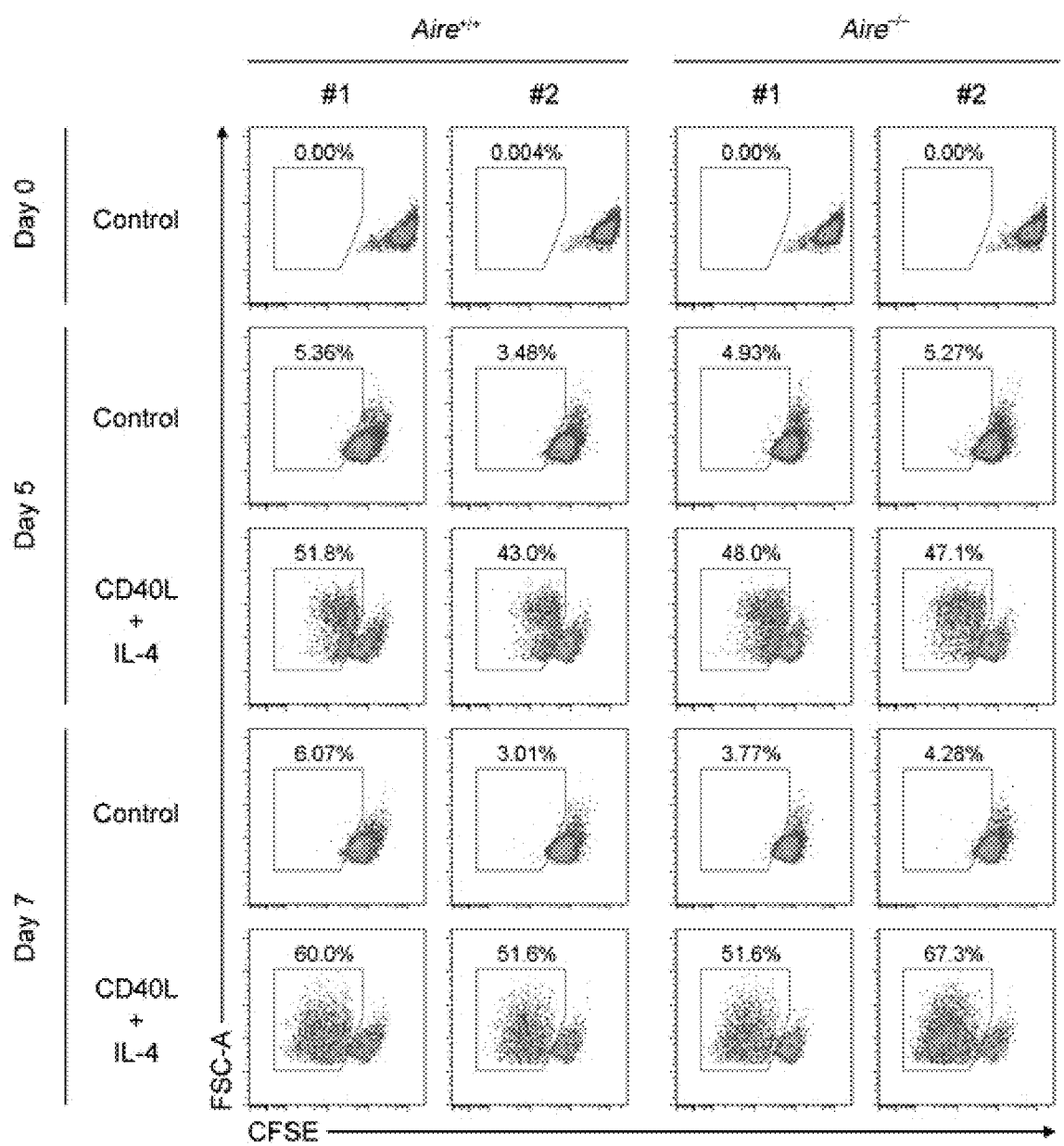
Figure 5H:
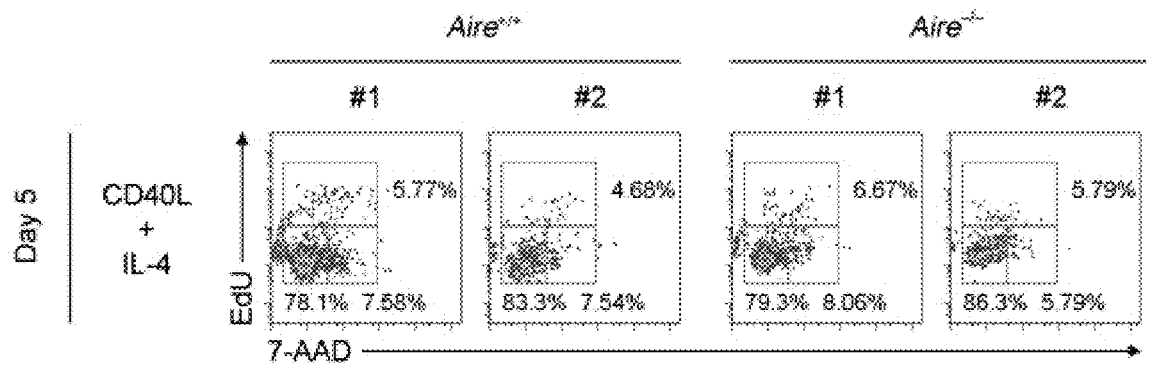
Figure 5I:
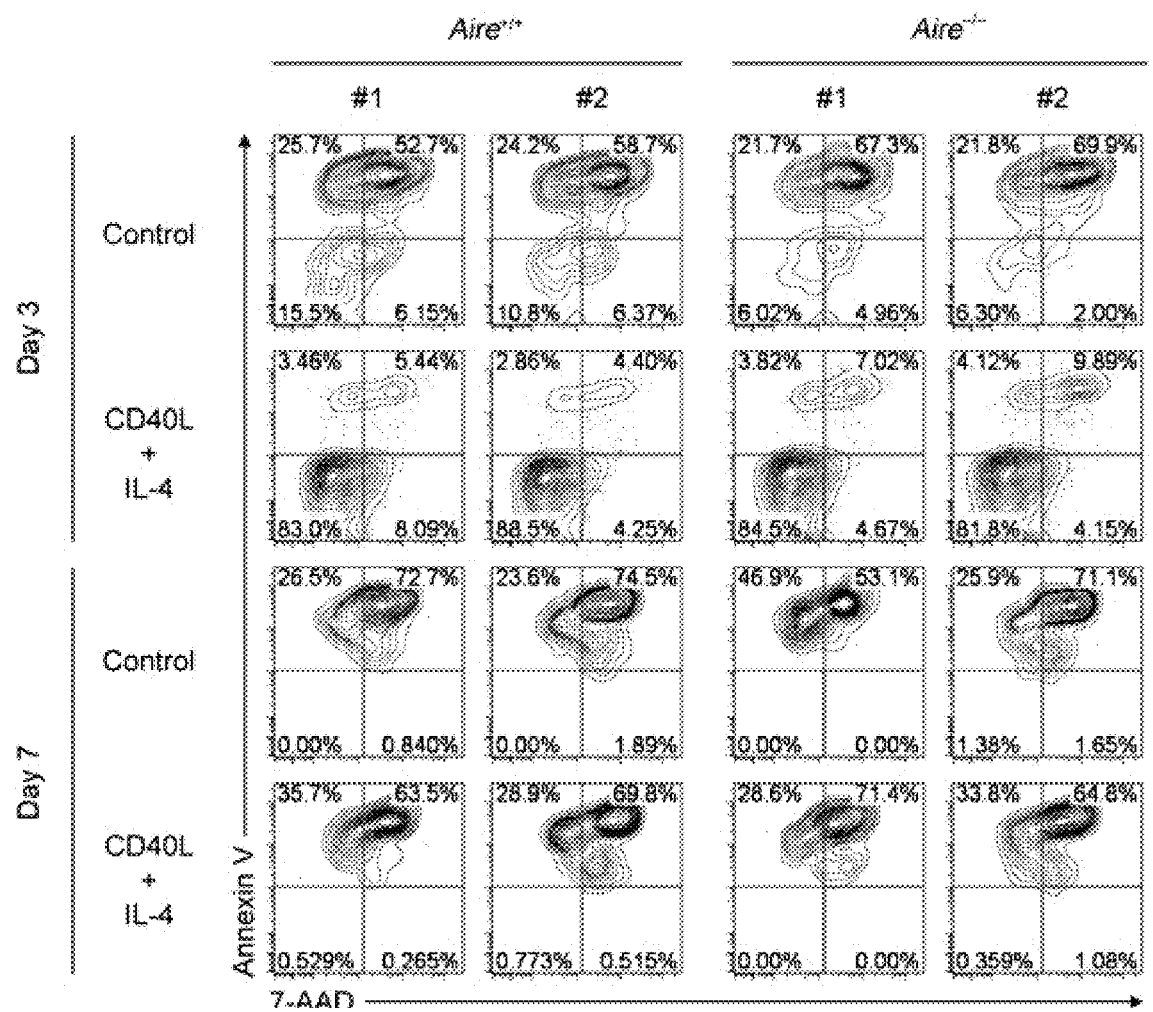
Figure 6D:
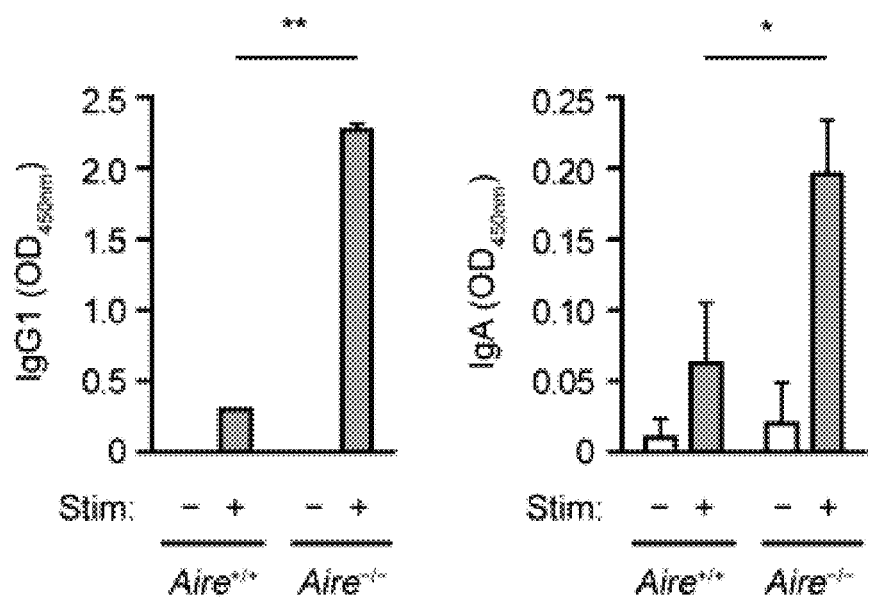
Figure 6E:
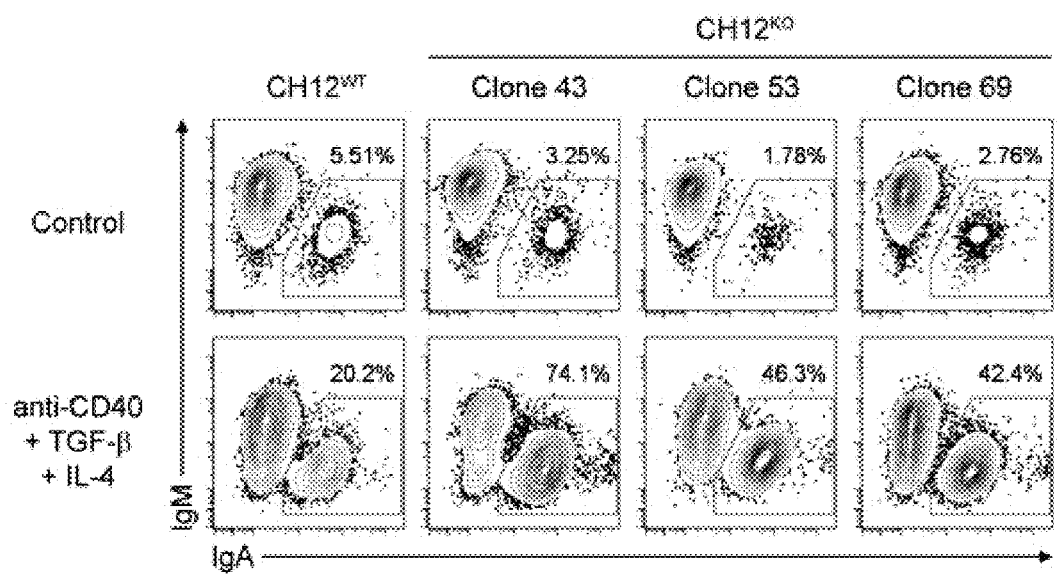
Figure 6F:
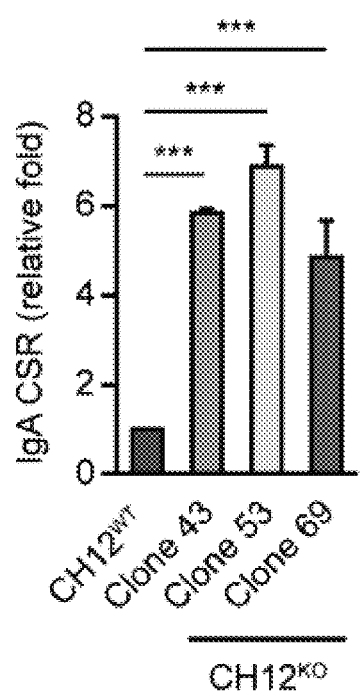
Figure 6G:
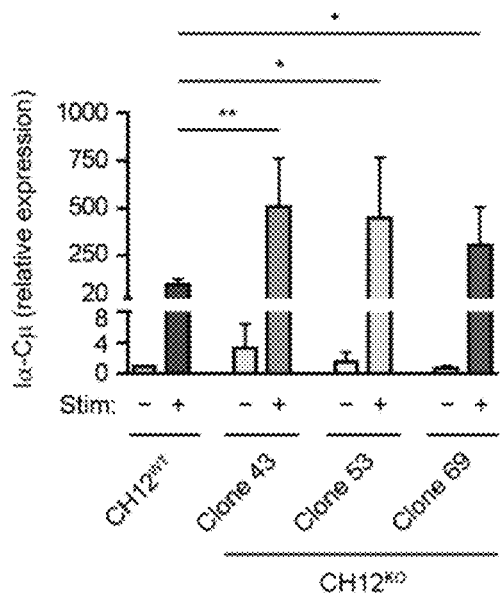
Figure 6H:
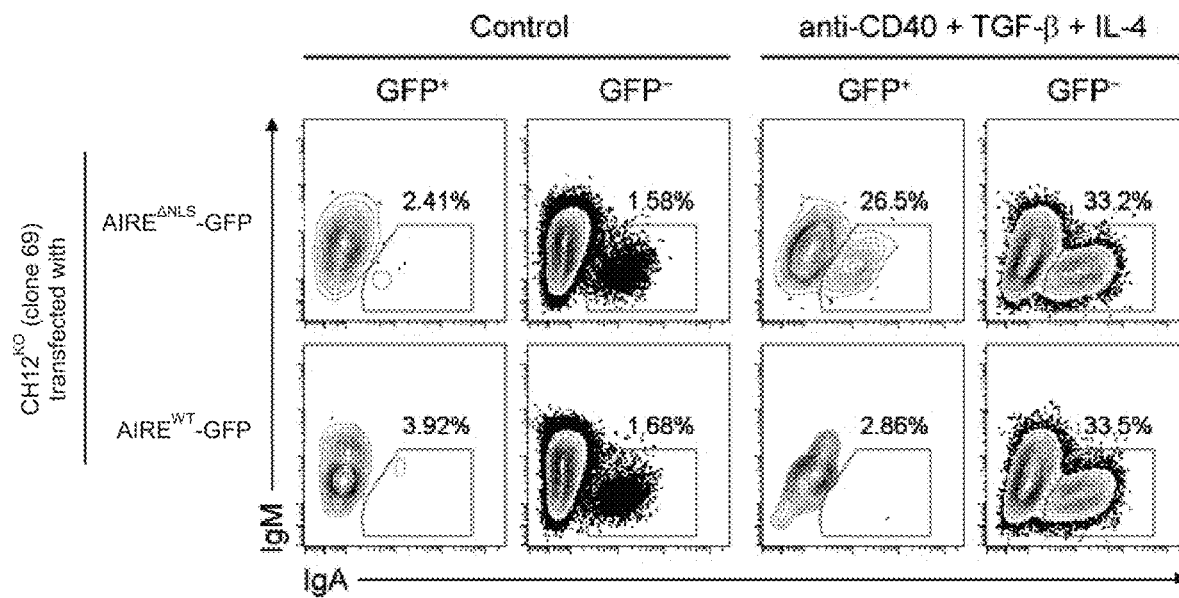
Figure 7A:
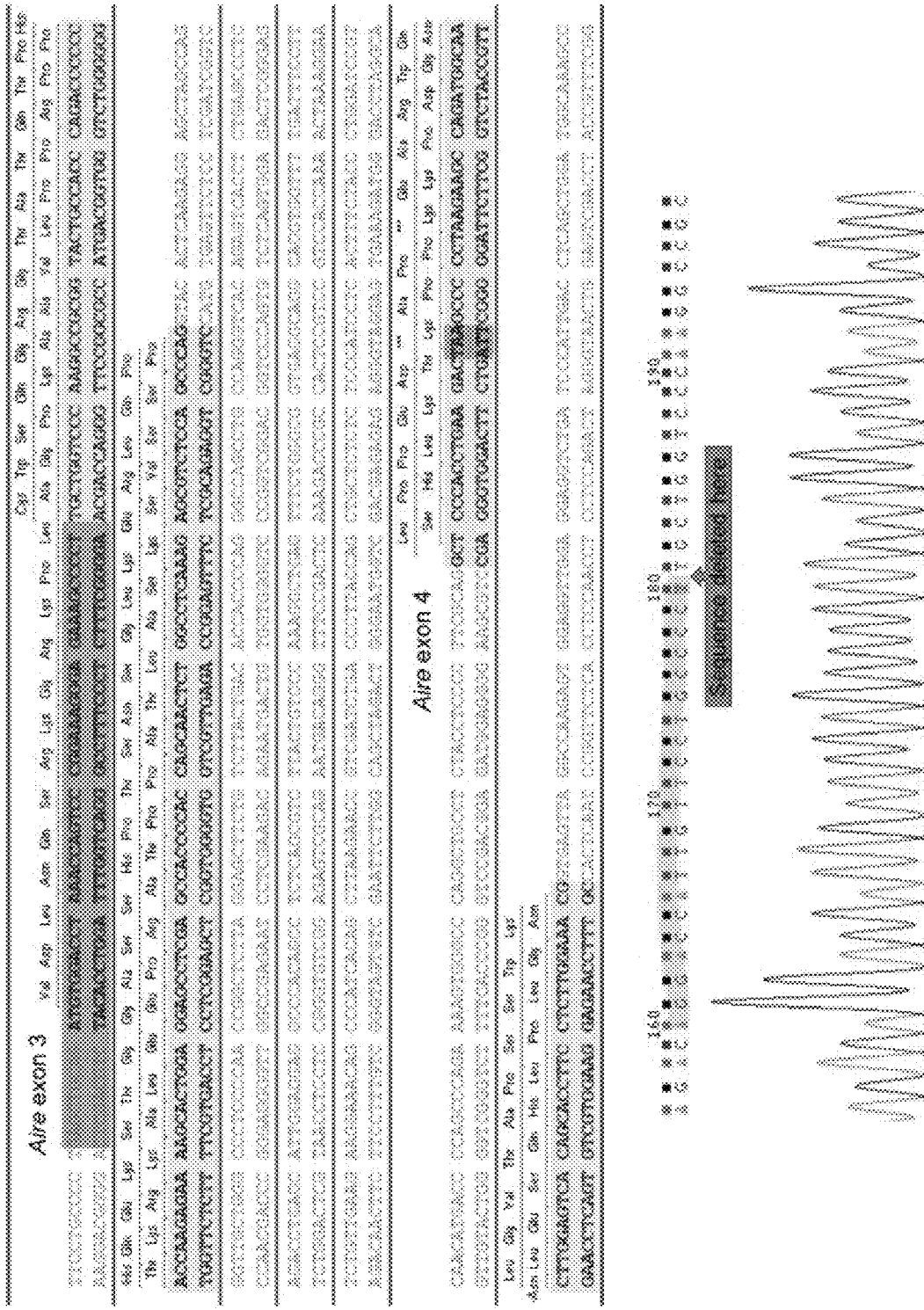
FIGS. 7A-7F. Validation of Aire$^{-/-}$ CH12 cell clones.
Figure 7B:
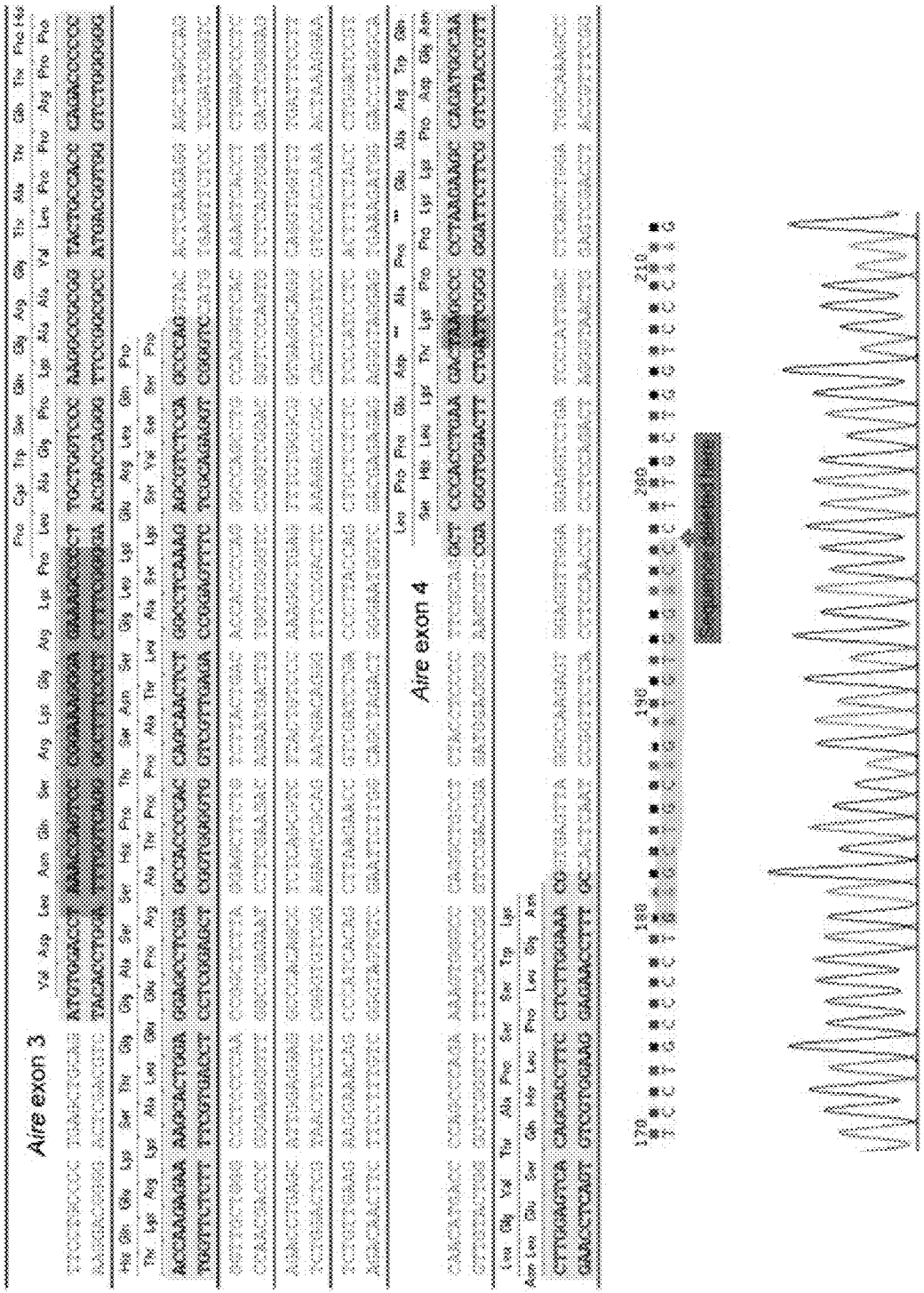
Figure 7B:
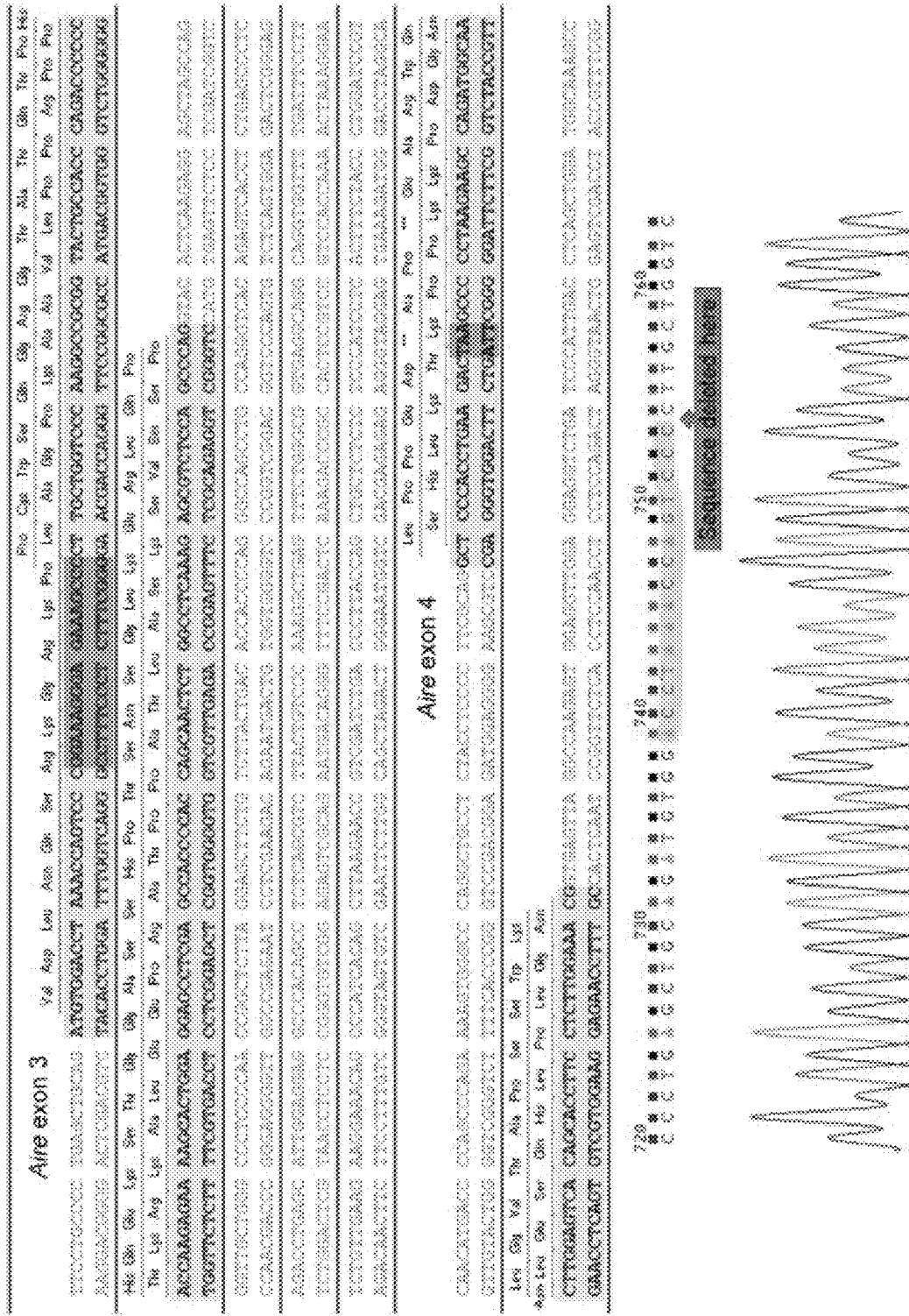
Figure 7C:
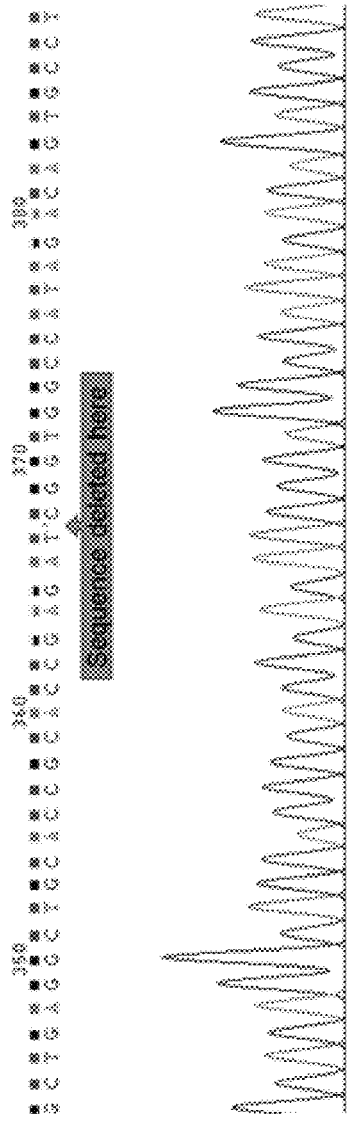
Figure 7D:
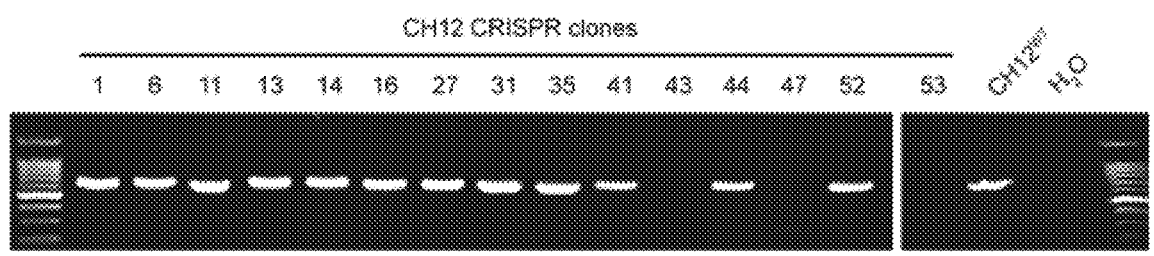
Figure 7E:
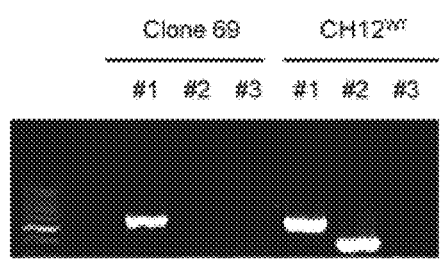
Figure 7F:
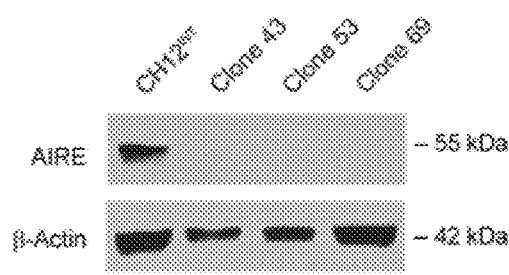
Figure 8A:
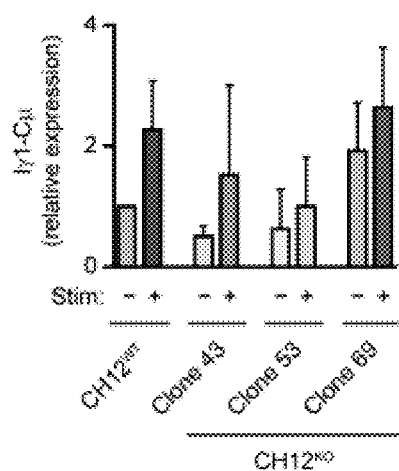
FIGS. 8A-8F. AIRE deficiency does not affect the expression of AID or germline transcripts in CH12 cells.
Figure 8B:
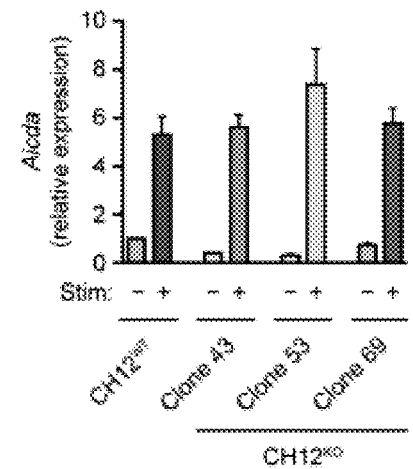
Figure 8C:
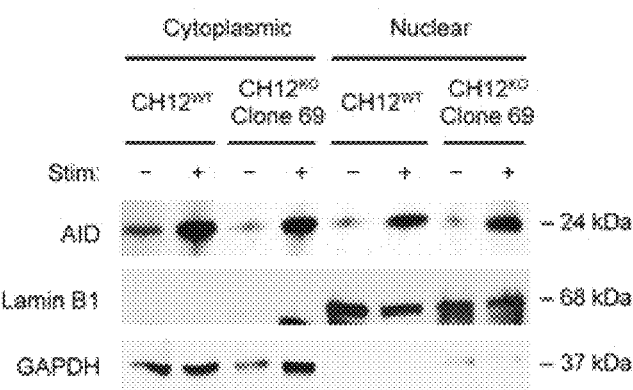
Figure 8D:
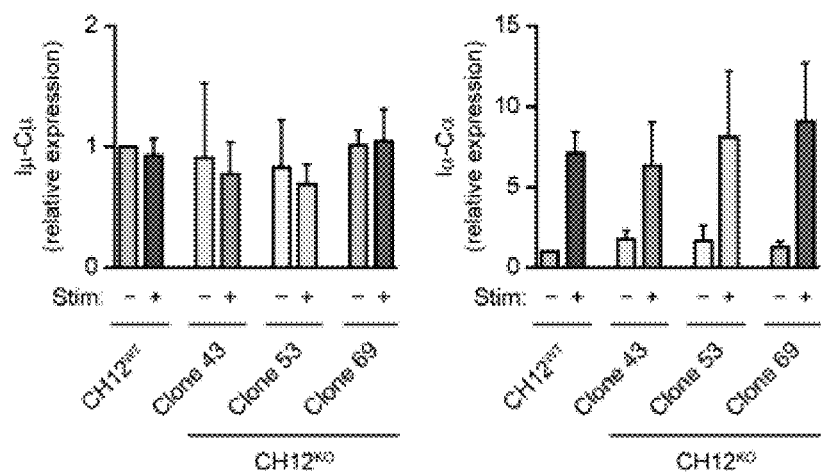
Figure 8E:
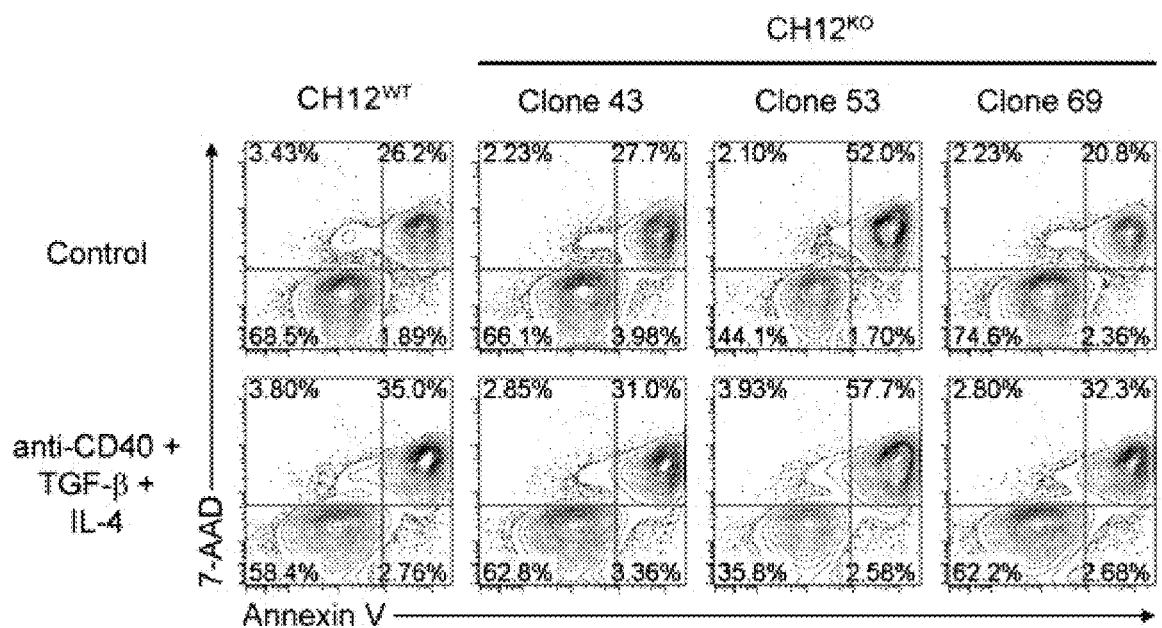
Figure 8F:
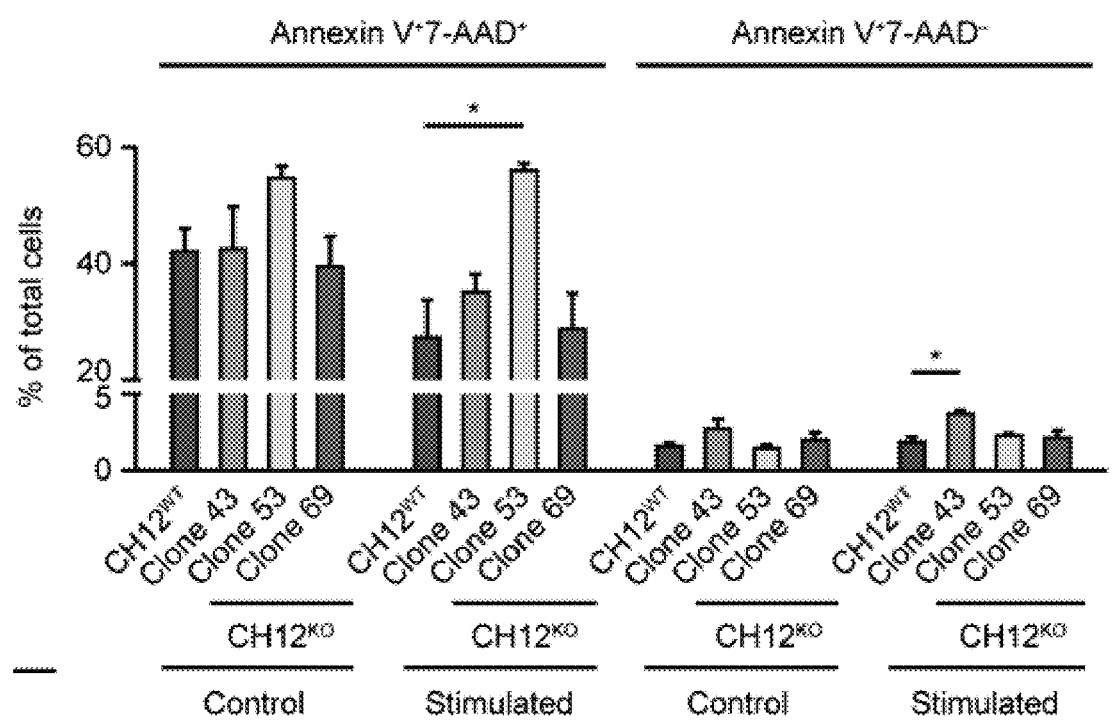

To verify the B cell-intrinsic inhibitory function of AIRE in CSR, splenic B cells of naïve Aire$^{+/+}$ and Aire$^{-/-}$ mice were compared for their ability to undergo CSR ex vivo. Aire$^{-/-}$ B cells underwent increased CSR (FIG. 6C) and secreted more class-switched antibodies upon stimulation in culture (FIG. 6D). The enhanced CSR of and antibody production by Aire$^{-/-}$ B cells were not caused by altered proliferation or apoptosis ex vivo (FIGS. 5G-5I). Using CRISPR-mediated gene editing, the Aire gene was disrupted in CH12 cells, a mouse B cell line that class-switches from IgM to IgA upon stimulation with anti-CD40, TGF-β and IL-4 (Nakamura et al., International immunology 8, 193-201, (1996)), and identified 3 Aire$^{-/-}$ CH12 clones which were frame-shifted in both Aire alleles (FIGS. 7A-7E), devoid of AIRE protein expression (FIG. 7F) and intact at CRISPR off-target sites (not shown). Upon stimulation, these Aire$^{-/-}$ CH12 clones underwent elevated IgA CSR (FIGS. 6E, 6F) with concomitantly increased levels of the Iα-Cμ (FIG. 6G) but not Iγ1-Cμ circle transcript (FIG. 8A) compared to their parental Aire$^{+/+}$ CH12 cells. Exaggerated IgA CSR in Aire$^{-/-}$ CH12 cells was not a result of increased induction of the CSR-mediating enzyme activation-induced cytidine deaminase (AID) (FIGS. 8B, 8C) or germline transcription (FIG. 8D), nor a result of increased survival (FIGS. 8E, 8F). Remarkably, WT AIRE, but not a nuclear localization signal (NLS) deletion mutant AIRE (AIRE$^{ΔNLS}$), suppressed cytokine-induced CSR when re-introduced into Aire$^{-/-}$ CH12 cells (FIG. 6H). These results reaffirm the B-cell intrinsic function of AIRE in inhibiting CSR.

Figure 9A:
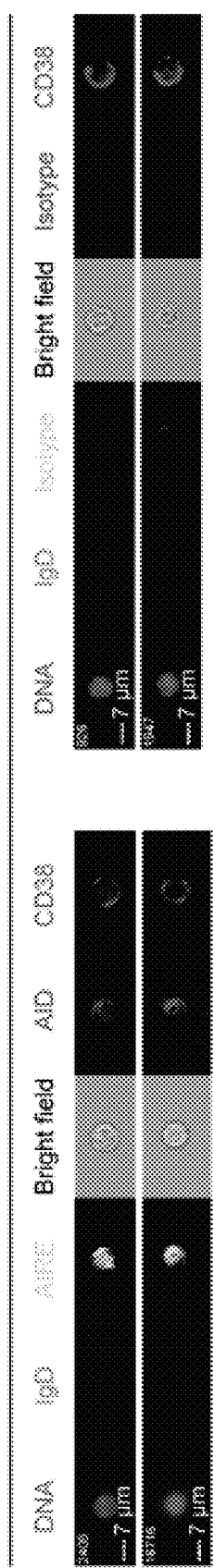
FIGS. 9A-9J. AIRE interacts with AID in GC B cells and inhibits AID activity by reducing AID targeting to Ig S region and stalled Pol II.
Figure 9B:
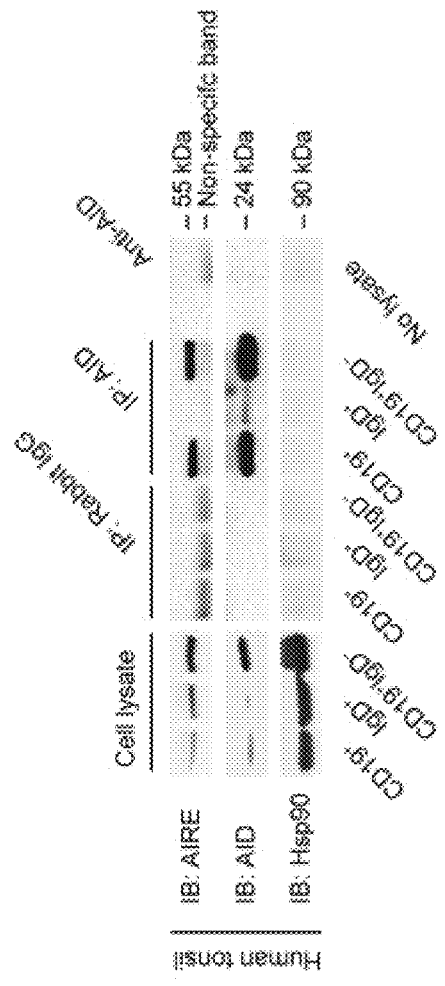
Figure 9C:
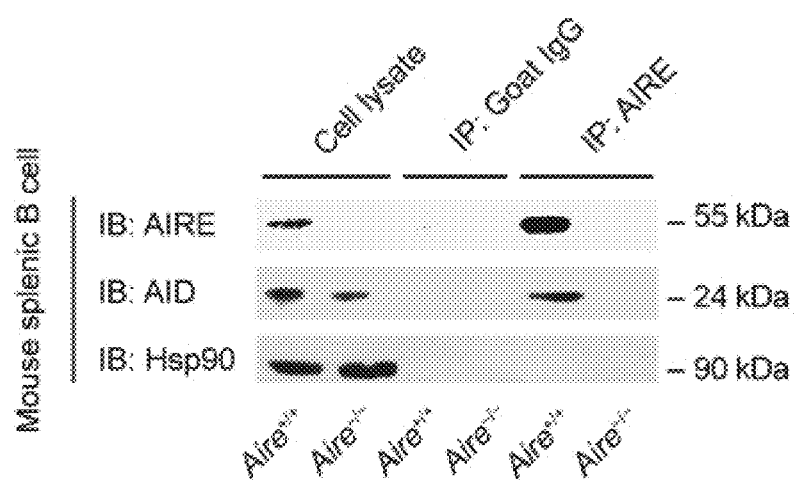
Figure 10A:
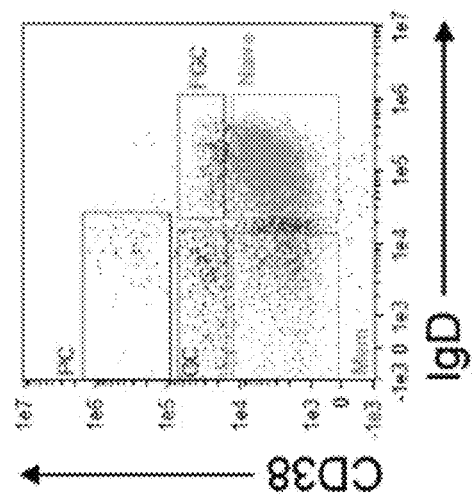
Figure 10B:
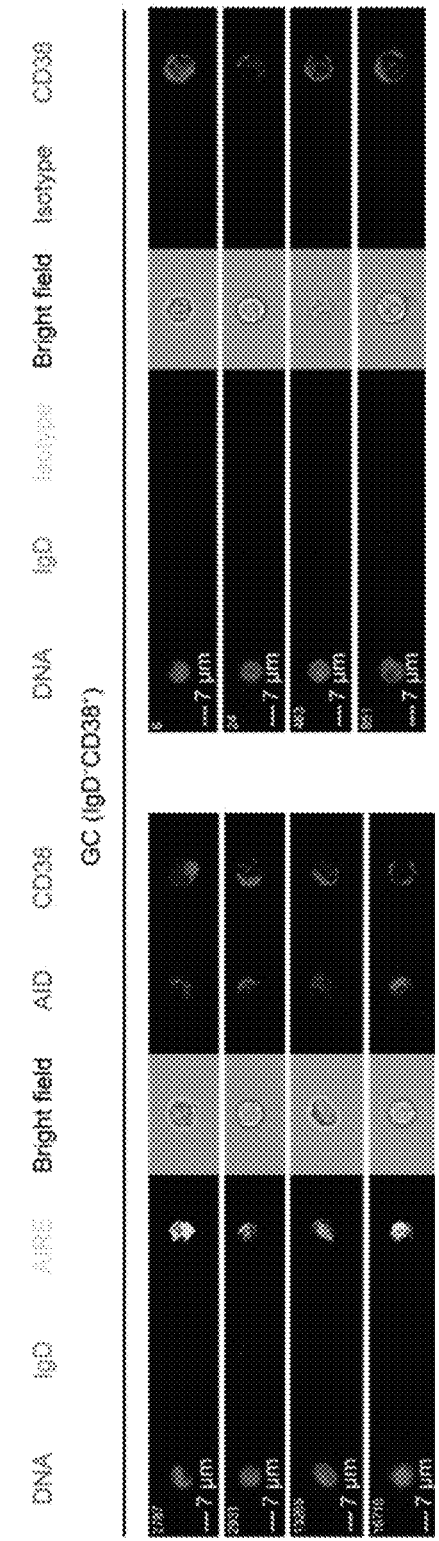
Figure 10E:
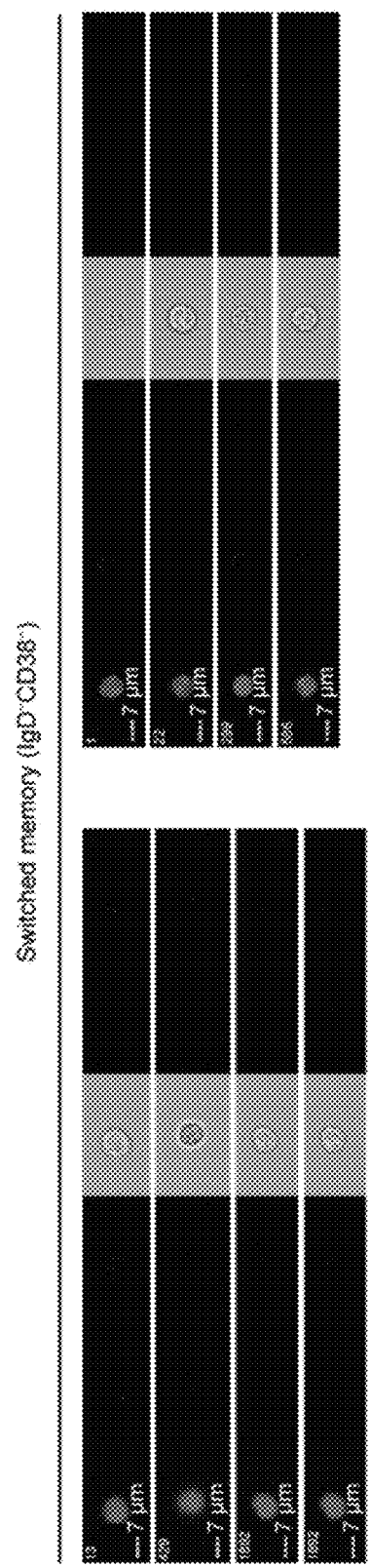
Figure 10F:
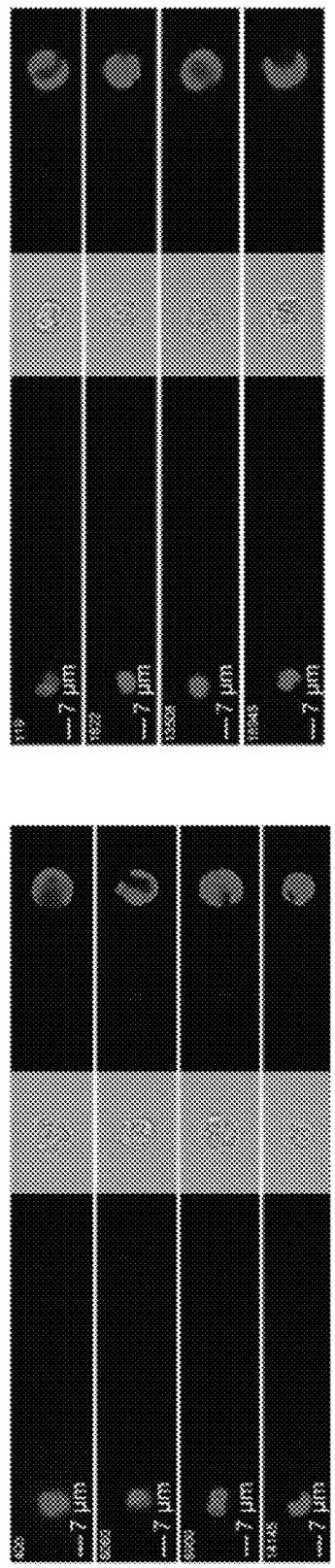
Figure 11A:
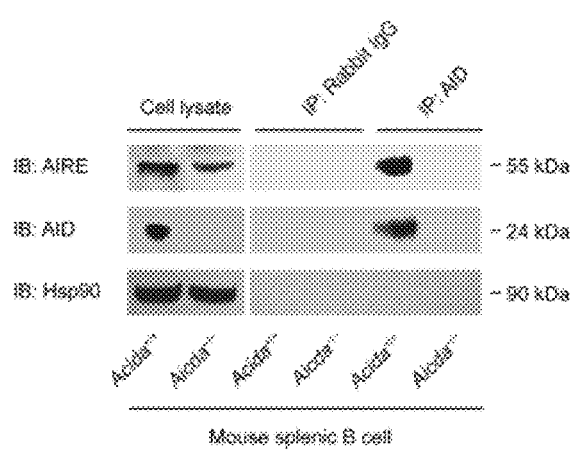
FIGS. 11A-11E. AIRE interacts with AID but not Bcl10 in B cells, and inhibits AID activity.

As AID is the obligatory enzyme that mediates CSR and SHM (Muramatsu et al., Cell 102, 553-563, (2000)), whether AIRE inhibits AID activity in B cells was examined. AIRE and AID co-localized in the nuclei of tonsillar IgD$^-$CD38$^+$ GC B cells (FIG. 9A, FIGS. 10A, 10B) but not in IgD$^+$CD38$^-$ naive B cells, IgD$^-$CD38$^-$ switched memory B cells or IgD$^-$CD38$^{hi}$ switched plasma cells (PCs), albeit a low level of nuclear AIRE and AID were detected in a small fraction of IgD$^+$CD38$^+$ founder GC (FGC) B cells (FIGS. 10C-10F). Using an AID antibody validated for immuno-precipitation (IP) and Chromatin IP (ChIP) (Vuong et al., Nature immunology 10, 420-426, (2009)), it was found that AIRE interacted with AID in human tonsillar CD19$^+$ and CD19$^+$IgD$^-$ cell fractions (FIG. 9B). AIRE also co-immunoprecipitated with AID in splenic B cells of immunized WT but not Aire$^{-/-}$ or Aicda$^{-/-}$ mice (FIG. 9C, FIG. 11A). These data collectively demonstrate that AIRE interacts with AID in GC B cells in vivo and in B cell lines undergoing Ig diversification in vitro.

Figure 9D:
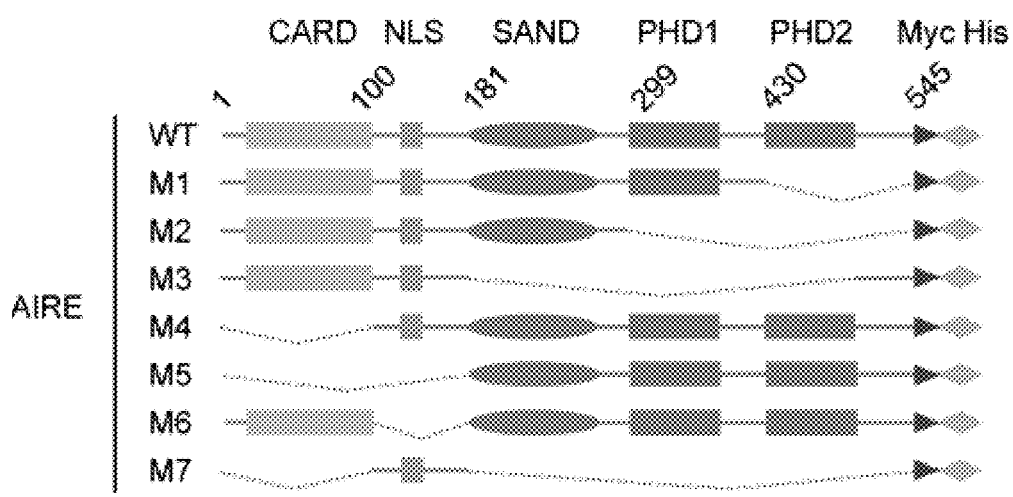
Figure 9E:
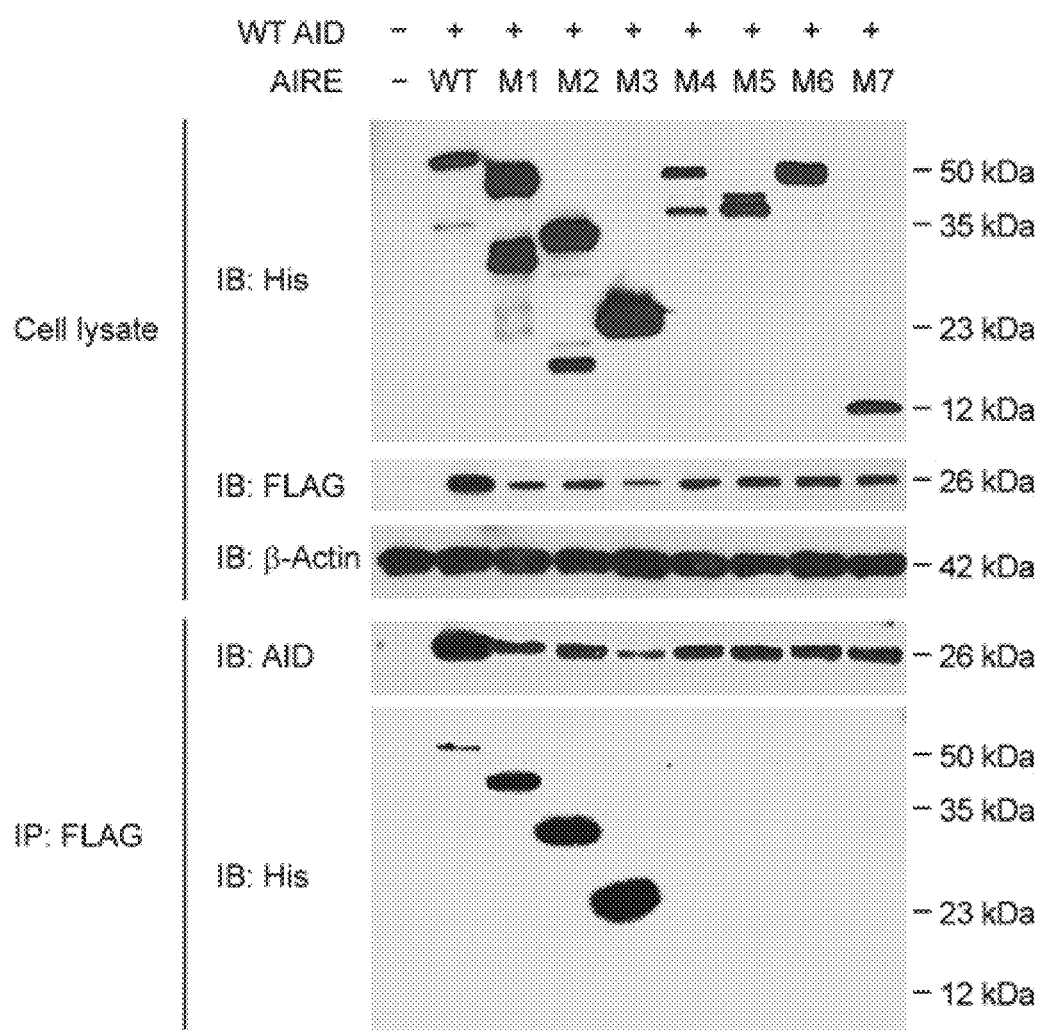
Figure 9F:
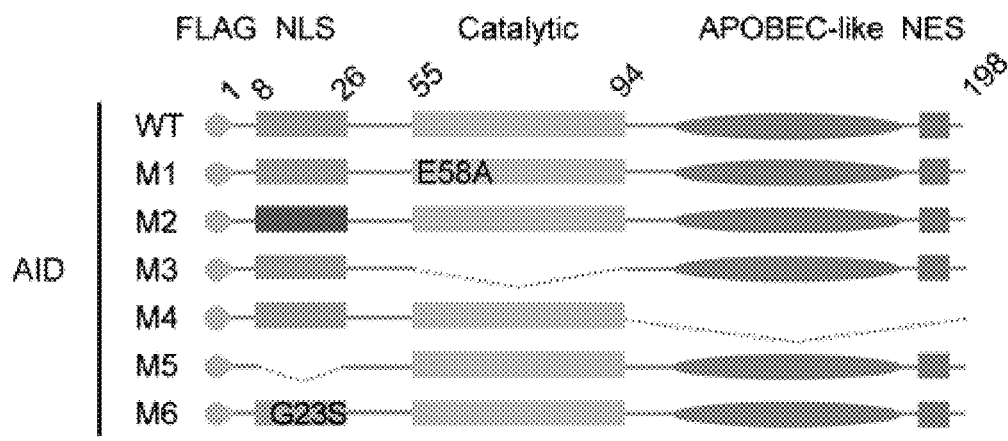
Figure 9G:
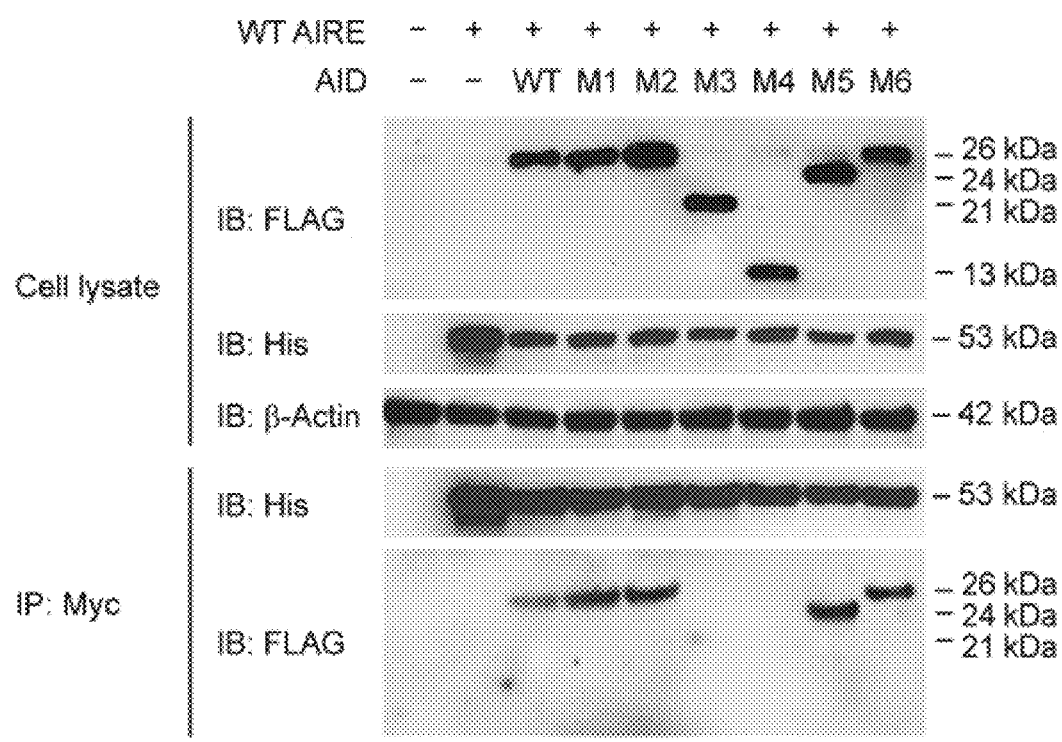
Figure 11B:
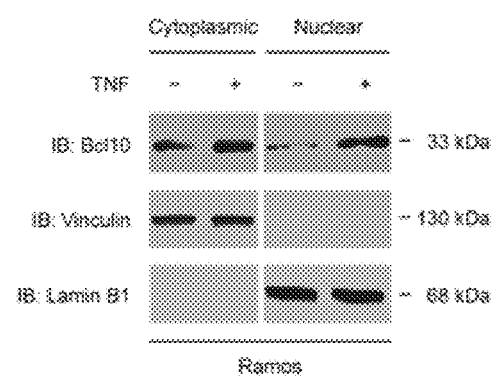
Figure 11C:
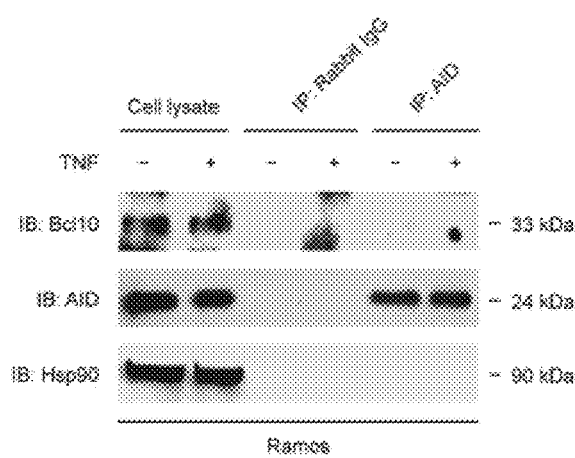

A series of deletion mutants of AIRE with C-terminal Myc and His tags were subsequently generated to characterize its interaction with AID (FIG. 9D, FIG. 12A). AIRE mutants missing the N-terminal caspase activation and recruitment domain (CARD) and/or nuclear localization signal (NLS) lost the ability to interact with AID (FIG. 9E), which demonstrates a requirement for the CARD and NLS of AIRE for interaction with AID and echoes the earlier result showing the dependence for NLS of AIRE in inhibiting CSR in CH12 cells (FIG. 6H). The CARD-dependent interaction with AID was specific to AIRE, as another CARD-containing protein, Bcl10, which undergoes TNF-induced nuclear translocation (Yeh et al., J Biol Chem 281, 167-175, (2006)) (FIG. 11B), did not interact with AID in the human Ramos B cell line which undergoes constitutive Ig diversification in culture (Sale & Neuberger, Immunity, 9, 859-869 (1998)) (FIG. 11C). Furthermore, using a series of deletion, domain replacement or point mutants of AID with an N-terminal FLAG tag (FIG. 9F, FIG. 12B), it was found that the interaction between AID and AIRE required both the catalytic and APOBEC-like domains of AID, although the catalytic activity of AID was not necessary, as the catalytically inactive AID$^{E58A}$ mutant (Patenaude et al., *Nat Struct Mol Biol* 16, 517-527, (2009)) still interacted with AIRE (FIG. 9G). The AID mutation G23S, which substantially abrogates SHM but not much CSR activity (Wei et al., *Nature immunology* 12, 264-270, (2011)), did not affect the interaction with AIRE (FIG. 9G).

Figure 9H:
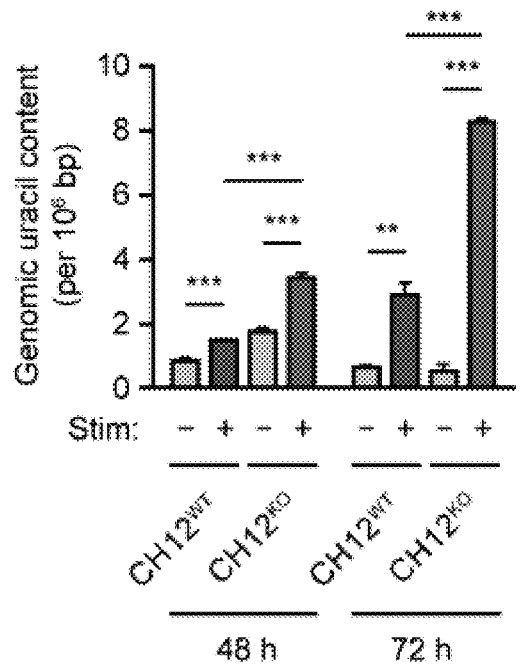
Figure 9I:
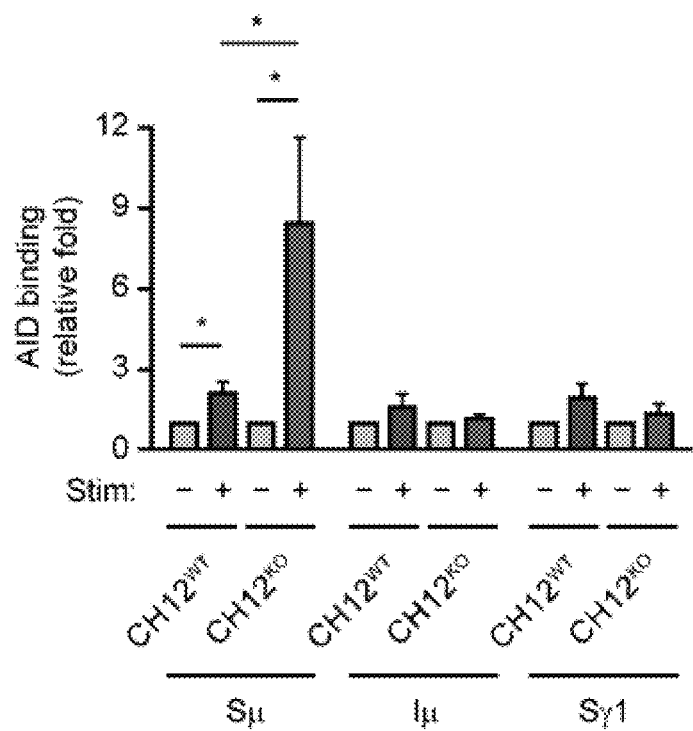
Figure 9J:
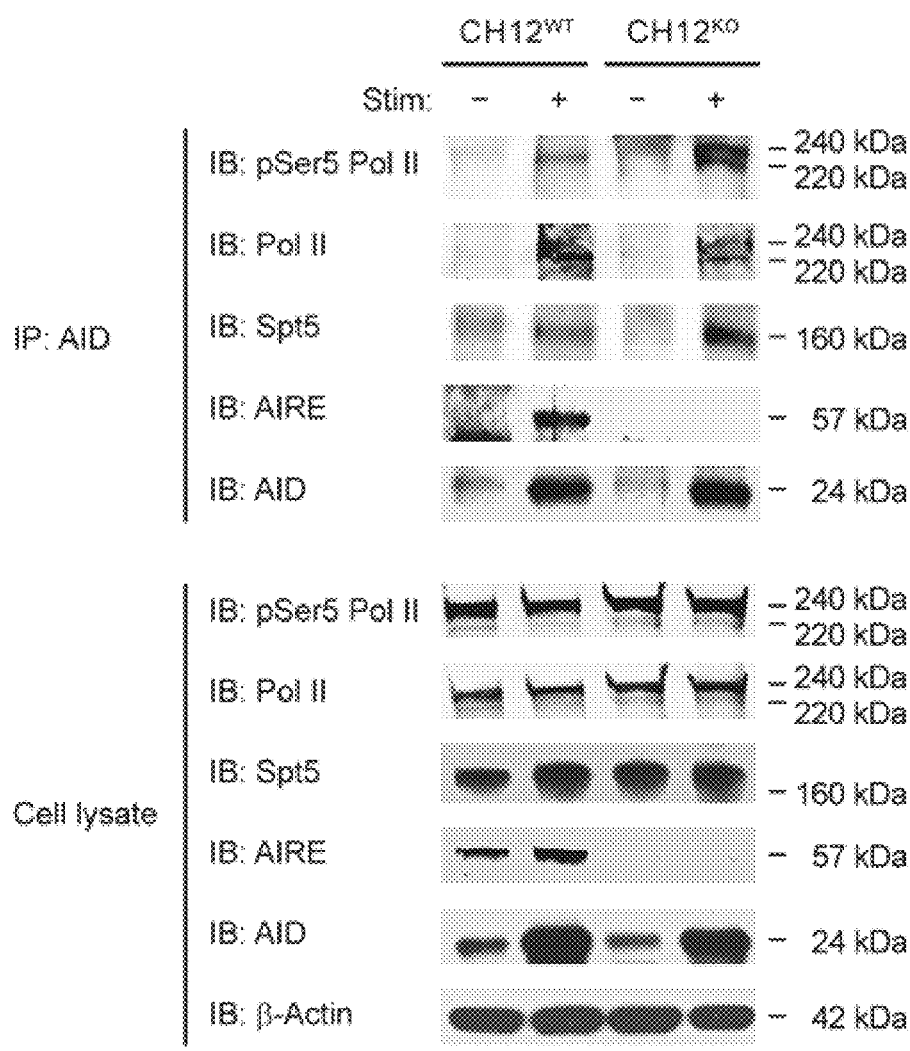
Figure 11D:
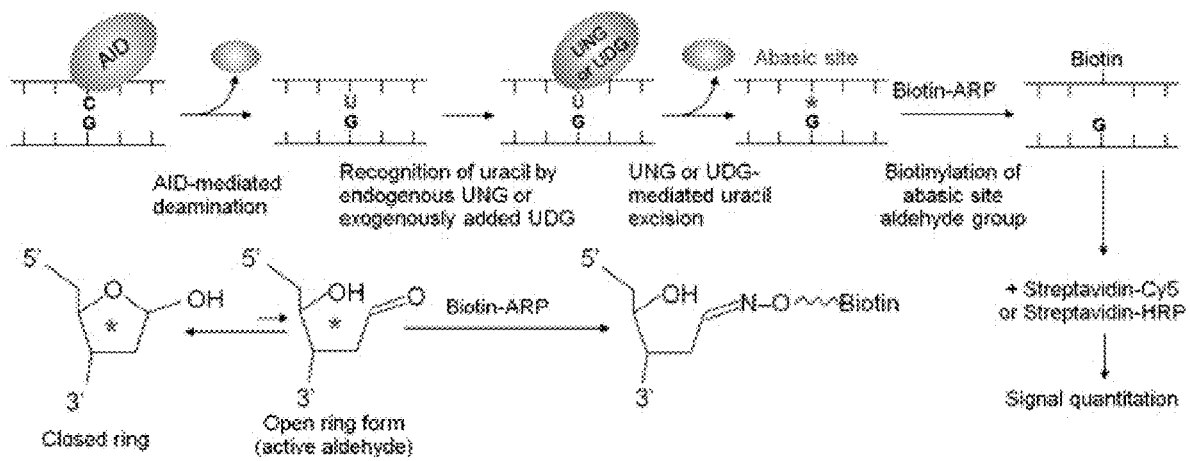
Figure 11E:
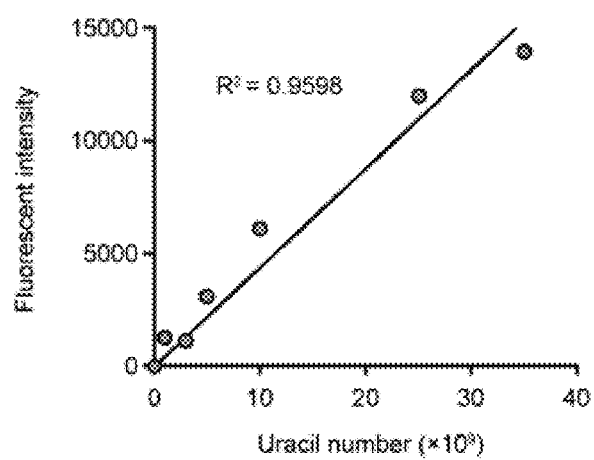

A genomic uracil dot blot assay was then employed to directly test the effect of AIRE on the activity of AID (FIGS. 11D, 11E). Upon stimulation to undergo CSR, Aire$^{-/-}$ CH12 cells harbored higher numbers of genomic uracil than Aire$^{+/+}$ CH12 cells (FIG. 9H), reflecting an inhibitory role of AIRE in AID's deaminase activity. Maul et al., *Nature immunology* 12, 70-76, (2011). Considering that the function of AID requires its proper targeting to the Ig heavy chain (IgH) switch (S) regions at sites of Pol II stalling (Pavri et al., *Cell* 143, 122-133, (2010)), increased AID binding to the Sµ but not Iµ or Sγ1 region (FIG. 9I) and increased AID interaction with transcriptionally stalled (Ser5) Pol II and its associated factor Spt5 (Peterlin & Price, *Molecular cell* 23, 297-305, (2006)) in stimulated Aire$^{-/-}$ CH12 cells compared to stimulated Aire$^{+/+}$ CH12 cells (FIG. 9J) were found. These data are consistent with a function of AIRE in unleashing stalled Pol II by recruiting the positive transcription elongation factor b (P-TEFb) complex (Oven et al., *Mol Cell Biol* 27, 8815-8823, (2007)), and suggest that AIRE inhibits AID function by promoting Pol II escape from stalling and reducing AID targeting to its DNA substrate.

Figure 13A:
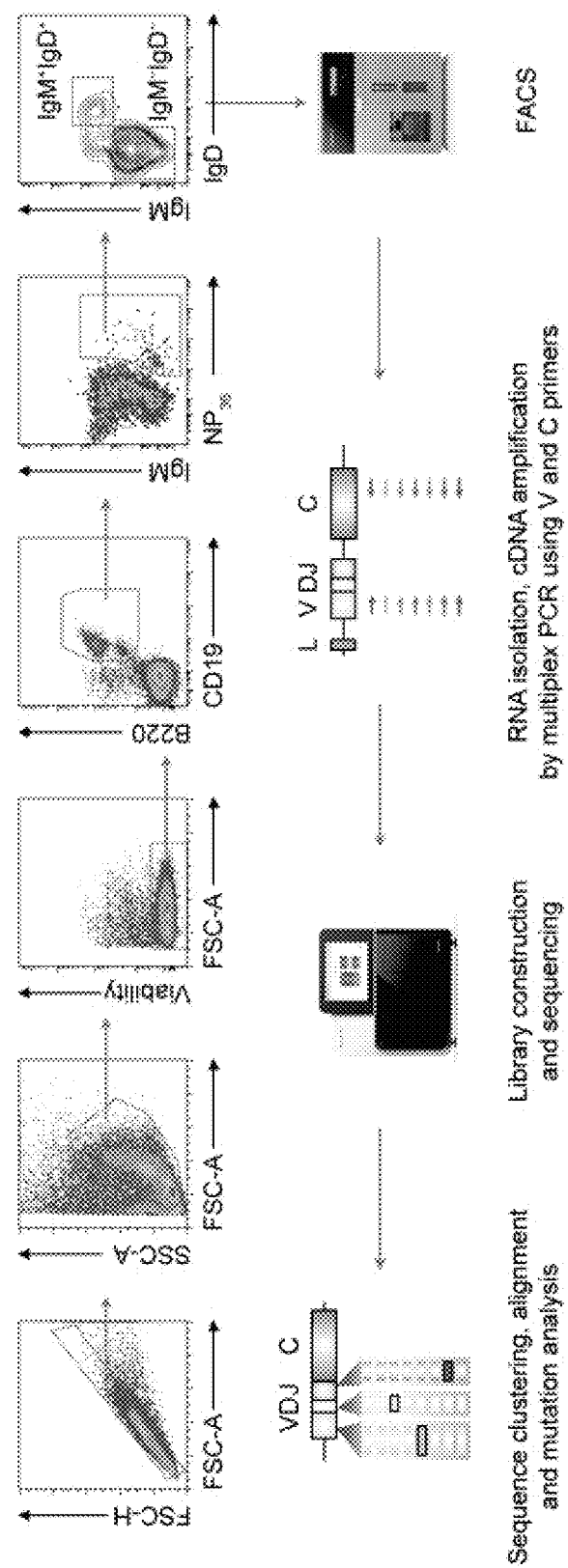
FIGS. 13A, 13B. Aire$^{-/-}$ donor B cells class-switched to IgG or IgE have increased IgH CDR2 SHMs than their Aire$^{+/+}$ counterparts after repeated immunizations.
Figure 13B:
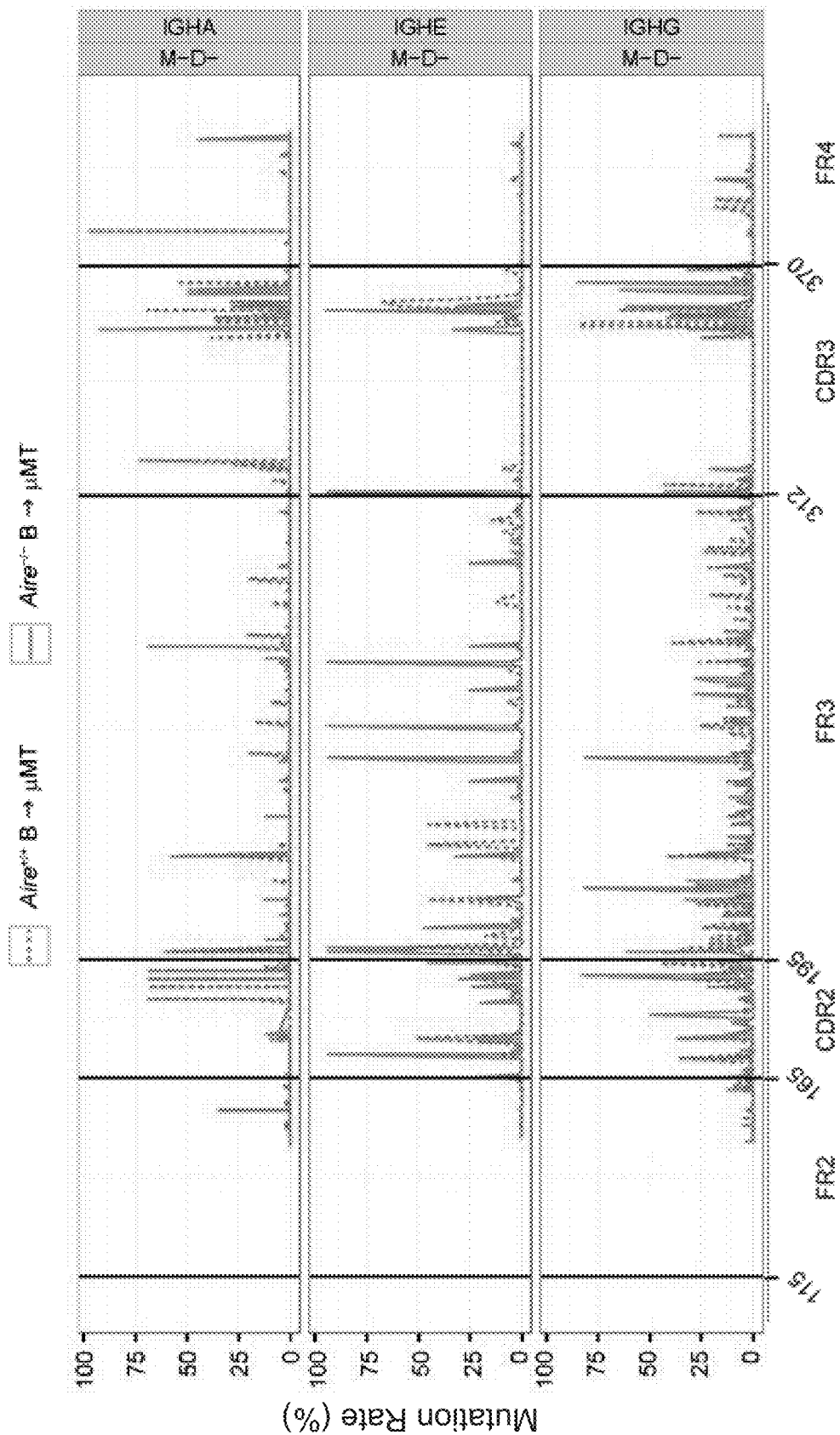
Figure 13B:
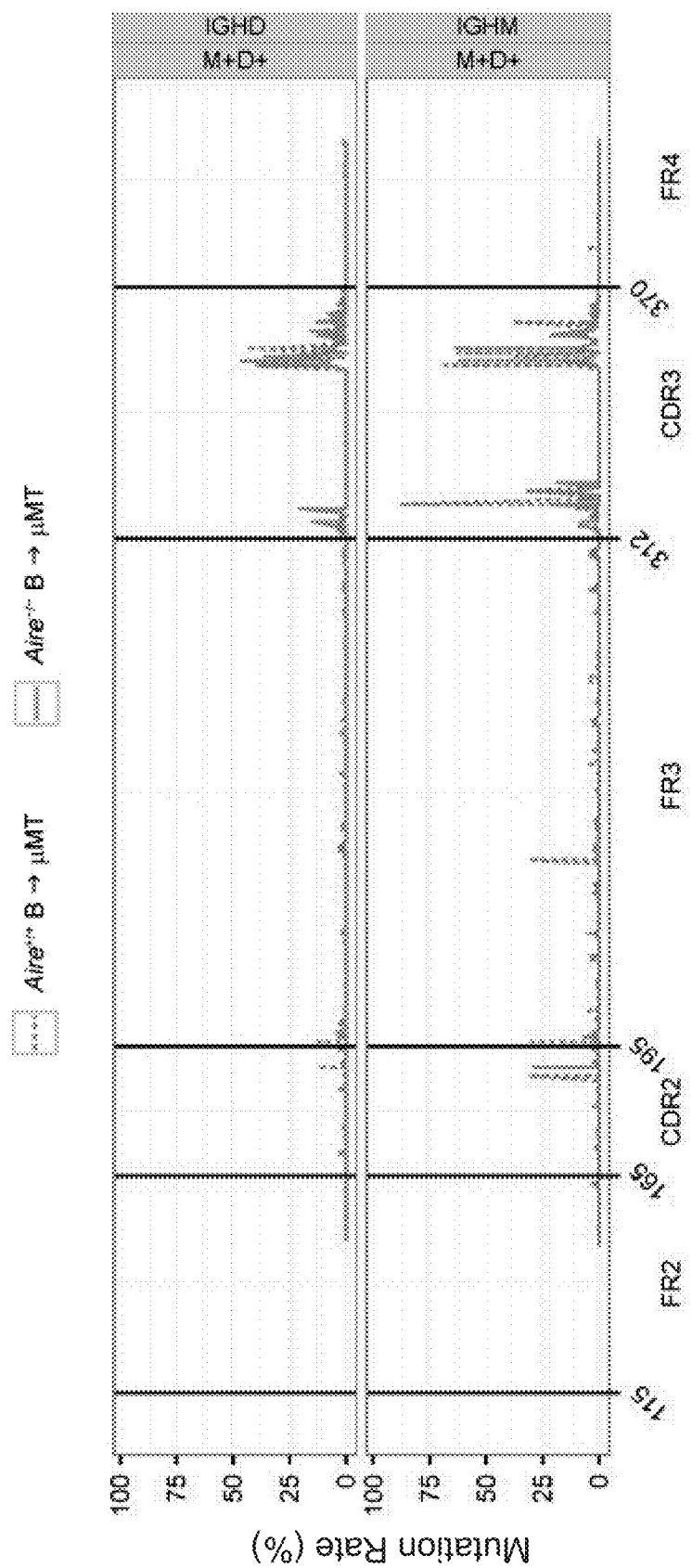
Figure 14A:
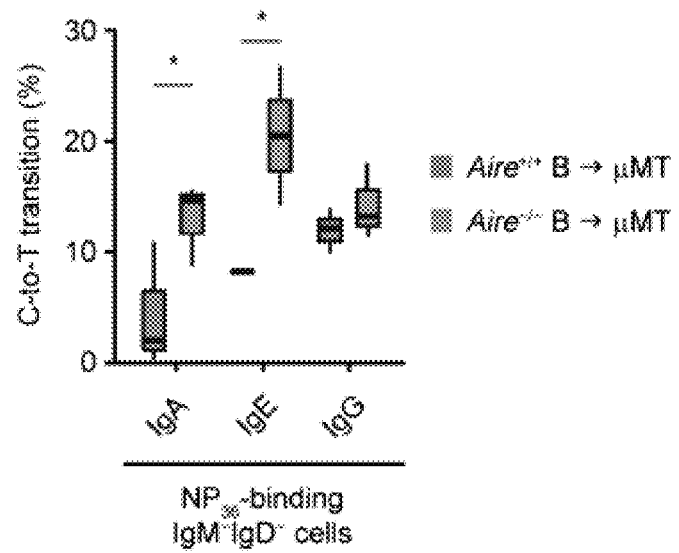
FIGS. 14A-14H. AIRE deficiency in B cells promotes humoral autoimmunity and compromises cutaneous anti-*Candida* defense.

Given that the vast majority of APS-1 patients mysteriously develop chronic mucocutaneous candidiasis (CMC) as an early clinical symptom, which may result from the aberrant production of class-switched neutralizing autoantibodies against T$_H$17 cytokines that can impair anti-*C. albicans* immunity (Puel et al., *The Journal of experimental medicine* 207, 291-297, (2010); Kisand et al., *The Journal of experimental medicine* 207, 299-308, (2010); Meyer et al., *Cell* 166, 582-595, (2016)), the molecular and functional impact of B cell-intrinsic AIRE in humoral immunity and anti-*Candida* defense was sought. The IgH variable region (IgHV) SHM landscape of antigen-specific Aire$^{+/+}$ and Aire$^{-/-}$ donor B cells after repeated immunization of recipient µMT mice with NP$_{32}$-KLH (FIG. 13A) were first compared. NP-specific Aire$^{-/-}$ B cells in the recipients' spleen that class-switched to IgG or IgE exhibited higher rates of IgHV SHMs in complementarity-determining region 2 (CDR2) and framework region 3 (FR3) than Aire$^{+/+}$ donor B cells (FIG. 13B). There was also an increased frequency of C-to-T transitions in the SHMs in the IgHV coding sequences in NP-specific Aire$^{-/-}$ donor B cells compared to Aire$^{+/+}$ donor B cells (FIG. 14A), a signature associated with the action of AID in IgHV. Maul et al., *Nature immunology* 12, 70-76, (2011).

Figure 14B:
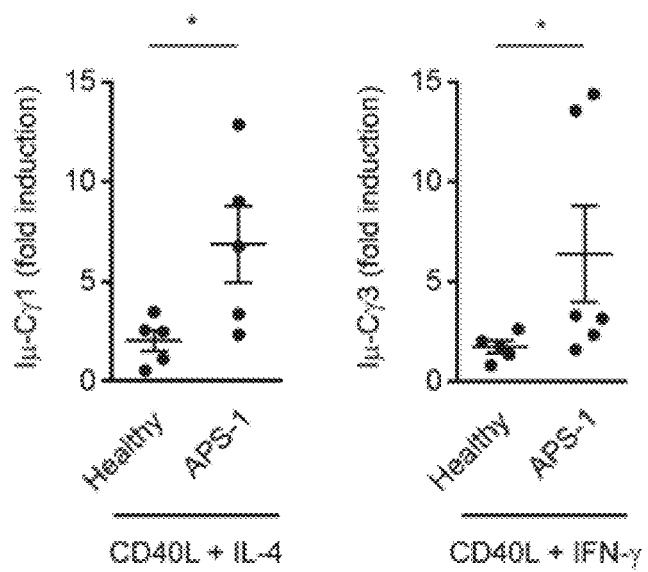
Figure 14C:
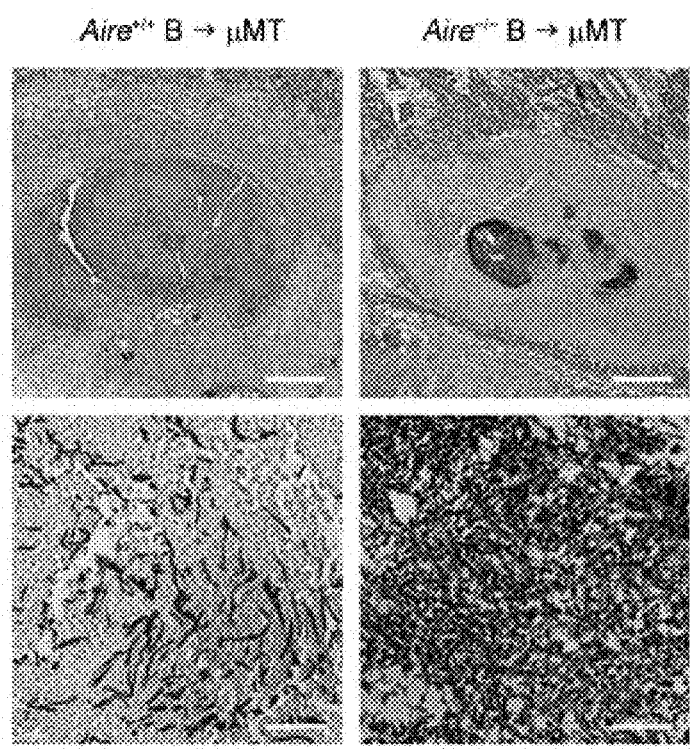
Figure 14D:
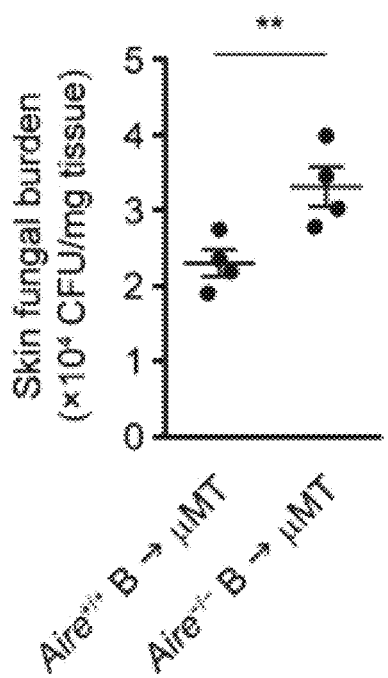
Figure 14E:
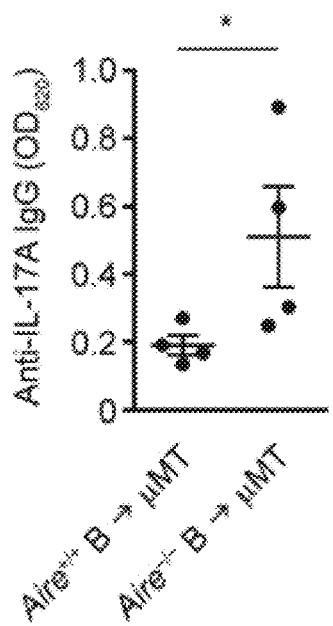
Figure 14F:
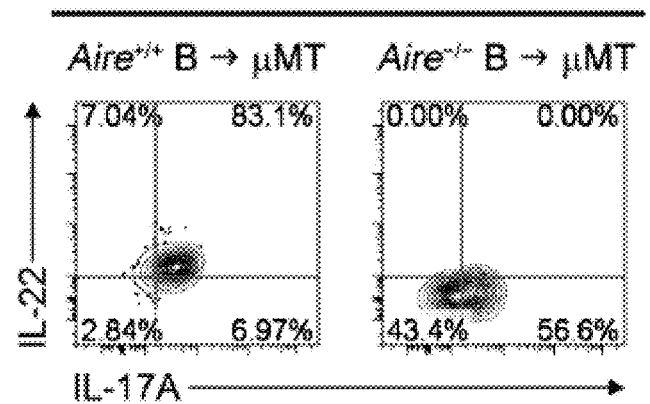
Figure 14G:
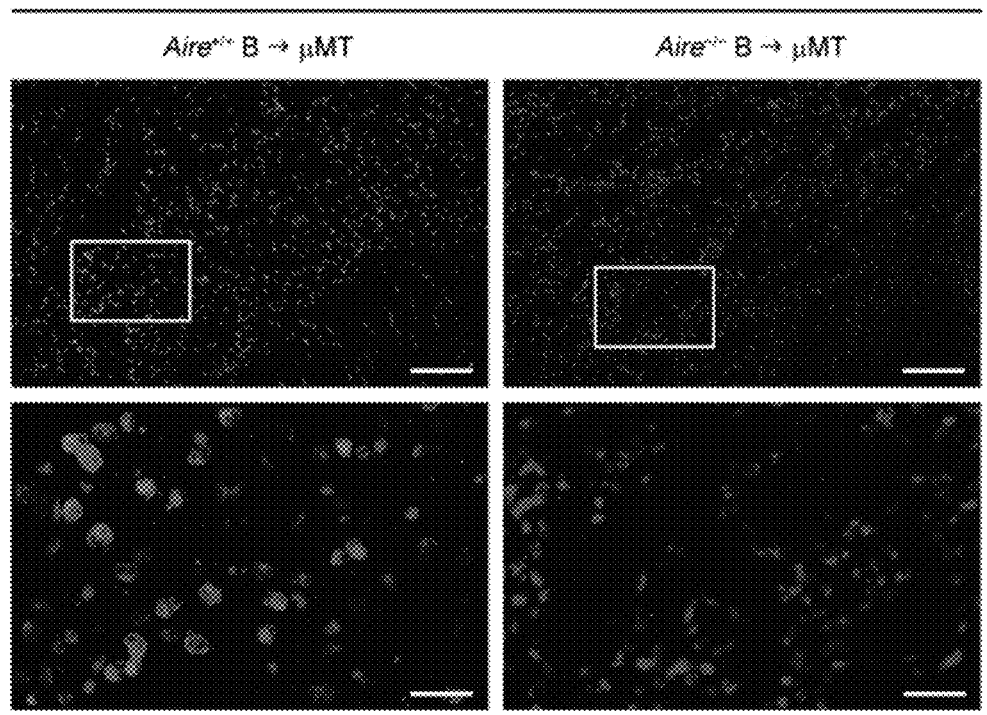
Figure 15A:
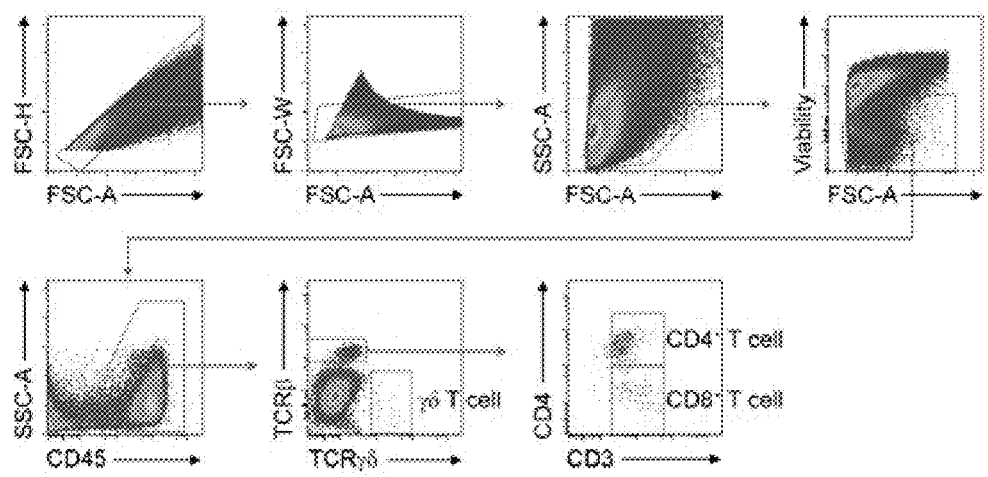
FIGS. 15A-15C. AIRE deficiency in B cells impairs T$_H$17 immunity against cutaneous *C. albicans* infection.
Figure 15B:
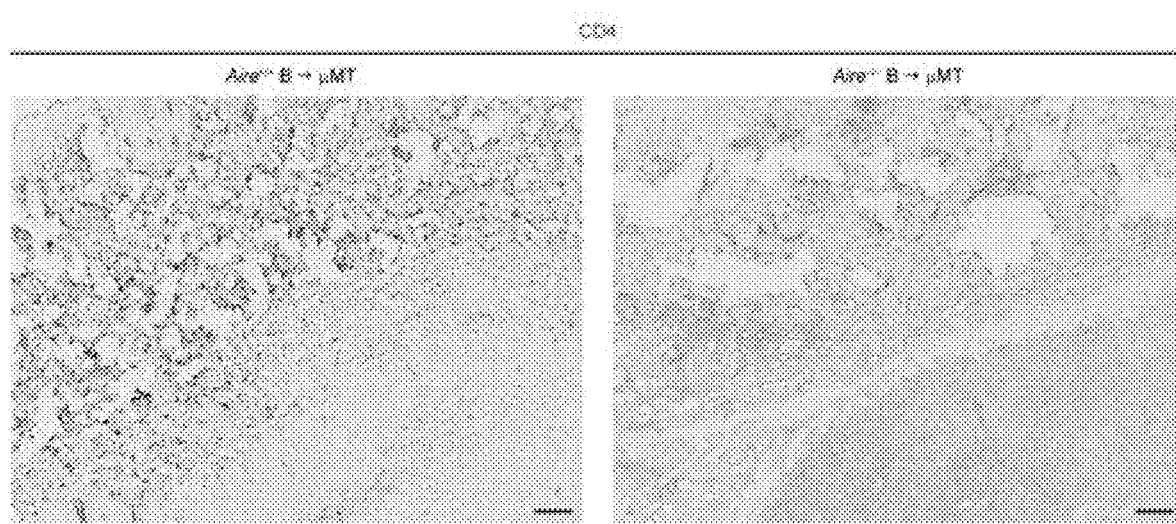
Figure 15C:
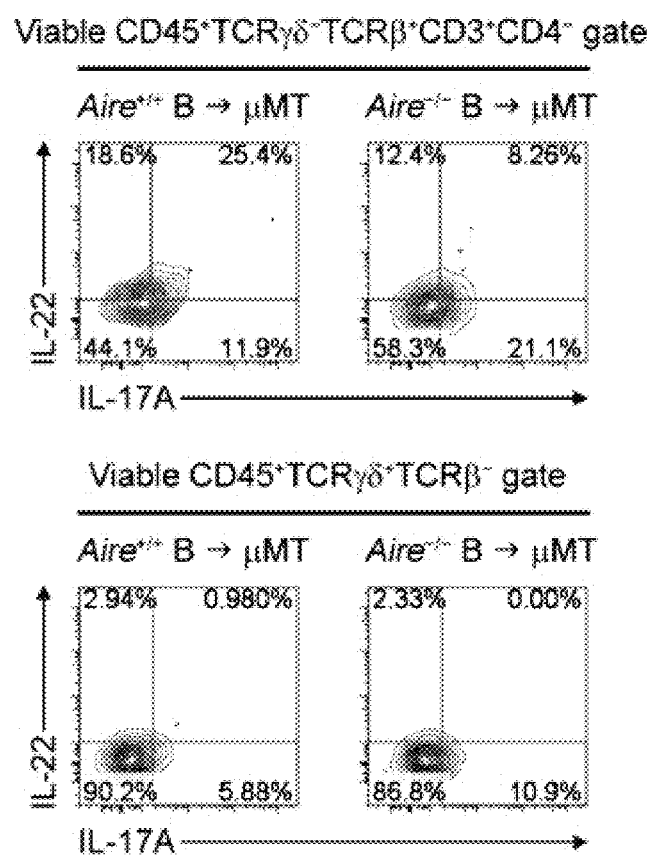

Furthermore, naïve B cells of APS-1 patients underwent elevated CSR than those of healthy donors upon stimulation ex vivo (FIG. 14B). It was then asked whether AIRE deficiency in peripheral B cells could promote APS-1-like CMC. After exposure to heat-killed *C. albicans* and subsequent cutaneous infection with live *C. albicans* pseudohyphae, µMT recipient mice of Aire$^{-/-}$ B cells had heightened fungal burden in the skin 4 d after infection (FIGS. 14C, 14D) and concomitant elevation of autoantibodies to IL-17A, IL-17F and IL-22 in the sera as compared to µMT recipients of Aire$^{+/+}$ B cells (FIG. 14E). µMT recipients of Aire$^{-/-}$ B cells also had reduced IL-17A- and IL-22-producing CD4$^+$ T cells (FIGS. 15A, 15B, FIG. 14F) but not γδ T cells (FIG. 15C), and diminished neutrophils infiltration (FIG. 14G) at the dermal infection site. Therefore, AIRE deficiency in peripheral B cells impairs cutaneous anti-*Candida* defense and promotes APS-1-like CMC by engendering humoral autoimmunity.

Figure 14H:
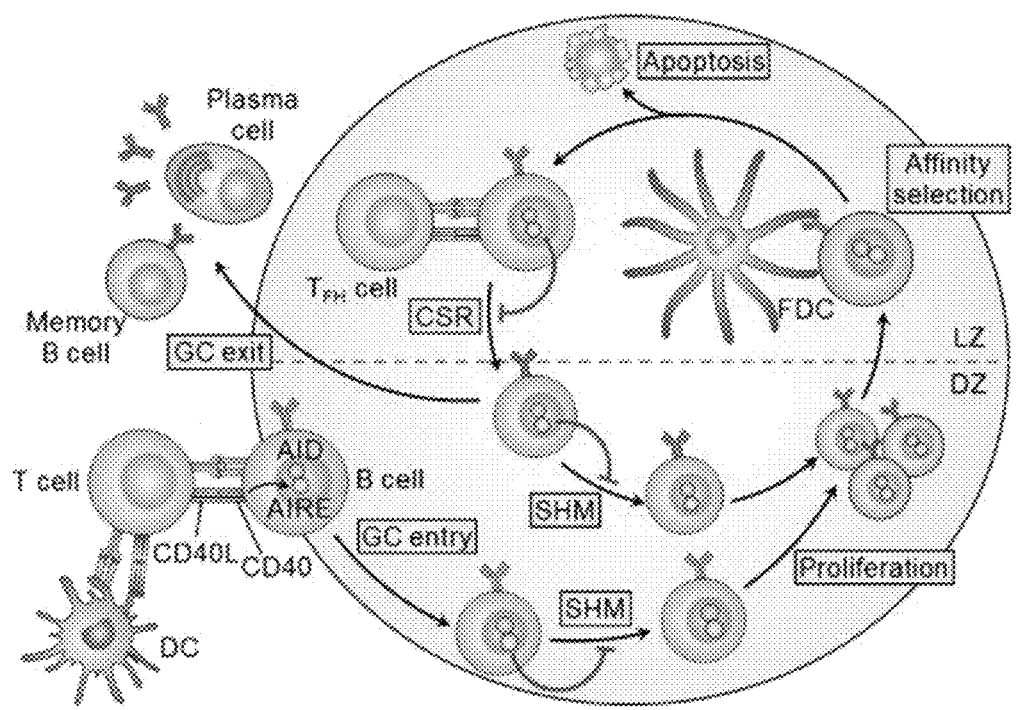

Collectively, this Example defines a crucial B cell-intrinsic AIRE-dependent GC checkpoint of peripheral antibody diversification which suppresses humoral autoimmunity that can arise from the GC reaction (Vinuesa et al., *Nature Review. Immunology*, 9, 845-857 (2009)) (FIG. 14H), and offers mechanistic insights into the production of high-affinity autoantibodies in many APS-1 patients. Puel et al., *The Journal of experimental medicine* 207, 291-297, (2010); Kisand et al., *The Journal of experimental medicine* 207, 299-308, (2010); Meyer et al., *Cell* 166, 582-595, (2016). These findings also highlight the emerging idea that peripheral tolerance mechanisms can be barriers to the generation of effective immunity, and controlled breaching of peripheral tolerance can permit neutralizing antibody responses that can be therapeutically beneficial. Meyer et al., *Cell* 166, 582-595, (2016); Schroeder et al., *The Journal of experimental medicine*, (2017); Rosenspire & Chen, *Frontiers in immunology* 6, 580, (2015). This has broad implications for new approaches of generating high-affinity neutralizing antibodies for therapeutic, diagnostic and research applications against, for example, infectious diseases and cancer.

Detailed Methods. Human subjects. Autoimmune polyglandular syndrome type 1 (APS-1) patients with loss-of-function mutations in the AIRE gene were enrolled in the study with an approved protocol of the Ethics Committee of Medicine of the Hospital District of Helsinki and Uusimaa (HUS), Finland. Hyper-IgM syndrome type 3 (HIGM3) patients with loss-of-function mutations in the CD40 gene were enrolled in the study with an approved Institutional Review Board (IRB) protocol of the Icahn School of Medicine at Mount Sinai. Peripheral blood leukocytes of anonymous healthy donors were obtained from the Southeast Michigan branch of American Red Cross with a protocol approved by the IRB of Wayne State University (WSU) and the Detroit Medical Centre (DMC). Tonsil, thymus and spleen tissues were obtained after pediatric tonsillectomy, cardiac surgery and splenectomy, respectively, from the Children's Hospital of Michigan with an IRB protocol approved by WSU and DMC.

Human blood and tissue sample processing and cell isolation. Peripheral blood mononuclear cells (PBMCs) of APS-1 patients and healthy controls were purified using Ficoll-Paque Plus (GE Healthcare 17-1440-03). Live (7AAD$^-$ or Ghost Violet 510$^-$) naive B cells (CD19$^+$IgD$^+$ CD27$^-$) and class-switched memory B cells (CD19$^+$IgD$^-$ CD27$^+$) were sorted from the PBMCs to a purity of ≥99% on a FACSAria II sorter (BD). PBMCs of anonymous healthy donors were isolated using a Histopaque-1077 gradient (Sigma-Aldrich 10771) following the manufacturer's instruction. Red blood cells (RBCs) were lysed using an ammonium-chloride-potassium (ACK) lysing buffer (Thermo Fisher Scientific A1049201). IgD$^+$ or CD19$^+$ B cells were purified from PBMCs by magnetic-activated cell sorting (MACS) with a biotinylated goat F(ab')$_2$ anti-human IgD antibody and anti-biotin magnetic microbeads (Miltenyi Biotec 130-090-485) as previously reported. Chen et al., *Nature immunology* 10, 889-898, (2009).

The purity of the IgD$^+$ B cells ranged from 92% to 99% as determined by flow cytometry with CD19 staining. CD19$^+$ B cells were similarly separated from PBMCs using a biotinylated mouse anti-human CD19 (clone HIB19) antibody, with purity ranging from 94% to 98% as determined by flow cytometry using a different clone (SJ25C1) of CD19 antibody. Human tonsil and spleen tissues were minced into small pieces, meshed through 100 µm cell strainers, and pelleted at 600 g for 5 min at 4° C. Spleen cells were treated with an ACK buffer to remove erythrocytes and filtered through 40 µm cell strainers. Tonsil and spleen cells were then washed with phosphate-buffered saline (PBS). Thymic cell suspensions were obtained by mincing human thymus tissues into small pieces and mechanically removing thymocytes followed by 2 rounds of digestion with 0.2% (w/v) Collagenase II (Worthington Biochemical LS004177) and 0.1 mg/ml DNase I (Roche 11284932001) in Hank's Balanced Salt Solution (HBSS) for 45 min at 37° C. with shaking. The digested samples were filtered through 70 µm cell strainers and washed with PBS.

Mice. C57BL/6J mice (Jackson stock number 000664), Aire$^{+/-}$ (B6.129S2-Aire$^{tm1.1Doi}$/J, Jackson stock number 004743) and µMT (B6.129S2-Ighm$^{tm1Cgn}$/J, Jackson stock number 002288) were purchased from the Jackson Laboratory. Aire$^{Adig}$ mice in C57BL/6 background were previously reported. Gardner et al., Science, 321, 843-847 (2008). Aicda$^{-/-}$ mice[1] were generously provided by Dr. Tasuku Honjo (Kyoto University, Japan). These mice were maintained in the same room at the specific pathogen-free (SPF) facility of the Division of Laboratory Animal Resources (DLAR) at Wayne State University. Aire$^{-/-}$ mice were generated by mating Aire$^{+/-}$ mice, and age- and sex-matched Aire$^{+/+}$ littermates were used as controls for ex vivo and in vivo experiments. All breeding and experimental protocols were approved by Wayne State University Institutional Animal Care and Use Committee (IACUC).

Mouse blood and tissue cell isolation. Blood, spleen, inguinal lymph nodes, mesenteric lymph node and Peyer's patches were collected from euthanized mice. Adjacent fat and other tissues were removed before single cells suspensions were prepared, filtered through 100 µm cell strainer. RBCs from blood were removed by centrifugation on Histopaque 1077, and those in spleens were lysed using an ACK buffer. The cells were washed in PBS and counted before cell sorting, flow cytometry or purification by MACS. Resting B cells were isolated from the spleens of age- and sex-matched Aire$^{+/+}$ or Aire$^{-/-}$ littermates by MACS using a B Cell Isolate Kit (Miltenyi Biotec 130-090-862). The purity of the isolated B cells ranged from 97-99.6% as determined by flow cytometry based on CD19 and B220 staining.

Mouse immunization. 2.5×10$^7$ purified Aire$^{+/+}$ or Aire$^{-/-}$ B cells were introduced via the tail vein into each recipient µMT littermate mouse. One day after the adoptive transfer, each recipient was intraperitoneally (i.p.) immunized with 1 dose of 100 µg NP$_{32}$-KLH (Biosearch Technologies N-5060) in Complete Freund's Adjuvant (Thermo Fisher Scientific 77140) and 4 doses of 100 µg NP$_{32}$-KLH in Incomplete Freund's Adjuvant (Thermo Fisher Scientific 77145) once every week. Four days after the last immunization, mice were sacrificed and blood and spleens were collected for ELISA, flow cytometry or cell sorting. In some experiments, mice were immunized with 200 µl of 2% sheep red blood cells in sterile PBS for 3 times, with each dose being 1 week apart.

Candida albicans culture. A single colony of C. albicans (ATCC MYA-2876) was cultured in YPD broth (BD 242820) at 30° C. for 16 h with shaking at 220 rpm. C. albicans existed in blastospore form after the 16 h culture. The concentration of the culture was quantitated using a haemocytometer. The culture was diluted 1:10 with fresh YPD broth containing 10% (v/v) heat-inactivated FBS (Thermo Fischer Scientific 26140079) and grown at 37° C. for 3 h with shaking at 220 rpm. An aliquot of the culture was removed and examined under the microscope to ensure that 95% of blastospores switched to the virulent pseudo-hyphal form. The culture was pelleted by centrifugation at 4,000 rpm for 10 minutes, washed with PBS twice and resuspended in PBS at the concentration of 5×10$^6$ CFU per 50 µl based on the quantitation of the culture 3 h ago. The pseudohyphae samples were used for either intradermal infection of mice or the preparation of heat-killed samples by treatment at 95° C. for 2 h followed by 3 rounds of sonication on ice at 30% maximum power for 5 seconds per round using a sonifier (Thermo Fisher Scientific Q500).

Cutaneous C. albicans infection of mice. 5×10$^7$ purified Aire$^{+/+}$ or Aire$^{-/-}$ B cells were introduced via the tail vein into each recipient µMT mouse littermate. Starting from the day of adoptive transfer, 5 doses each of 10$^6$ CFU heat-killed C. albicans pseudohyphae were given intraperitoneally to each recipient mouse every 4 d. Four days after the last injection, mice were infected with 5×10$^6$ CFU live C. albicans pseudohyphae in 50 µl PBS per spot at the deep dermis of the shaved dorsal region. Conti et al., Curr Protoc Immunol 105, 19 16 11-19 16 17, (2014). The actual dose of infection was determined by immediately plating serial dilutions of the inoculum on YPD agar in triplicate, incubating the plates at 28° C. for 24 h and colony enumeration. The inoculum size per spot ranged between 3.8-12.3×10$^6$ CFU in various experiments. Four days after the infection, blood was obtained after sacrificing the mice. The entire dermal injection site was excised for histological evaluation of fungal burden by Grocott's methenamine silver (GMS) stain or by plating, or for determination of effector T cell response by flow cytometry. For GMS stain, the tissues were immediately fixed in 10% formalin overnight and embedded in paraffin before sectioning. For plating, each tissue was weighed, minced, grounded thoroughly and resuspended in sterile PBS. Serial dilutions of the suspensions were plated on YPD agar in triplicate and incubated at 28° C. for 24 h before colony enumeration. The fungal load was calculated as CFU per mg of tissue. For flow cytometry, the tissues were washed in FBS-free RPMI-1640 twice, minced and digested in FBS-free RPMI-1640 containing 0.7 mg/ml collagenase II (Worthington LS004177), 2 mM EDTA and 25 mM HEPES at 37° C. for 1 h. The digested samples were passed through a 70 µm cell strainer, washed twice with RPMI-1640 containing 10% FBS, 2 mg/ml glutamine, 100 U/ml penicillin, 100 µg/ml streptomycin and 25 µg/ml amphotericin B. The samples were then cultured in this medium further supplemented with 500 ng/ml PMA, 500 ng/ml ionomycin and 1 µg/ml GolgiPlug (BD 555029) at 37° C. for 5 h before being harvested for flow cytometric analysis.

Culture and stimulation or primary B cells. Peripheral blood IgD$^+$ or CD19$^+$ B cells of healthy donors, CD19$^+$IgD$^+$CD27$^-$ B cells of APS-1 patients or mouse splenic B cells were cultured in RPMI-1640 medium (Sigma-Aldrich R8578) supplemented with 2 mM L-glutamine, 2 mg/ml NaHCO$_3$, 100U/ml penicillin, 100 µg/ml streptomycin, 0.25 µg/ml amphotericin B and 10% FBS (Thermo Fisher Scientific 26140-079 or Sigma-Aldrich F4135). Peripheral blood IgD$^+$ or CD19$^+$ B cells of healthy donors were stimulated with 500 ng/ml soluble CD40L (sCD40L) (Peprotech 310-02) and 100 ng/ml IL-4 (Peprotech 200-21) or 100 ng/ml IL-21 (Peprotech 200-04). Peripheral blood IgD$^+$CD27$^-$ naive B cells of healthy subjects or APS-1 patients were stimulated with 500 ng/ml sCD40L and 100 ng/ml IL-4 or 100 ng/ml IFN-γ (Peprotech 300-02). Purified mouse splenic B cells were stimulated with 500 ng/ml sCD40L (Peprotech 315-15) with or without 100 ng/ml IL-4 (Peprotech 214-14), 100 ng/ml IL-21 (Peprotech 210-21) or 25 µM CAPE (Cayman Chemical 70750). In some experiments, sCD40L was replaced with 5 µg/ml anti-CD40. To determine cell proliferation, the cells were labelled with carboxyfluorescein succinimidyl ester (CFSE) (Biolegend 422701) according to the manufacture's protocol prior to culture. Alternatively, 10 µM 5-ethynyl-2'-deoxyuridine (EdU) was added to the culture medium for 6 hours before EdU incorporation was determined by flow cytometry using a Click-iT EdU Flow Cytometry Assay Kit (Thermo Fisher Scientific C10418) according to the manufacturer's protocol.

Culture and stimulation of B cell lines. The human IgM$^+$IgD$^+$ 2E2 B cell line (He et al., *Journal of immunology* 173, 4479-4491, (2004)) and Ramos B cell line (ATCC CRL-1596) were cultured in the above RPMI-1640 medium. 2E2 cells were stimulated with 500 ng/ml sCD40L with 100 ng/ml IL-21. WT CH12 cells (from Dr. Tasuku Honjo, Kyoto University, Japan) and Aire$^{-/-}$ CH12 cells were cultured in the above RPMI-1640 medium further supplemented with 5% (v/v) NCTC-109 (Sigma-Aldrich N1140) and 50 µM β-mercaptoethanol (Sigma-Aldrich M3148). To induce IgA switching, the cells were stimulated with 1 µg/ml anti-mouse CD40 (eBioscience 16-0402), 12.5 ng/ml IL-4 (R&D 404-ML) and 1 ng/ml TGF-β1 (R&D 7666-MB/CF) for 3 d. The human embryonic kidney cell/Burkitt's lymphoma fusion cell line HKB-11 (ATCC 12568) was cultured in DMEM/F12 (Sigma-Aldrich D8437) supplemented with 2 mM L-glutamine, 100 U/ml penicillin, 100 µg/ml streptomycin, 0.25 µg/ml amphotericin B and 10% FBS.

Generation and validation of Aire$^{-/-}$ CH12 cells. Several clones of Aire$^{-/-}$ CH12 cells were generated by targeting the Aire gene using the CRISPR/Cas9 system as described in Ran et al., *Nat Protoc* 8, 2281-2308, (2013). Single guide RNAs (sgRNA) targeting exon 1 or exon 3 of mouse Aire gene (GenBank NC_000076.6) were designed using the online tool at crispr.mit.edu. Sequences with the highest score for the respective region were selected to express sgRNAs, pairs of oligonucleotides were synthesized and cloned into pSpCas9(BB)-2A-Puro plasmid (Addgene 48139) as reported in Ran et al., *Nat Protoc* 8, 2281-2308, (2013). The sgRNA expression plasmid was then transfected into CH12 cells using electroporation (square wave pulse at 200 V for 30 ms) in serum-free RPMI-1640 with 5 mM glutathione in a 4-mm cuvette. 24 hours after transfection, cells were resuspended in 125 ng/ml puromycin for 48 hours. After a brief expansion in puromycin-free media, single cell clones from transfected cells were screened for loss of the sgRNA targeting site using PCR. Clones with deletions in both alleles were identified by PCR. To determine the exact genomic modifications in each clone, the sgRNA-targeting sites were amplified with primer pairs spanning the targeting sites, and PCR products were sequenced directly using the respective forward primer. In addition, PCR products from clones 43 and 53 were cloned into the pGEM-T Easy vector and sequenced with T7 primer. All three mutant clones used were confirmed to harbor frameshift mutations on both alleles, resulting in termination shortly after the frameshift site. The potential off-target sites in the mouse genome for each guide were identified by the same online tool (crispr.mit.edu). Cas9 generally does not tolerate more than 3 mismatches. Hsu et al., *Nat Biotechnol* 31, 827-832, (2013).

All off-target sites in a potential gene-coding region with non-zero scores (up to 4 mismatches) were verified by sequencing to be intact. The lack of AIRE protein expression in these clones was finally confirmed by Western Blot.

Plasmids. Full-length human AIRE cDNA sequence was cloned into pcDNA3.1(−) with tandem C-terminal Myc and 6-Histidine tag (Thermo Fisher Scientific V38520). Sequences coding various domains of AIRE were deleted using a Phusion Site-Directed Mutagenesis Kit (Thermo Fisher Scientific F541) using appropriate primers (FIG. 12A). Briefly, to delete a specific section of AIRE in the vector, a pair of outward primers was designed to amplify the remaining region together with the plasmid backbone. PCR product was then phosphorylated at 5' end and ligated with Quick T4 ligase (New England Biolabs M2200L) to recircularize it. Human AID was obtained by cloning full-length AICDA into pFLAG-CMV2 vector with an N-terminal FLAG tag (Sigma-Aldrich E7033). Domain-specific deletion mutants and G23S and E58A point mutants of AID were generated using the Phusion Site-Directed Mutagenesis kit using appropriate primers (FIG. 12B). The full-length Egfp sequence from pcDNA3-eGFP (from Dr. Thilo Hagen, National University of Singapore) was then cloned in frame to the C-terminus of AIRE or AIREΔNLS using blunt end ligation of PCR-amplified fragments (FIG. 12C).

Transfection. $10^6$ seeded HKB-11 cells were cultured to 70-90% confluence and transfected with 4 µg plasmid DNA using Lipofectamine 3000 (Thermo Fisher Scientific L3000015) in Opti-MEM (Thermo Fisher Scientific 31985070) by following the manufacturer's instruction. $10^6$ CH12 cells were suspended in a 4-mm electroporation cuvette containing 600 µl sterile PBS. Electroporation was performed using the Bio-Rad Gene Pulser Xcell system (voltage=550 V, capacitance=50 µF, resistance=∞, time constant=1.2 ms). The electroporated cells were transferred to 10 cm culture dishes, subsequently divided equally into 2 dishes containing the CH12 cell culture media supplemented with 250 µg/ml Geneticin, with one dish left unstimulated and the other stimulated with 1 µg/ml anti-CD40, 1 ng/ml TGF-β1 and 12.5 ng/ml IL-4 for 4 d.

Immunoprecipitation. Cultured cells were harvested, washed with cold PBS twice and lysed with a CelLytic™ M buffer (Sigma-Aldrich C2978) containing 1× protein inhibitor cocktail (Sigma-Aldrich P8340) and 1× Halt phosphatase Inhibitor (Thermo Fisher Scientific 78426) for 60 minutes on ice. The lysates were centrifuged at 12,000 g for 15 minutes at 4° C. Protein concentration in the supernatants was determined by a BCA Protein Assay Kit (Thermo Fisher Scientific 23225). Equal amounts of lysate supernatants were used for immunoprecipitation with specific or isotype control antibodies using protein G magnetic beads (Cell Signaling 8740 or Thermo Fisher Scientific 88847) according to the manufacturers' instructions.

RNA extraction and quantitative real-time polymerase chain reaction. RNA was extracted from cells or tissues other than those from the APS-1 patients using TRIzol (Thermo Fisher Scientific 15596026). cDNA synthesis was performed using the Superscript III first strand synthesis system (Thermo Fisher Scientific 188080051) in a thermocycler (Bio-Rad T100). qRT-PCR was performed with PowerSYBR® Green Master Mix (Thermo Fisher Scientific 4367660) on a StepOnePlus instrument (Applied Biosystems) using pairs of sense and anti-sense primers targeting the genes of interest (FIGS. 16A, 16B). For APS-1 patients' peripheral blood IgD$^+$CD27$^-$ B cells, following stimulation, the cells were washed and stored in RNAlater® storage reagent (Thermo Fisher Scientific AM7020). Prior to RNA isolation, cells were pelleted and the RNAlater® was removed. RNA was isolated using the lysis and stop solutions in a Cells-to-C$_T$ 1-step SYBR Green kit (Thermo Fisher Scientific A25601) and amplified using an iTaq Universal SYBR Green One-Step kit (Bio-Rad 172-5150) on a StepOnePlus instrument using pairs of sense and anti-sense primers targeting the genes of interest (FIG. 16A). The ACTB (Actb) gene was used as an internal control for normalization.

Chromatin immunoprecipitation and quantitative real-time PCR. ChIP was performed using a ChIP assay kit (EMD Millipore 17-295) based on the manufacturer's instructions with slight modifications. Following 3 d of stimulation of $10^6$ CH12 cells as described above, formaldehyde was added to the culture to the final concentration of 1% and incubated for 10 minutes at 37° C. to crosslink chromatin. The cells were pelleted, washed twice in PBS, resuspended in an SDS lysis buffer (1% SDS, 10 mM EDTA, 50 mM Tris, pH 8.1) for 10 minutes on ice. DNA was sheared by 3 rounds of sonication on ice at 30% maximum power for 3 seconds per round using a sonifier (Thermo Fisher Scientific Q500). After centrifugation at 13,000 rpm for 10 minutes, the supernatants were harvested, diluted 10-fold in a ChIP dilution buffer (0.01% SDS, 1.1% Triton X-100, 1.2 mM EDTA, 16.7 mM Tris-HCl, 167 mM NaCl, pH 8.1) containing protease inhibitors, and precleared with 50% protein A agarose/salmon sperm DNA slurry for 30 minutes at 4° C. with rotation. After setting aside an aliquot as input, an AID or control antibody was then added and incubated overnight at 4° C. with rotation, followed by the addition of 50% protein A agarose/salmon sperm DNA slurry for 1 h at 4° C. with rotation. The agarose was then pelleted and sequentially washed once with the low salt wash buffer, once with the high salt wash buffer, once with the LiCl wash buffer and twice with TE buffer, all of which were components of the kit. DNA in the bound chromatin was eluted from the beads using an elution buffer (1% SDS, 0.1 M $NaHCO_3$, pH 8.0), reverse-crosslinked from proteins by incubation at 65° C. for 4 h in the presence of 200 mM NaCl, cleaned by 20 μg/ml RNase A treatment for 30 minutes at 37° C. followed by 40 μg/ml proteinase K treatment for 1 h at 45° C., purified using phenol/chloroform extraction followed by ethanol precipitation with carrier glycogen according to the kit's manual and resuspended in TE buffer for quantitative real-time PCR analysis using PowerSYBR® Green Master Mix (Thermo Fisher Scientific 4367660) with the primers in FIG. 16B on a StepOnePlus instrument (Applied Biosystems). The fold enrichment of DNA was calculated using the $\Delta\Delta C_T$ method with control antibody-precipitated samples as an internal reference, and further compared among different CH12 cells and treatments.

Protein extraction and Western Blot. Cells were pelleted and washed twice with ice-cold PBS, lysed with a pH 8.0 protein extraction buffer containing 20 mM Tris-HCl, 150 mM NaCl, 1% IGEPAL CA-630 (NP-40, Sigma-Aldrich 18896), 0.1% sodium dodecyl sulphate (SDS), 1 mM EDTA and protease and phosphatase inhibitor cocktail for 30 minutes on ice. Supernatants were collected after centrifugation, heated at 98° C. in SDS sample buffer with 4% β-mercaptoethanol for 5 minutes to denature proteins. Proteins were resolved in 4-20% Bis-Tris gels (GeneScript M42012) or 10% Tris-Glycine gels (Bio-Rad 4561034) and transferred to 0.2 μm polyvinylidene fluoride (PVDF) membranes (Bio-Rad 1620177). The membranes were blocked with 5% (w/v) non-fat milk in Tris-buffered saline with Tween-20 for 30 minutes to 1 h, incubated with primary antibodies (FIGS. 17A, 17B, 17D) overnight at 4° C. and subsequently with secondary antibodies conjugated to HRP (FIG. 17E). Signals were visualized with clarity western-blot ECL substrate (Bio-Rad 170-5061) and exposed on autoradiograph films.

Conventional flow cytometry. Cells were incubated with an Fc blocking reagent (Miltenyi Biotec 130-059-901 or Tonbo Biosciences 70-0161) and stained in PBS at 4° C. with antibodies to various cell surface antigens (FIGS. 17A, 17B, 17D). For staining of intracellular molecules, cells were subsequently fixed and permeabilized using a CytoFix/CytoPerm™ kit (BD 554722) or a Transcription Factor Buffer set (BD 562725). Isotype-matched control antibodies were used to define the baseline staining for the molecules of interest. Cells or beads stained with each fluorochrome were used to establish fluorescent compensation. 7-aminoactinomycin D (7-AAD, Tonbo Biosciences 13-6993-T500 or BD 559925) or Ghost Dye Violet 510 (Tonbo Biosciences 13-0870-T500) was used to identify and exclude non-viable cells from the analysis. Events were acquired on an LSR II or LSR Fortessa™ flow cytometer (BD) and analysed using FlowJo 7.6 (Tree Star).

Imaging flow cytometry. $CD19^+$ B cells were purified from tonsillar cell suspensions by MACS with a biotinylated anti-CD19 antibody and anti-biotin microbeads (FIG. 17A). The cells were then incubated with an Fc blocking reagent and stained at 4° C. with antibodies to surface IgD and CD38, fixed and permeabilized, and stained for AID and AIRE or with isotype control antibodies, (FIGS. 17A, 17D). Nuclei were counter stained with 4',6-diamidine-2'-phenylindole dihydrochloride (DAPI, Sigma-Aldrich D9542). Tonsillar cells stained with each fluorochrome were used to establish fluorescent compensation. Cells were imaged on an ImageStream® X Mark II imaging flow cytometer (Amnis®) and data were analysed using IDEAS 6.1 (Amnis).

Immunofluorescence analysis. Frozen human tissues were stored at −80° C. before 6-7 μm tissue sections were made using a cryostat (Leica CM1950). Sections were fixed with 4% paraformaldehyde, permeabilized in PBS containing 0.2% Triton X-100, blocked with PBS containing 1% BSA, 100 μg/ml human IgG and 10% serum from the source of the fluorochrome-conjugated antibodies, and stained with various combinations of primary antibodies against the molecules of interest (FIGS. 17A, 17B, 17D), followed by appropriate fluorochrome-conjugated secondary antibodies (FIG. 17E). Nuclei were visualized with DAPI. Following washing, slides were mounted using a FluoroSave™ reagent (EMD Millipore 345789) and imaged on a confocal microscope (Zeiss LSM 780 or Leica TCS SP5). Pseudocolor images were processed using Photoshop CS6 (Adobe).

ELISA. ELISA to determine NP-specific antibody affinity maturation was performed as previously described (Ballon et al., *The Journal of clinical investigation* 121, 1141-1153, (2011)) with minor modifications in the reagents. Briefly, each serum sample was titrated on both $NP_{29}$-BSA- and $NP_4$-BSA-coated microtiter plates. The ratio of binding to $NP_4$-BSA and $NP_{29}$-BSA is an indicator of relative Ig affinity maturation. Bound antibodies were detected using horseradish peroxidase (HRP)-conjugated goat-anti-mouse IgG1, IgG2b or IgG3 (FIG. 17B). The colorimetric reaction was terminated with the addition of an equal volume of 1 M $H_2SO_4$ and quantitated on a microplate reader (BioTek Epoch) at 450 nm. ELISA to determine IgG1 and IgA secretion by ex vivo stimulated mouse B cells was performed using a mouse IgG1 or IgA quantitation set (Bethyl E90-105 or E90-103). Anti-IL-17A, IL-17F and IL-22 autoantibodies in mouse sera were measured using microtiters plates coated with 1 μg/ml recombinant murine IL-17A (Rockland 010-001-B32), IL-17F (Rockland 010-001-B32) or IL-22 (GoldBio 1310-22). The plates were blocked with 10% BSA in PBS, washed, incubated with mouse serum samples, washed and then incubated with an alkaline phosphatase (ALP)-conjugated horse-anti-mouse IgG antibody (1:500, Vector Laboratories AP-2000). Following washing, the colorimetric reaction was developed using the Blue-Phos® phosphatase substrate system (KPL 50-88-02) and quantitated on a microplate reader (BioTek Epoch) at 620 nm.

IgHV repertoire and mutation analysis. Live (7-AAD$^-$) unswitched (IgM$^+$IgD$^+$) or switched (IgM$^-$IgD$^-$) NP-specific B cells (CD19$^+$B220$^+$NP$_{36}^+$) in the spleens of immunized µMT recipients were sorted using a SONY SH800 cell sorter (SONY Biotechnology) and resuspended in RNAProtect solution (QIAGEN 76526). High-throughput IgHV repertoire profiling by RNA-Seq was performed iRepertoire, Inc. The raw sequences were processed and analysed using the IMonitor 1.1.0 pipeline. Zhang et al., Genetics 201, 459-472, (2015). With this pipeline tool, each sequence was mapped to the *Mus musculus* germline V-D-J sequences (IMGT, available online at imgt.org/vquest/refseqh.html) to identify the V, D and J gene segments, and the CDRs, such as CDR3, were also determined for clonal clustering. The sequences observed only once in a sample were filtered off to reduce the sequencing error. Subsequently, the sequences were normalized according to the number of cells in each sample. By comparing the sequence of each clone with the germline sequence, the mismatches of nucleotides were regarded as potential mutations. To eliminate PCR noise and sequencing errors, the first 25 bp of the sequences corresponding to the primer-binding site were excluded from the analysis, and the sequences were filtered if 3 successive mismatches were observed in them. Finally, the mutation rate for each IMGT position in the IgHV was calculated if the sequencing depth for that position was and the frequency of each type of nucleotide substitution at these mutated positions were computed for each Ig isotype.

Statistical analysis. Results are expressed as mean±S.E.M. Statistical difference was assessed by t-test or Mann-Whitney U test as stated in the figure legends, unless otherwise indicated.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the production of antibodies with increased SHM and CSR following AIRE downregulation, as described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The invention claimed is:

1. A method of increasing somatic hypermutation (SHM) and class switch recombination (CSR) during antibody production, the method comprising:
   selecting a population of B cells with down-regulated autoimmune regulator (AIRE) function, wherein the population of B cells with down-regulated AIRE function has been contacted with an antigen; and
   stimulating the B cell population within in vitro culture conditions, wherein the stimulating comprises adding one or more of CD40L, IL-4, IFN-γ or TGF-α, wherein the increase is in relation to antibodies produced by a population of B cells with normal AIRE function contacted with the same antigen under comparable conditions.

2. The method of claim 1, further comprising one or more of:
   contacting the B cell population with down-regulated AIRE and the B cell population with normal AIRE function with an adjuvant;
   isolating the produced antibodies with increased SHM and CSR; or determining at least one CDR sequence of at least one antibody produced with increased SHM and CSR.

3. The method of claim 2, wherein the adjuvant comprises a Toll-like receptor ligand, a squalene-based adjuvant, alum, a STING agonist, and/or a cytokine.

4. The method of claim 1, further comprising modifying the B cells to down-regulate AIRE function.

5. The method of claim 4, wherein one or more of:
the modifying comprises AIRE gene editing and/or CD40 gene editing;
the modifying comprises AIRE gene editing and/or CD40 editing, wherein the AIRE gene editing and/or CD40 gene editing comprises CRISPR-Cas gene editing, transcription activator like effector nuclease (TALEN) gene editing, MegaTal gene editing, or zinc finger nuclease (ZFN) gene editing;
the modifying comprises AIRE gene editing, wherein the AIRE gene editing comprises contacting the modified B cells with SEQ ID NO: 9 and SEQ ID NO: 10;
the modifying results in AIRE protein that does not interact with AID;
the modifying results in AIRE protein that does not interact with AID, wherein
the AIRE protein lacks its caspase activation and recruitment domain (CARD) and/or its nuclear localization signal (NLS); or
the AIRE protein lacks amino acids 110-114 and 131-133 or lacks amino acids 101-180.

6. The method of claim 1 wherein:
the produced antibodies are human antibodies, non-human antibodies, or humanized antibodies; and/or
the antigen is a viral antigen, a bacterial antigen, a fungal antigen, or a cancer antigen; and/or
the increased SHM is within CDR regions, FR regions, or CDR regions and FR regions.

* * * * *

SEQUENCE LISTING

```
<160> NUMBER OF SEQ ID NOS: 13

<210> SEQ ID NO 1
<211> LENGTH: 515
<212> TYPE: PRT
<213> ORGANISM: Homo sapiens

<400> SEQUENCE: 1

Met Ala Thr Asp Ala Ala Leu Arg Arg Leu Leu Arg Leu His Arg Thr
1               5                   10                  15

Glu Ile Ala Val Ala Val Asp Ser Ala Phe Pro Leu Leu His Ala Leu
            20                  25                  30

Ala Asp His Asp Val Val Pro Glu Asp Lys Phe Gln Glu Thr Leu His
        35                  40                  45

Leu Lys Glu Lys Glu Gly Cys Pro Gln Ala Phe His Ala Leu Leu Ser
    50                  55                  60

Trp Leu Leu Thr Gln Asp Ser Thr Ala Ile Leu Asp Phe Trp Arg Val
65                  70                  75                  80

Leu Phe Lys Asp Tyr Asn Leu Glu Arg Tyr Gly Arg Leu Gln Pro Ile
                85                  90                  95

Leu Asp Ser Phe Pro Lys Asp Val Asp Leu Ser Gln Pro Arg Lys Gly
            100                 105                 110

Arg Lys Pro Pro Ala Val Pro Lys Ala Leu Val Pro Pro Pro Arg Leu
        115                 120                 125

Pro Thr Lys Arg Lys Ala Ser Glu Glu Ala Arg Ala Ala Ala Pro Ala
    130                 135                 140

Ala Leu Thr Pro Arg Gly Thr Ala Ser Pro Gly Ser Gln Leu Lys Ala
145                 150                 155                 160

Lys Pro Pro Lys Lys Pro Glu Ser Ser Ala Glu Gln Arg Leu Pro
                165                 170                 175

Leu Gly Asn Gly Ile Gln Thr Met Ser Ala Ser Val Gln Arg Ala Val
            180                 185                 190

Ala Met Ser Ser Gly Asp Val Pro Gly Ala Arg Gly Ala Val Glu Gly
        195                 200                 205

Ile Leu Ile Gln Gln Val Phe Glu Ser Gly Gly Ser Lys Lys Cys Ile
    210                 215                 220
```

Gln Val Gly Gly Glu Phe Tyr Thr Pro Ser Lys Phe Glu Asp Ser Gly
225                 230                 235                 240

Ser Gly Lys Asn Lys Ala Arg Ser Ser Gly Pro Lys Pro Leu Val
            245                 250                 255

Arg Ala Lys Gly Ala Gln Gly Ala Ala Pro Gly Gly Gly Glu Ala Arg
            260                 265                 270

Leu Gly Gln Gln Gly Ser Val Pro Ala Pro Leu Ala Leu Pro Ser Asp
        275                 280                 285

Pro Gln Leu His Gln Lys Asn Glu Asp Glu Cys Ala Val Cys Arg Asp
    290                 295                 300

Gly Gly Glu Leu Ile Cys Cys Asp Gly Cys Pro Arg Ala Phe His Leu
305                 310                 315                 320

Ala Cys Leu Ser Pro Pro Leu Arg Glu Ile Pro Ser Gly Thr Trp Arg
                325                 330                 335

Cys Ser Ser Cys Leu Gln Ala Thr Val Gln Glu Val Gln Pro Arg Ala
            340                 345                 350

Glu Glu Pro Arg Pro Gln Glu Pro Pro Val Thr Pro Leu Pro Pro
        355                 360                 365

Gly Leu Arg Ser Ala Gly Glu Glu Val Arg Gly Pro Pro Gly Glu Pro
    370                 375                 380

Leu Ala Gly Met Asp Thr Thr Leu Val Tyr Lys His Leu Pro Ala Pro
385                 390                 395                 400

Pro Ser Ala Ala Pro Leu Pro Gly Leu Asp Ser Ser Ala Leu His Pro
                405                 410                 415

Leu Leu Cys Val Gly Pro Glu Gly Gln Gln Asn Leu Ala Pro Gly Ala
            420                 425                 430

Arg Cys Gly Val Trp Thr Gly Leu Arg Cys Arg Ser Cys Ser Gly Asp
        435                 440                 445

Val Thr Pro Ala Pro Val Glu Gly Val Leu Ala Pro Ser Pro Ala Arg
    450                 455                 460

Leu Ala Pro Gly Pro Ala Lys Asp Asp Thr Ala Ser His Glu Pro Ala
465                 470                 475                 480

Leu His Arg Asp Asp Leu Glu Ser Leu Leu Ser Glu His Thr Phe Asp
                485                 490                 495

Gly Ile Leu Gln Trp Ala Ile Gln Ser Met Ala Arg Pro Ala Ala Pro
            500                 505                 510

Phe Pro Ser
        515

<210> SEQ ID NO 2
<211> LENGTH: 12382
<212> TYPE: DNA
<213> ORGANISM: Homo sapiens

<400> SEQUENCE: 2 cgcggggta taacagcggc gcgcgtggct cgcagaccgg ggagacgggc gggcgcacag      60
ccggcgcgga ggccccacag ccccgccggg acccgaggcc aagcgagggg ctgccagtgt    120
cccgggaccc accgcgtccg ccccagcccc gggtccccgc gcccaccca tggcgacgga     180 cgcggcgcta cgccggcttc tgaggctgca ccgcacggga atcgcggtgg ccgtggacag    240
cgccttccca ctgctgcacg cgctggctga ccacgacgtg gtccccgagg acaagtttca    300
ggtgggctcc ccgcccgccc ccgctgccc caggccctg tgagccaggg atagtccccg      360
gggaagttcc aggaggaccc cgcccctcca gatccccaag cccctccagc cttcccgaac    420

-continued

```
tccctcccca caaggagcca ggggcgtccc tgatgacaag ttagaagttg gtccccttcc      480
cccagccgtc cccacacctc accccccaagc caagggaatg ccctccaggt tcccccagcc     540
ccaccctcaa caccccctaca ccaccacctg actccaccac aagccgagga gatgggcgtg    600
gagctgtcca ggtcgccagc gcctctgcct gggagctcca ccctctagtc atgatggaga    660
tgggcaggcc gcagggtgtg ggggaccatg gcagggaccc tcatgccacc ccactgcagg    720
agacgcttca tctgaaggaa aaggagggct gcccccaggc cttccacgcc ctcctgtcct    780
ggctgctgac ccaggactcc acagccatcc tggacttctg gagggtgctg ttcaaggact    840
acaacctgga gcgctatggc cggctgcagc ccatcctgga cagcttcccc aaaggtgggt    900
cctggtggac tcagccatgc tgggggcctg ggcagctgc tgtcacctgc tcagcccagc    960
tggactggaa ccggagtggt gtttgaggag cccgtgggtg atgttccagg accgtcttgg    1020
atcctaagag gcaaaggggc caggcctcac ctgtctggcc aaggtgtcca gttctggggc    1080
ccacccctacc cctggagaaa accctgaggt tgggaccctg ctcctgcccc tgagctgcag   1140
atgtggacct cagccagccc cggaagggga ggaagccccc ggccgtcccc aaggctttgg    1200
taccgccacc cagactcccc accaagagga aggcctcaga agaggctcga gctgccgcgc    1260
cagcagccct gactccaagg ggcaccgcca gcccaggtac cctccctgca ggggaagcca    1320
gccagggtct ccagtcttcc cgggcttccc cgggagccca cgccccctcc ccacccgggc    1380
tcccacccac tgggtgtggg gccagcctgc ctggggctgt gggggtctcc tctgggtact    1440
agacccacac actggaccag cctctcagct ccctcctgcc tgaaggctga gctccccgga    1500
gctggtgaag taggcgggcg ggtctcattt ccctttact gatgagaaac cagagcccgg    1560
caaagggact acccagcact ggaccgcccc ctccacgccc tcccaccgcg ggcccctgcc    1620
caccggcact caccccccact gagaggggag gccaggctgc cccagctcc cccattcagg    1680
ctctcaactg aaggccaagc ccccaagaa gccggagagc agcgcagagc agcagcgcct    1740
tccactcggg aacggtgagc ggggcccagt gggagcgcct ccccttctccc tggccagggg    1800
caaggggtca ggggtcagag cagggcctgc cctctgagac cctgtcctag ggctgggga    1860
cgtgctggcc tggtgtgtca ttccaagggc ctaagctgca ccaccagacc caggaagggg    1920
acaccttggg tctaagcatg atcttgccag tcgcccctgc ccccactgca ccctggttct    1980
gggacccccct tctcaggcac cttctctgcc cgtccactcc ctatccttca ggaccagcct    2040
agacatagct tcctccagaa aatcatccct ggccccccagc tgcatgcagg ctgaacccct    2100
cctgtcccct tctccttcct tcccagggca ctggactcca gagacccccct atctccctga    2160
gggcagagcc taggaactct gtgtccctcc cggcacaata cagggcccat gtcatggggg    2220
ggtgggtctg gtcattggtc atgccttcct atccattgtg ccagctctgc tgacactgcc    2280
accccccagc acacgcacac ttgggtgcac acacgaacac acacattctc atgtctctgc    2340
acttacctgt gggctgtctg cacatggcag ggctgggtcc cctccttggc ctgccctggc    2400
tggaaggaaa gggctctgca gcccagtgct gcctgcttct ggcatagagt atgtgcttgg    2460
gaacagtctt ccccacgggt gaccccaatg ggtgttccct ttcccaggga ttcagaccat    2520
gtcagcttca gtccagagag ctgtggccat gtcctccggg gacgtccgg gagcccgagg    2580
ggccgtggag gggatcctca tccagcaggt gtttgagtca ggtagacgct gtggcgggga    2640
gatgggcctg atggggagac ccaggctcca agatggaagg aggaccacgc cccttttgcat    2700
cctggtggtc ccacagcaga ccggactgtt gctcaggtag ccagagtttc tgcctgtggt    2760
tctgctgact ttggaggagg agggtgagca ctgaagtctc cctgtcgggg gaccttctgc    2820
```

```
aaggccagcg gtccaggccc acatccccac ccgggatgta cagcactccc cagtcacctc   2880
catccatgtg catgggccct cctgggccat ggggttgcat ccttagaaag ttctgcctgt   2940
gctgctgaga ccctccaggg tatcggcatt cttcaaccag gacagcctgt agcatagcgt   3000
ccttgccccc catacccctgg ccagcctgca gcatcctcgc ccgccattcc ctggccagcc   3060
gctgacccca tgcaatcacc agtgccatct gaccagggca cagcagggcc gctggtggca   3120
gacccaccgt gccatcgggg cattccatct caagtccctg acacggtgtc tcctcggtgc   3180
tggacatggg ctgggaacac caagcacagc cagggccctg gtcttgcacc tctggatggt   3240
cccaaggccc actgtgttac ttcctaaggc tgttggttaa attggcacaa actgggaggc   3300
ttgaaatgac agaaatgcca acatcgaggt gtctcggggc cacactccct ctggaggctc   3360
cagggaagaa tccttccttg tgtctcccag ctgctggtca ttatgggggt acccctgtgc   3420
tccttgttcc tgggctcagg acccaccgct ccagcctctg cttctgtggt ctcacagctg   3480
tctcccacgt gtcctcttta taaggacacc agtcattgaa cttatggtcc agtgtgacct   3540
catcttaact aatcacatct acaaagaccc tgatttcaag taaggtcaca ctctgaggtt   3600
ctgggtggac gtgaacttcg ggggacgctg ttgaacaccc tggtgtagat ccaggacaat   3660
ccccgggccc cagactcgac tggggtgggg gcgggctgga ggaatgcagg ctgtgggaac   3720
tccacctgtc tctgctagac cccacccctgg ggcctacacg actgcaaagg caggtcctgc   3780
tgggcgggtg agccaggacc agccggcatc tcctcccagg cggctccaag aagtgcatcc   3840
aggttggcgg ggagttctac actcccagca agttcgaaga ctccggcagt gggaagaaca   3900
aggcccgcag cagcagtggc ccgaagcctc tggttcgagc caagggagcc cagggcgctg   3960
cccccgtaag cacctgacct tccctgggga gcctggctct tgatgccccc cgccccagga   4020
acagcgttgc ctctggggga gtggctctgc tgggggctgg gggctgctgc cgagagacgc   4080
ctggtgccac agccatgtgc accctcgctg ctgaggctgc ccccattgct gacgcccctc   4140
ttccttgcag ggtggaggtg aggctaggct gggccagcag ggcagcgttc ccgcccctct   4200
ggccctcccc agtgaccccc agctccacca ggtaatgccc tagaccacag gagaggcccc   4260
tgtctgccct tgctcccctc gggtgggtcc tgctgcctct gcctttacct gggcactcag   4320
ggatgagcac cggggcctga gcccctaccc acagggtaca gctcttttttc tttaatagac   4380 agtattttttt tcctgataat acgcaatggt aatagtttaa atgagtcaga gaaagtgagg   4440
tcttctcagg ctcttaagag catggcgttt ggtccaggct gtaccgcctg ctctcagctg   4500
ggcccgtggg tgggccgggc gcccctgcta tagccaggag gtcaaggatc cactgggaat   4560
gccatgctca tctttcgtcc ccagcatggt ttcttaatgg ggtagaagca gtgtgggggg   4620
tgcctgccgt ggtgggttac agatcttgac cacttggcac caggggctct gtggggccct   4680
ggcacttagc agtgacagga gccagtcctg ccctgcagga gcacccgggc tggtgggcgt   4740
ctgggggatt gttagaatga gtgaggtcat tgccgtgcag gaccagccta gcctggctgt   4800 ctgggggggat tctggaggaa gtggtacctg ggagacccct gaaggcacag caggcaccat   4860
ccaggcaggg cacaaggacg gtgggggctg caggtggagg attcagcagg cgctgaggtc   4920
gggagagacc tccctgggcc tggccccact gccctgtgag gaagggttca tgtggttggt   4980
gtacagttcc ggggcccctg gaacgcagca gcctgcaaga aaccgggttt tcttcccaat   5040
agggatggcc ccgggggggtg tctgttggag accagatgga tggggaacag gtggtcaggg   5100
cagaatttca ggccctggca gcatgggagc agggcagaga ctggggagtt caggtaccca   5160
```

```
gagatgctgc tggggagct gttttgggaa ggaggtggct ctcaggaggg tgctgcaccc    5220
cagcccagtc tgcatgggcg tctcttgcct gtgccagaag aatgaggacg agtgtgccgt    5280
gtgtcgggac ggcggggagc tcatctgctg tgacggctgc cctcgggcct tccacctggc    5340
ctgcctgtcc cctccgctcc gggagatccc caggtgagcc tgcacctctg ccagcgcaac    5400
caggccaccc cggttcacgg ccgcctccac ccactgaccc tgaagggaag ccaccccaag    5460
cctctcccat ccaagatgga aagggttct gagtcaggtc actgggccgt ggggccgggg    5520
cctggggttt tcccacccctg ccacctgcct cccggtctgg ccacacctgc tgcccagcct    5580
ggacagctgg gcccctgagg gcagcaaagc agaacagagg cccagggcga agatgccacc    5640
ctgtccaagc tcatcccagg ctgcagccca cgccccatg ggtagccggc ccccaccccc    5700 aagcccacc ccagagtccc actccagaca gggctgggga gcacagaggc cacagagctg    5760 tgcccccag gcaggtggg agtttgtcca ccaatgcaca ggacgccggg cttagtgggg    5820
gcgggaggcc tcctctgcgt tcacatcccg gtgctccttc cccacggccc accgagccct    5880
gcccccattc caaccccaca ggacgtgca gtctgtggga ggaagagctc tgggtgcagt    5940
ggggacccac gttcaggcga ggctctgccc cagcccctga gtggccgtca tcaggcccc    6000 tctcagcctt gtgcctcatc actagaataa ggggcacagt gggggtcatt gctcggctcc    6060
tgaagccgtt cctccttgcc gtctctttct gcccttgatc acctccccat tctgctgggt    6120
gccattcccc ttaacaggtg ggtcagttta gggaggcccc cggcagggcc cagccctgag    6180
aggcaggcaa agccaccagg gctcgcaggt gttggggatt cctggggttc atcagagagc    6240
acgccaaggg gaccctgatc acgctggcca gggccaccc acgaagggta aatgtccccc    6300
tgctgggctc tcccttcctg tgtctctgcc catctctctg ctgtgcctcg gttcccctc    6360 tgtgaaaaga catggtcgga gccctggagc tccacccgtg ggtttgggga tctgtcaccc    6420
gctgtcttgt tctgcatgtc tctgactggt ggacacacga gcagtgggac ctggaggtgc    6480
tccagctgcc tgcaggcaac agtccaggag gtgcagcccc gggcagagga gccccggccc    6540
caggagccac ccgtggagac cccggtatgg ccacgccccc tcctagccgg ccaccccctc    6600
ctgtccacat ggccacgccc cctcctaggc tgggccaccc cctcctgtcc gtctgtcccc    6660
tggagtcctg tgggacagga ctgccccagc catagcacta tgtccccat gcccaagccc    6720 ggtccttgtg gtctcctgca gtggagtccc catcatggtt cctgtgggcc taaacccagc    6780
tctcctggct gcgggtccac cccgggggc actatgagca ttgataacgg ccccggaaga    6840
tgtgttcctt gttctgctgc tgtgagggta gtaggtctac tgtgcacaga cccagtgttc    6900
cctctgacag ccctgagggc caggggccc cccgtgtgta gacggggag agggaggac    6960 cacagagcca ggaagtgcca cagccttttcc cactcagtgt ggacgccttc caccatgcca    7020
gccctccgcc ccaccatgc caggcctctg ccccaccct gctgccctgg gtttcagggt    7080
cccagcagtc actgactcct gggtggtgcc gggcaggcgc ccgctgcccc tctgatgctg    7140
acccttgggt tccagctccc cccggggctt aggtcggcgg gagaggaggt aagaggtcca    7200
cctggggaac ccctagccgg catggacacg actcttgtct acaagcacct gccggctccg    7260
ccttctgcag cccgctgcc agggctggac tcctcggccc tgcaccccct actgtgtgtg    7320
ggtcctgagg gtcagcaggt gagcggggag tgggggtcag ggtgggctct tcaaggagcc    7380
caggacctac ggggcggatg aattcacctg aaacaggagg agagggaggc caggcgagaa    7440
aggctccggg aggcacaggg cctggggctg tggggggagc gtggggggct gcggggggaa    7500
ggggacgctc ctagacctcc actccagctc ctggccctgg gcattactgc tccccccaca    7560
```

```
aggcaggaca atgaagggga ggatgtccca gcacacgtgg gagccctccc ctccctgcct    7620
caattcccctt ccctgcaccc ctgtgggcac cgcctttcag gagactcccg cactcagccc   7680
caaaggaggc caggcccgcc aagcaggaga gaggtgcggg cgccaggctt gcaggcagca   7740
gcctgagggt gcttgggtcg cccctgcctc ctggggatgg gactggtccc gctgtcctgc   7800
agcctgcgtg gcaccgtgag gctcctcact tgcgcctaga cccgccgtcc agccctgggt   7860
ggtcccaggg gagagcgcac agggctcggg ttcgggttca gctacatttc ccccggcccc   7920
ccgcgtcacc ccgcgctgtt gcctcccaca gaacctggct cctggtgcgc gttgcggggt   7980
gtgcggagat ggtacggacg tgctgcggtg tactcactgc gccgctgcct tccactggcg   8040
ctgccacttc ccagccggca cctcccggcc cgggtgagtg agcgtggtcg gcggggaggc   8100
ctgaacccac acccacaccc tacacccac cccacactcc ccaccacat catacagccc    8160
acaaccacac cccacccaca cccacactc ccacccacac cttgcacccc accccacacc   8220
catgccctgc acccacaccc tacactccac agccacactc caccacaccc cacccacac   8280
cctactcccc acctcataacc ctgcacctca ccacactcca cagccacacc caccccaca   8340
ccccacactc ccacccacac cctacaccca cccacacccc tacacccaac ccaaacccac   8400
ccaaacccac cactcccact ctccacccac cccacacccc cttcctcaca ccccacaccc   8460
ccatccccca ctcaccaccc acgcccacac cccacacccc ataccccgga ggtggcactc   8520
ctgctccccc ccagggctgg cagcccctca tcctctgctg caggacgggc ctgcgctgca   8580
gatcctgctc aggagacgtg accccagccc ctgtggaggg ggtgctggcc ccagccccg   8640
cccgcctggc ccctgggcct gccaaggtca gtgccgcagg ggccctccat gcatgccggt   8700
gctggggggtg gggaacccct tgggttggtg ttgggggagc acatctcagg gcagaccctg   8760
ggtgccagct tcgagggctt gcaccagacg cactgaccat gtgctcatta tctgtagaaa   8820
atatttcccc tttaaaccaa ttcttttttgg caacttaaat atagttaaaa aggaagctcc   8880
ccccgagggt tggtggctga cgtcacggtt ggctgtgtgg ccgcctcaca gcatgagcct   8940
gagagtcctg ccagggctcc ctggtggggt aagggagag cgggagcgcc cggcctgcag   9000
gagcaaaccc ccaccctgtc tgaccccttcc aggttgtctc accccagcc ctccctgggg   9060
ccaggatcca ccccactgtg tggccagagc cctctcagag aggcaaagtg accccgggtc   9120
cagccagtag ctcttcctgt cctcctgctc cggggtcaga gaggacctgg gtggcgcgga   9180
gaccccctgac tgctggggcg gctgggcttg ccctggagct gggtgtgggg gaggcccgag   9240
tcgctgctgc aggagcctcc gggggggtgg cctcttgccc tgaccgtccc cagcagaggc   9300
ctcctgagca catcctggcc accgaggagc ctttagggat cctggggtga tgacacgtcc   9360
cacctgctcc actgggcccat gctctttccc agctgtgcct ccgccccgta tacaccgtgt   9420
gggtgacagg ccaccccggc gtggtactcc ccaggagggt gacagcctac cccagcgtgg   9480
tactccccgg gcaggtgaca ggcttccccg gcatgcaggc tctggcctgg catggcacaa   9540
gcctcagacc cagccctgcc cttggggctt ttgtggaaca gtggcgtggc ccacagctgt   9600
cactgtcccc ttccttctag aagcctccct cctcacacca cccatctgga gtcaggagcc   9660
cagccgggca tatacgcaga tgcccctccc taacccccagg cagctttcct gcaactgctc   9720
ccgcagcggg tacctcgtca ttaacctcct gggttctgtc tctgaacagc agagacctct   9780
ttcttgtcat cgtgatgtga aatgtaacgc catgtcagag gaaaagttct ggctggcctt   9840
ggcctccccc ctcagcctgc ccccttcctc cagggtggtt ggacgtggcc ccagaccca    9900
```

```
tcctgagcag ctctcccacc ccctgggagc atccttagga ccggggagca tccaggggct   9960
ttcccctcca gaccgggcag cccctccctc agccatgcag ggctgccggg cctcgcagcg  10020
ccagtgttca cccgagtgga ggagctggga tgtggctgtt tggggccaca aatggggaat  10080
tccacagggt tcaatgtaat atggtctcct ctctgctggg ggtgcctgcc tgggaccttt  10140
ctcccactct ggtcgctcac ctatagtgtg ggctggccct ggtggtgctt gtcggggcg   10200
ggggtggcat ggaccaggca ctttcctctc tgggcctcag acttcccctc tcagagtggg  10260
actccttgct ggttccctga gctccctcgt tttccccagg aggccacaca gtgtggaggc  10320
tgtctggggg ccgtgggcag ctggccgtgg gcaggaccct ggggaggcag ccccagcccc  10380
atcatgccca cgcagccctg tgcccccacc cccagtggag ctgggtgtaa gaattcccat  10440
ctcagtgtgg gggaaacacc cccgcggccc ctaggccctg cggcctctgt accccacca   10500
gggctgtggg agttgggctg acctcttctc tttactgggt tccaggatga cactgccagt  10560
cacgagcccg ctctgcacag ggatgacctg gagtcccttc tgagcgaggt aacgcctccc  10620
ctggcctcct ggtgctcctc cactcccccc tccctgcctc agccggcacc caggctcccc  10680
actctggggg aggactgccg gcccccactg ctcttgagcc gtggaaactc aggctgtccc  10740
tgctccaccc accaggagcc ccagtgctgc tgagcacctg gcaccccca caggagcccc  10800
cctagccccc ttgcaggagc ccccccggc cctccccct gcgggagccc agtgctgctg  10860
agcgccccca gcccctcccc aacaagagcc cccacacggc ccctccctg agggcctgca  10920
ccctggcagg cagaggctcg agcaccaggc tcaagatcca cttcccagg gagggtgggg  10980
cgtgggagtg ggggggggt cccagacccc gtccctctaa gatttgcttg ccctcccaa  11040
ctcaggcctc tctacgctaa gatgggcagg tagaatctgt ggggaaaatg tgactttaa  11100
gggctctgtc tgttttgcc aagaggataa gctccttcag cctccacggg ttctcctcag  11160
tgtctgatgt ggcacccggg ggtcccagct gaccatgggg caggggttct gccctgtgca  11220
gtggccgtgc cccacacacc ctgaccgtgc aggtgtctgc agagcccag ggcctgagag  11280
tgggccaggg ggcccagcgc tgggtaatgg agctgcccct ctggatgggg tcccgggta  11340
tagctggaga aatgagcgac gggctcacag cctctcccgg gtggcggtct tattctgctg  11400
gcatcgtggg gcccgtggcc ccatcctgtg ggagcatcag gctcctgagc agaataagta  11460
gctggcccg acccccccac cctgaaggag ccacccgagg aggcagaact gccatgaact  11520
gccatgggga tgtgccctgg gcttatagga tgtggtgaag tacacaggac agggtcctcg  11580
gtctggcctg tgccatgggg accttgggcc tcagtttccc caccttttgat ggaatacggt  11640
gaagtgcaca ggacagggtc ctccccagac tggcctgtgc catgggggcct cgggcctcag  11700
tttcccccacc tttgacttag agggaaggtt ggatggtgac ttcttgtaac gatggccatg  11760
attctgtggc tgcggcgggg gcgcacctgg aggttctcac cgtcactctg tcccgcagca  11820
caccttcgat ggcatcctgc agtgggccat ccagagcatg gccgtccgg cggccccctt  11880
cccctcctga cccagatgg ccgggacatg cagctctgat gagagagtgc tgagaaggac  11940
acctccttcc tcagtcctgg aagccggccg gctgggatca agaaggggac agcgccacct  12000
cttgtcagtg ctcggctgta aacagctctg tgtttctggg gacaccagcc atcatgtgcc  12060
tggaaattaa accctgcccc acttctctac tctggaagtc cccgggagcc tctccttgcc  12120
tggtgaccta ctaaaaatat aaaaattagc tgggtgtggt ggtgggtgcc tgtaatccca  12180
gctacatggg agcctgaggc atgagaatca cttgaactcg ggaggtggag gttgcagtga  12240
gctgagattg cgccactgca ctccagtctg gtcggcaaga gtgagactcc gtctcaaaaa  12300
```

-continued

```
caaaacaaaa caaaaaaacc acataacata aatttatcat ctcgaccact tttcagttca    12360
gtggcattca catctcatgt aa                                              12382
```

<210> SEQ ID NO 3
<211> LENGTH: 552
<212> TYPE: PRT
<213> ORGANISM: Mus musculus

<400> SEQUENCE: 3

```
Met Ala Gly Gly Asp Gly Met Leu Arg Arg Leu Leu Arg Leu His Arg
1               5                   10                  15

Thr Glu Ile Ala Val Ala Ile Asp Ser Ala Phe Pro Leu Leu His Ala
            20                  25                  30

Leu Ala Asp His Asp Val Val Pro Glu Asp Lys Phe Gln Glu Thr Leu
        35                  40                  45

Arg Leu Lys Glu Lys Glu Gly Cys Pro Gln Ala Phe His Ala Leu Leu
    50                  55                  60

Ser Trp Leu Leu Thr Arg Asp Ser Gly Ala Ile Leu Asp Phe Trp Arg
65                  70                  75                  80

Ile Leu Phe Lys Asp Tyr Asn Leu Glu Arg Tyr Ser Arg Leu His Ser
                85                  90                  95

Ile Leu Asp Gly Phe Pro Lys Asp Val Asp Leu Asn Gln Ser Arg Lys
            100                 105                 110

Gly Arg Lys Pro Leu Ala Gly Pro Lys Ala Ala Val Leu Pro Pro Arg
        115                 120                 125

Pro Pro Thr Lys Arg Lys Ala Leu Glu Glu Pro Arg Ala Thr Pro Pro
    130                 135                 140

Ala Thr Leu Ala Ser Lys Ser Val Ser Ser Pro Gly Ser His Leu Lys
145                 150                 155                 160

Thr Lys Pro Pro Lys Lys Pro Asp Gly Asn Leu Glu Ser Gln His Leu
                165                 170                 175

Pro Leu Gly Asn Gly Ile Gln Thr Met Ala Ala Ser Val Gln Arg Ala
            180                 185                 190

Val Thr Val Ala Ser Gly Asp Val Pro Gly Thr Arg Gly Ala Val Glu
        195                 200                 205

Gly Ile Leu Ile Gln Gln Val Phe Glu Ser Gly Arg Ser Lys Lys Cys
    210                 215                 220

Ile Gln Val Gly Gly Glu Phe Tyr Thr Pro Asn Lys Phe Glu Asp Pro
225                 230                 235                 240

Ser Gly Asn Leu Lys Asn Lys Ala Arg Ser Gly Ser Ser Leu Lys Pro
                245                 250                 255

Val Val Arg Ala Lys Gly Ala Gln Val Thr Ile Pro Gly Arg Asp Glu
            260                 265                 270

Gln Lys Val Gly Gln Gln Cys Gly Val Pro Pro Leu Pro Ser Leu Pro
        275                 280                 285

Ser Glu Pro Gln Val Asn Gln Lys Asn Glu Asp Cys Ala Val Cys
    290                 295                 300

His Asp Gly Gly Glu Leu Ile Cys Cys Asp Gly Cys Pro Arg Ala Phe
305                 310                 315                 320

His Leu Ala Cys Leu Ser Pro Pro Leu Gln Glu Ile Pro Ser Gly Leu
                325                 330                 335

Trp Arg Cys Ser Cys Cys Leu Gln Gly Arg Val Gln Gln Asn Leu Ser
            340                 345                 350
```

Gln Pro Glu Val Ser Arg Pro Pro Glu Leu Pro Ala Glu Thr Pro Ile
        355                 360                 365

Leu Val Gly Leu Arg Ser Ala Ser Glu Lys Thr Arg Gly Pro Ser Arg
    370                 375                 380

Glu Leu Lys Ala Ser Ser Asp Ala Ala Val Thr Tyr Val Asn Leu Leu
385                 390                 395                 400

Ala Pro His Pro Ala Ala Pro Leu Leu Glu Pro Ser Ala Leu Cys Pro
                405                 410                 415

Leu Leu Ser Ala Gly Asn Glu Gly Arg Pro Gly Pro Ala Pro Ser Ala
            420                 425                 430

Arg Cys Ser Val Cys Gly Asp Gly Thr Glu Val Leu Arg Cys Ala His
        435                 440                 445

Cys Ala Ala Ala Phe His Trp Arg Cys His Phe Pro Thr Ala Ala Ala
    450                 455                 460

Arg Pro Gly Thr Asn Leu Arg Cys Lys Ser Cys Ser Ala Asp Ser Thr
465                 470                 475                 480

Pro Thr Pro Gly Thr Pro Gly Glu Ala Val Pro Thr Ser Gly Pro Arg
                485                 490                 495

Pro Ala Pro Gly Leu Ala Lys Val Gly Asp Asp Ser Ala Ser His Asp
            500                 505                 510

Pro Val Leu His Arg Asp Asp Leu Glu Ser Leu Leu Asn Glu His Ser
        515                 520                 525

Phe Asp Gly Ile Leu Gln Trp Ala Ile Gln Ser Met Ser Arg Pro Leu
    530                 535                 540

Ala Glu Thr Pro Pro Phe Ser Ser
545                 550

<210> SEQ ID NO 4
<211> LENGTH: 13589
<212> TYPE: DNA
<213> ORGANISM: Mus musculus

<400> SEQUENCE: 4
agcaccacga cacccaagga agggagaagg gaacgcaagc gcgcgtgggc cagcagggg      60 cgccgaggcg cagcccctgt gaggaagatg gcaggtgggg atggaatgct acgccgtctg    120
ctgaggctgc accgcaccga gatcgcggtg gccatagaca gtgcctttcc gctgctgcat    180
gctctagccg accacgacgt ggtccctgag gacaagttcc aggtgggctc cagtcccgcc    240
cccggtgcct ctcattctcc ccactcctcc acccgcagac taggtgttcc ctcccaacct    300
cagccaaaac cctatactat cccatacccct ccccctacca gccaaggagt ggtcccaagc    360
cctcctcagg agacctctcc agatcaagtc ccaggtgagt tccctaacct cacaccctat    420 gcccctaac tgctccaggg cccagggata gacaggaata gcaagtctc ccttatccca    480 aagaggcagg agttggagaa tgatatgccc aggtgcccaa tgctgtcact gcaggagacg    540
ctccgtctga aggagaagga aggctgcccc caggccttcc acgccctgct gtcctggctc    600
ctgacccggg acagtggggc catcctggat ttctggagga ttctctttaa ggactacaat    660
ctggagcggt acagccgcct gcatagcatc ctggacggct ccccaaaagg tgggcgtgtg    720
ctgattgatg ctgctgagctga tgctcagcca atgggtagca tcggggatat ggatacaagt    780
cggcccatgt tttcagggag ccactagaac ttgggcagat cctaagaagc aaagggcaga    840
ggtctgctct ttctcgtcct caagagtgcc ccattctaga gctcaccctg aagataaggc    900
tttaagacag gaccattgtt cctgcccctg agctgcagat gtggacctaa accagtcccg    960

```
gaaagggaga aagcccttg ctggtcccaa ggccgcggta ctgccaccca gacccccac    1020 caagagaaaa gcactggagg agcctcgagc caccccacca gcaactctgg cctcaaagag    1080
cgtctccagc ccaggtacac tcaagaggag ctagccaggg ttgctgggcc ctccccaacc    1140
ggctcttagg agcttctgtc ttactgacac caccccaggg ccagcctgcc agggtcacag    1200
agtcacctct gagccctcag acctgagcat tggaggaggc ccacagcctc tcagcgtctt    1260
actgtcccaa aggctgagtt tctgggcggt gaggcaggca ggtggttttg atttccttc     1320 tgttgaagaa ggaaacagcc catcacagct taagaaccgt cgatctgacc cttaccagct    1380
gctctctctc ccatcctcac tttctaccct ggatccgtca acatgacccc agcccagaaa    1440
agtgggccca ggctgcctct acctccccc cgcaggctcc cacctgaaga ctaagccccc     1500
taagaagcca gatggcaact tggagtcaca gcaccttcct cttggaaacg gtgagttagg    1560
ccaagagtgg aggttggagg aggtctgatc ccattgacct cagctggatg gcaaagccag    1620
agaaagatag ggactcctta gatccaactg tcttgccatt ctcctaccca caatgccctg    1680
ggtgtctcct cccagacctc tgcccatttt aatgctccca atcttctagc cagcccagaa    1740
aaagaaccac aaggaaaacta tccctgttcc tcagctgcgc ccaaccttga ccacacccac    1800
ccaccatcca ccatccacct gtgcttcctg gtcctcaccc cctgatggcc taggaactct    1860
gtgccccaga ataacgcagg tcccacgtca ccatgagatt cttgtcaatc tgccattggg    1920
ctcaacatga ccaacactgc tgtccccacg gccgtgtgct catgcacata cgtctacttg    1980
tgtcaaaccc tctccaggaa ttcagaccat ggcagcttct gtccagagag ctgtgaccgt    2040
ggcctctggg gatgttccag gaacccgagg ggccgtggaa gggatcctta tccagcaggt    2100
gtttgagtca ggtaaatgca tggaagcagg ctgccaggga gacccagatt tcaaaatgga    2160
agggagtgct tctagagcat ccatggccgt ggctgagggc aaggcagcca gtgtgcttca    2220
ttcaggtctg ctggctttgg agcccagtgc tgatgtggaa gactccctac atgggtggat    2280
cttttgtcag gccagtggtt catagtcaca ttcagccatg gaatgccacc tcttccacgt    2340 caagggggtgc tgctagtcac aggggacatc ctaagtttcc ctgtgtgctc tagttctgtc    2400
aagagaccat agtgcccact aagacagccc accacatcct actgccctgt gtcaggtatc    2460
tatgtcctgt ccagtcccct cactctttgt ccaggttcct cccacaattg cctacctaca    2520
aggctggcta gtggggtcac cttatacagc cacccagatc atctgaacaa gtcagagctg    2580
gggccagaca cactcaccat tgcagaatct gctccacagc acctcctctg tccgggacac    2640
tggacttgga tgccatggac agccagaatg gcctgggagc tcatgccagc cctagtcaga    2700
gcagccccaa gaatcttgtc tgactcttct ggggttatta gaacaaaaag ccccaggctt    2760
gtaacaacag gttccaaagt caaggtgtgg gaagggacac gtcccttcgt gggctttgga    2820
gggtccctct gttgcctcta gcatgaagtg ctgttggaat gcttacttct gagaatagcc    2880
cctctccaat ctgactattc ctctctgact tcacctttct ttgtaagaac attggattta    2940
agggctagta tgacattttt aaaaaagat ttatttaatt tatatgagta cactgtagtt      3000
gtcttcagac acaccagaag agggcatcag atccccatta cagatggttg tgagccacca    3060
tgtggttgct gggatttgaa ctcgggacct ctggaatagc agtcagtgct cttaaccact    3120
gaaccatttc tccagcccgt atgacatctt ttttgttgt tggttttct gtttggttgg       3180 ttgcttcttt tgttcgtttt tgtttgtttg tatttgagac agttcctctg tgtagctttg    3240
gctgtcctgg aactcactca ctctgtagta gagcaggctg gattcgaact cgagtagatc    3300
tgcctgcctc tgcctcccaa ggattcaaga tgtgtaccac catgccctgc tatgacatca    3360
```

```
tcttaactaa ctctctcgcc aaagaccctg tttccagtaa ggtcccgttc tgagcttgtg    3420
aggaagggca ctgtttaagg gtacagtcac cagcaaagaa tccctagctg tacccagccc    3480
cggttctgcc agaccccag ggtgagctca ttcagtctat ctctctccca ggaagatcca     3540
agaagtgcat tcaggttggg ggagagtttt atacacccaa caagttcgaa gaccccagtg    3600
gcaatttgaa gaacaaggcc cggagtggta gcagcctaaa gccagtggtc cgagccaagg    3660
gagcccaggt cactatacct gtaagcctta tccagcatgt ccatttaggg ggagctgggc    3720
cttccttcca tagcctcccc tcccctcccc tcccaaagaa agcctggagt tcttcccgag    3780
ggtgggagtt gcttcccagt ggtacttggt ggccacatag atcttccctg accctggcta    3840
cttcgttaag accctgtgtc tctcataggg tagagatgag cagaaagtgg gccagcagtg    3900
tggggttcct ccccttccat ccctccccag tgagccccag gttaaccagg taagtcccaa    3960
gaagggggtg ggggtggggg aaccaggata tggagggcag ctcccttcct cttctctccc    4020
ttctctttcc tccacctcct cccactcagc tctttcttgg aagttttcaa ggatgcatat    4080
taggagattt ccaattagtc acagcaggtg agctgctttt aaaaaatca cacgttcagc     4140 tggttggtat atgcctttaa tcccagccct gggagacag gggcaggcag atctctgtga     4200
attggaggct agcctggtct acagagttcc gggacatcca gggctacacc aagaaaccct    4260
gtcttgacaa caaacaaaca aaacaaaaca aacaaaaca aaacaaaatc acacattctg     4320
tccagatgac aaaaagcaca ttagcttcgg gtcgggtagg gctgcagata aagcctgagt    4380
atggggattc tctgagggta tcaagttatc ctctcctccc cagcaccact gatgtggttg    4440
tgcctgcaat cattgattat tgagtccaac acctcagagc taggtactct gctggccccg    4500
gacaccaaag gttgaaggtc cagttctgcc ctgctccata aaagtgccct ggttattggg    4560
ggcctatgga cgtttcccat gtgctcactg tgtgggcccc cacaacctgg catctgggag    4620
cttcttgagg aggttcagac tcagaactcc ttccatcctg ataaggtagg ggatggggaa    4680
tgacaggagg tacctagggc taacgggaaa ccccgtgggc ccacccacct gctgtcctat    4740
taggtgagtg gtagtcaatc cagggaactg tgggcctccc cactctgtgg gttgtcagcc    4800
tgggctacac cgggactagc tatcaggagg cagatcaact ttacttaggg tgattcaagg    4860
cttttaaaaa aacaaaagat taatttatta tttattataa gtacactgta gctgtcttca    4920
gtcgcacgga tggtagtaag ccaccatatg gttgctggga tttgaactca ggaccttcag    4980
aagagcagtc agtgctctta cctgctgagc ccaattcaag gcttataacg ttttgggggg    5040
gggggtctga gggtaggaat atctaggatg ggcaaaggtc attggctggg ggcttggggt    5100
acctaaaatg tctccttagc aagggaaagc atttcggaaa tctcaggtgc tgaatgaatg    5160
ggcgctttgt caggagaaag gaagttggtc ctgtaattta actgaggcta cgtgacattc    5220
ttcatgcatc tctgagggca ttcctaagcc tggggggggg ggggcgggg gcgggctta     5280 gaattcccca gacaaggtca agaaggaga atcctgttta atgaagggag tcccccatat    5340
tgcgctgagc tcagaagcta tccagtcatg gtgggatttt gatcttaatt agcagagttt    5400
tcccactagg aactgcctgg cacccagcac tccttccaga gagggacacc ccctaggtc     5460 tgtgtggaac ctagtacttc agagaccttg cagagctcag gcaggggcca acgagagaac    5520
ccagggggaa cctggagtc agtccttagt ggtgagcatt gtcccaagtg ggtctctcag     5580
gtggatgctg tgttccattc tgggtccctc ttgcctggtc agaagaacga ggatgagtgt    5640
gccgtgtgcc acgacggagg tgagctcatc tgttgtgacg gctgtccccg ggccttccac    5700
```

-continued

| | |
|---|---|
| ctggcttgcc tgtccccacc tctgcaggag atccccaggt aagcagacct ctccatctct | 5760 |
| gatccatcac cgtccttatc cgctgacatt gaggaagcct agaagccttc acagaagaca | 5820 |
| gtaagggccc ttcagtaaga tctgtggaat gaatagggta ctagctatgg aaatggtagg | 5880 |
| attctctggc cataccgaaa cctatctgtg ttccctgcct catggcccac tcagggccaa | 5940 |
| caggccaaaa ggcagccata acatgatgtc cccaggcaaa ggtggccata tttgggcaca | 6000 |
| ggccttttcc taagcacact gtaccccac cccctcaaat ctcactcaca caatgatgta | 6060 |
| ctgttacccc tatcactgac tgcacaaccc tctgttctga ggagaggtaa gcagcagtct | 6120 |
| gtgcgggcta gcctgggctc tgacccaggt ctctctgatc ctcttccacc agggtccttt | 6180 |
| ccctcatctc ccctttccca ctggtccatc cctacaggac tgtgggtgtg ccaaggatgg | 6240 |
| aaacagtgta gctgagagtc atgcttatct cccctccccc actggcccat ccctatagga | 6300 |
| cggtttgtgc acctaggatg gaaacattgt agctgagaga gcccacagta atgccaggcc | 6360 |
| tatgacaagc aagcacaggt gctgaagggt actgggcata gagtattctt aagaattagc | 6420 |
| agagacccgc agggcatggt agtgcacacc tttaatccca gaactcggga ggcagaagca | 6480 |
| ggtggatttc tgagttcgag gccagtctgg tctacagagt gagttccagg acagccaggg | 6540 |
| ctacatagaa aaacactgtc tccaaaaacc aaaaaccaaa aaaaaaaagg attctaggga | 6600 |
| ccctgactct gtccagagcc atgctcccga ggtaaatagc ccacattcta ttgaactgcc | 6660 |
| cttatggtac ctaactcttt tagtcccggg tttggcttcc cacctatgaa tgagcatggt | 6720 |
| gacacagagg gtcctcaagc catccttgcc atacatttgg ggaagggggg gtgtctatgg | 6780 |
| tctctacttt gtctggcaag cctgtgacta gtgacctcct acacagtggc ctctggagat | 6840 |
| gctcctgctg cctccagggc agagtccaac agaacctgtc ccagcctgag gtgtccaggc | 6900 |
| ccccggagct acctgcagag accccggtat gccatattg ggtcacccc tttcttctct | 6960 |
| ctgactctct acagtcctat cttctggctt cacctgtgag tcctgcatgc ccgccatgct | 7020 |
| ctgttctggt gaattccctg tggggttgag gggccaaggg attaaaaaca gcttcccaag | 7080 |
| ctggctctgt ccctccagac tcaccactgc caatattctc caaaagcctt ggtagctctc | 7140 |
| ctgttagaaa cctagtttgc tctggcttgg ccctggcttt tgctgagaac catggaacca | 7200 |
| gccacacact cagcctttcc ttctcctcct cctcctcctc ctcctcctcc tcctcctcct | 7260 |
| cctcctcctc ctcttcttct cctagttttta ttttttaaag atttatttat ttattatatg | 7320 |
| taagtacact gtcactgtct tcagaaactc cagaagagag cttcagacct ccttacagat | 7380 |
| ggttgtgagc caccatgtgg ttgctgggat ttgaactcag aacctttgga agagcagtca | 7440 |
| gtgctcttaa ccactgagcc agttctccat cccttttttt ttttttttaat tttgttttgt | 7500 |
| tttatgtgta ttgatgtttt gcctgcatgt atgtctgtgt gagggtgtca agatcccttta | 7560 |
| gaactggagt tgcagacagt tgtgagctgt catgtaggtg ctgggacttg aacccgagtc | 7620 |
| ctttagaaga gcagccagtg ctcttaacta ctgagccatc tcttaagctt gtaccaagcc | 7680 |
| tcccaacct cagacccacc acagcagccc agtcctgact cctaggtgtt gctgagcagt | 7740 |
| accctgtggc ccctgaatgc taacccttga attccagatc ctcgtgggac tgaggtcagc | 7800 |
| ttcagagaaa accaggggcc catccaggga gctcaaagcc agctctgatg ctgctgtcac | 7860 |
| atatgtgaac ctgctggccc cgcaccctgc agctcctctg ctggagcctt cagcactgtg | 7920 |
| ccctctactg agtgctggga atgagggcg gccagtgagt gaggagaccc ctagggcctg | 7980 |
| ggtgctatct ttggggaaga ggggctctgg acctacggga tagttgtatg tccaaaacgg | 8040 |
| gacctctggt ggactcccgg ggctaggaat tagacggaca ttcctggggt caggggaggg | 8100 |

```
ctctgccaag agacacttgt tcatataata gtaacacagg gactgtaggg gagagcacca    8160
agggaactct ccagctgggc ctttgagatg gctcagtggg taaaagggtt tgcagccaag    8220
atggaagacc tgagttggat tcccaaaact cacatggtgg aaagagtgac tcggtctgca    8280
agtggtcctc tgatctccat gtgcatgacc accaataaat agtgaattag ctagaaagaa    8340
gggaaggagg gaagtaagac aggcaagcag gcaggcaggc aggcaggcag gcaggcaggc    8400
agacagacag acagacagac agacagacag gcttagcttg gttatccaga tgatacaccc    8460
tcccccatca tgaagcagga caacaaacat ctcgaatcca cagaccctgt ccacttctgt    8520
tggttacctt tctttttttc ttttcagag tccccacttt taaatttaat taattaattt    8580 atttattta cttattcact ttacatcccg ctcactgccc cttccccatc atcctctcgc    8640
agtctttccc caccctctcc ctcctccaaa gctcttctgg agtccacat ttggtaggat    8700 cagagctgga ctcccaggat ggactggtcc gtggaaagca gcttggaaag gccgctttct    8760 gaccctgct cccctcggga catccagaac tcagaattta cagtcccact cacgcgactt    8820
gaaaccctga ggtttcccag ttaacccggg ctggtggggt gagcaggaca cgggctgggt    8880
tgccgcccat gttgccctg cagggtccag caccaagcgc gcgatgcagt gtgtgtggcg    8940
atggcaccga ggtgttgcgg tgtgcacact gtgccgctgc cttccactgg cgctgccact    9000
tcccgacggc cgccgcccgg ccggggtgag taagggggca ccgggtggca gagtagccag    9060
cgatctcacc caccccgaag gttctccgag ccagtgagct tttcccactt ctctcggaca    9120
ggaccaatct ccgctgcaaa tcctgctctg cagactcgac tcccacgcca ggcacaccgg    9180
gcgaagctgt acccacctct gggccccgtc cagcacctgg gcttgccaag gtcagtgtct    9240
gctcagtcca ggtgagaccc tgtgggagtg gaggagaatt taaacccata tccaataacc    9300
gtgtgtccca ttactttttg tttggttggg tttgggggat ttgttttttg tttgttgttt    9360 tggattttg ttggtttgtt ttgttttgtt gaggtactac agatctctgg ctgtctggaa    9420
cttactcgta gaccaagctg accttaaact cagagatcca cctacctctg cctcccaact    9480
gctggaatta aaagcacatg acccttattc ctggactaac tttttgttt gttttaaaa    9540 attaatcatt tttaatcttt tttttaaaga tttatttatt attatatgta agtacactgt    9600
agctgtcttc agacacttca gaaaagggag tcagatcttg ttacagatgg ttgtgagcca    9660
ccatgtggtt gctgggattt gaactctgga ccttcgaag agcagtcggg tgctcttacc    9720
cactgagcca tctcaccagc cccccttttt tatcttttaa gatttctttt ttatttatat    9780
gagtacatcg tagctgcctt cagacacacc agaaagagggc attggatccc cattatagat    9840
ggttgtgagc gagccactaa gtagttgctg ggaattggac tctggaagat ctctccagtc    9900
cttgtttgtt tgtttggttg gttggttggt ttttcaagac agggtttctc tgtgttcccc    9960
tggctgtcct ggaactcact ctgtagacta ggctggcctt gaactaagaa atcagcctgc   10020
ctctgcctcc caagtgctgg gattaaaggt gtgtgccacc acttcccagc ccttgtttgt   10080
ttttttgttt gtttgcttta agactattgc tgggatcaaa ggtgtatgtc actaattctg   10140
gctcctcaat tacttttata aagtgttttt caataaacag acaacttatt ttgataagtt   10200
gaatctattt aaaagggaaa ggctggaagt ggtagggcag acattaacc ctagccccca    10260 gcagtaaaga taggttggtc tctgtaagtt agaatccagt ctggtctgta tcgtgacttc   10320
cagtttagtt agggctacgc agtcgaaccc tttctagaca taaccaagta ttttaaaggg   10380
aaaccttcca aatagctatg aactcactgt tggtactggg ttcctgggag tccgtgggcc   10440
```

```
tcagagctca gagctctgat cagggagctc tggacctaag agcagttggc ttaatttgaa    10500
atgagacgac tgggaggcac ccaggggcca gatcgtctgc agaacaggta tcagaatggc    10560
tgggacctcc agggcggcca actattggcc tggagagaga gagagagaga gagaaagaga    10620
gagagagaga gagagagaga gagagttggg gagcagagcc aaacaaagct gctggctttt    10680
gatgaccccg agagccacct acccaagtcc tctacccagg tggatctcta tgtcacctcc    10740
atttttacta accaggcagg gaccgagctt tgtctggagg cccaaggagg aaagggcagt    10800
atccacctct atccacttgc cattgcataa tactgctaag acagacatgg accccaggct    10860
tgggccccta gctgtctctc aggttcatgg gtaaaatgga gtgatcttgt aaagatgtgt    10920
tatgcaaggt ggcagagtgt atgcgcagct cactgctaga ttccagcttt ccctgataaa    10980 ttgccccccct agttgcaggt tgaccttatc tgattgagaa catctgggag ctgcatcag    11040 aatctattgc tcctaggatt ctactggagg acccagtaaa gcatgggca aggtttgctg    11100 agcctttaaa acagtggtcc tcagtgatcc tttggtgcca aatgatcttt tcacaggatg    11160
gcccaagact gttggaaata tctgagagtt gggattcgta acagtagcac aattacagtt    11220
acaaagtagc aacaaaaata atgttatggt gggggggggt gtcatcacat catgaggaac    11280
tgtattaaag ggttgaagca ttgggaagat tgagaaccac tgtcctagag tctagccaca    11340
aacagtgaaa gtcacttcta gaatgaagac gaggattgag caatggggcc tccactggct    11400
tcactgtgaa ctcctgacag agcctgccac tccctgactg gagctctgtc actatgccca    11460
gggcaggtcc aactaagttc agctcatgtg actagtgaaa gcagagagac actggctggg    11520
tgctagccac cgggtctctt tagggctac agggaatata taggacagat tgttgccctc    11580
agcctgcctg tgtccccagc ctgaggtact aggtgtgagt ctgctctgtg gtggagtaca    11640
gtctactgcc ccaagtcctg cgtctggtcc ctagcctgct gctaggttgg gttgactatt    11700
gattctctgc tttggttcca ggtaggggac gactctgcta gtcacgaccc tgttctacat    11760
agggacgacc tggagtccct cctcaatgag gtaatctgtc acctagtctg gctgtgctc     11820 acagattctt tgctgcccct agtaggcagc accagcagac cagtgttacc ctgccccat     11880 agctgctctt cctagaagag cttgtttcca tgtagggtgc tggcctcctc caggaacctc    11940
acatctggga tcctcacatc aagacctcag agccaggggg tttaagccct tgacttttca    12000
gggaaagctg ggagggtctt ccaggggcct ctctcttacc cctcccaact cagttttctg    12060
tttcttgagg tggataggtg gcccaggtct ttgattccca gtgcttgagg tagatgtagg    12120
aggactgtga ggtggatact aatctggact acattataaa accctatctc aaaaacctga    12180
ggggctacag aaatgcaaga gcattgttct ttcagaggac ccaagtttgg ggggggggg     12240 tcccagcagc catgtcaggt gacttttaac tgtttatcat tccactccag gggatctgaa    12300
acctctggcc tcctcgggca tctgtacaca catcacgcac acacacatac ttatacacac    12360
agacacacat atacacatag gtgcatacac acatgtacat acccactttt ttttttttt     12420 tttttttggt ttttcgagac agggtttctc tgtgtagccc tggctgtcct agaactcact    12480
ctgtagacca ggctggcctc aaactcagaa atccacctgc ctctgcctcc caagtactgg    12540
gattaaaggt gtgtgccacc actgcccagc atacatacat acttaaaagt agtaaattcc    12600
cagaaaccac atggtggctc acaatcatct gtaatagaat ctgatgccct cttctggtgt    12660
gtctgaagac agctacagtg tgtgtgtgtg tgtgtgtgtg tgtgtgtgtg tgtgtgtgtg    12720
tgaatattat gtgtatatgc atatatataa attaaaaaat agtaagaatg aatttcttct    12780
agaaaatgaa atagggcccc atctattgca agggcacaaa ctcctttggt cattcccata    12840
```

-continued

```
cccagggag cccacatgcc ttcttcagtg tccactgaca tttagggaga ctcaactggc    12900
tgagggacag agacctgccc tgggcagagg gccatgcaca ggcagatctg cagaagcacg    12960
agagagagag agagagagag agagagagag agagagagag agaggatcca gcatgggtgg    13020
acactggaaa aactgaggac cttctccagg acttcccagt cctgttggca gagaagaagg    13080
acccagcaga ggaagccaca cccagggccc acaggctgct ctagaggagg actggatcaa    13140
gagacctccc ttcactggca tgtcccatgg ccctagctc tcagtccccc tccttgaact    13200
agcgggtcag gttgggtgat accttcatgt caagatggct ctatgaggt gcgactgctc    13260 taacctcccg tgtcactctc tctcagcact catttgacgg catcctgcag tgggccatcc    13320
agagcatgtc acgcccgctg ccgagacac caccttctc ttcctgatga caggtggccc    13380
aggaaggggt gggcagcaca gcattggctc cctccccacc cagccccatc ggatgaggca    13440
ctctgttctg agaggcctgg gctgattagg accaagagct ggcaggttct ggcctgctgg    13500
actcagcttg cagatggccc tgatctttgt agagatgcaa ggccacccca tatcctggaa    13560
ttaaagtcac ttctatgtac tttgaggta                                     13589
```

<210> SEQ ID NO 5
<211> LENGTH: 203
<212> TYPE: PRT
<213> ORGANISM: Homo sapiens

<400> SEQUENCE: 5

```
Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200
```

<210> SEQ ID NO 6
<211> LENGTH: 11504
<212> TYPE: DNA
<213> ORGANISM: Homo sapiens

<400> SEQUENCE: 6

```
agacccngcc cctttcctgg gcggggccaa ggctggggca gggagtcag cagaggcctc       60
gctcgggcgc ccagtggtcc tgccgcctgg tctcacctcg ctatggttcg tctgcctctg      120
cagtgcgtcc tctggggctg cttgctgacc gctgtgagtt gttttgccc cgaccagacg      180
ggagttggga gtgggaatg agaaggaaag gaaggaaga cttcggggaa gaggccttcc       240
tggctgattt ttgtggggc aggagggtgg gtgggagctg ggcaaggtgc ccccgctcct      300
ggctgaatgg ggtgggctgc ctctctcttc tcccgggctg gggtcccggg agcggcctac     360
agggccgct cagggaaggc actggctgcc caagcgtgcc tagacggcct ggacgggttt      420
agggagcctc agaggctggc cacacagaga ctggtagggg gttcagaggg cgggaagtga    480
ggcggaccaa gggaagggc gggtctggcc cgtttcctgt ccccttctta ttgtggacag     540
atgccagcct ctgtaagtag ttatcatctc cttgccagct ggggctgcct tcttccaggg    600
catcttgtgg gaacaagaga tgggtgcaga ggcccaggta cttttgtgag aaggcaagga    660
gcttttaaca tcgccttcca ccccgaaccg tatcttgggt gttccaacct aggaggaatc    720
cccagggctt tgccttttc tcctgaattt aagatgacat aggagacccc tggggagatg     780
aacagtttat gggacacaat aaagggttag agaccagag ttctggttgg ctctgacagg    840
gctggtgatc agagggctgg agaaaccagg ggtttctcca ggcaccagag gggctcagag    900
ccaaccaagc atatctccgg gattttcaga agcctacact tgactcactt tttgtttaaa    960
tgtattttttg tagttcctca ttctggaggc tgggaatccc ccaagtacct ggctccttca   1020
tcccagcccc tctggcctcc ccctacttta gagggctgta gattcctgcc tgaagcctgg    1080
gcaggaatga cccatggtat caaggaaagc aagggaagca gcaagggaag agagggagtg   1140
gggaggctgc tttggtccca cagctttcac ttcacctga agcaatggct cttaggaac    1200
agggaggcag gggagggcg gagctggaaa gaggtaaagg ggggcccttg tggtaggagt   1260
ggagaaagag ccagaggagg tgggtgaag ggtgtgatcc aggcttctca agagcagagt    1320
ttgccctcat aactcccaac tttggctcca ggtagaggct gggctgtgac aacaatgtca    1380
gaagctatct attgagggct tcttgtgtgt caggctctga gccaaacact gcctgttttc     1440
tttgtctgat ttctcacaac tcccccatta tacagatggg caaattgagg ctcagaaagg   1500
gggattgtct tgccaaaggt ctcatagcta gctaatggaa gaacctggtt gtgaatctac    1560
atctgcatga ttcccgagcc tgcctctcag atagtgagag tctccaagct ctggtcctga    1620
gctgttttgt ggcagaagga ccagaactat ggggagtgag aactggagat tgacagactt    1680
ttaggggagc gttttattc tcatgtgttt gaagatggta tcaaggactt tcctatcttt    1740
gggagtgtgg gagctccacg ttcacaggat ggtgtcttgc aatgagctgg tgggggcag    1800
tagcctttc tacttccttt cccatttggg gtaagacaca tttctgtaag taatttgctg     1860
agatacccag gttgaatgag agccaccagt taggtaggat tctggacagc cagccaggta    1920
gccgggctgc ttgccatata tcatgcaagc agaaacaaat gaatgatgat taaaattgcc     1980
atttaatgag cacctactat gttcctgaca ctgtgctagg ccatatacat gtattctttc    2040
ttatcttcgt aatccaacct gcagggcagg cattattact cccatttag agatagaaa     2100
actgaggcta agagaagcaa ataactagt aagtgttaca aagtcaggac tggagtctaa    2160
agctgtctga ctctcaaact tgtgttcttt tcactggctg ttcccaaact gtgggacagt    2220
tttaaggagc acatggacat agaattaaac atacacttac tttacagttc ttttaaaaat    2280
```

-continued

```
ccttctcatt ttttcaaaga ggaagtctct ggagctagaa tagagttaat gcctctcaaa    2340
ggcttgctaa tccttctttt aaaacaaaaa tcaagagcag gcctgggagg ccttcaaca    2400 agcaaacaac cagctgggtt ttaataacct tgttttgttt ccccagaatt tattttagg    2460 gttaccttt atttatgaga agtgatactg gttcttgtct cttggcaatg atgtgaggtt    2520
tacatttaaa gtaaatgtac cggccaggca cggtggcttg tgcctgtaat cccagcactt    2580
tgggaggcca aggcagtcag atcacttgag gtcaggagtt ttagatcagc ctggccaaca    2640
tggtgaaacc ctgtctctac taaaaataca taaattagcc gggcatagtg gtacacacct    2700
gtaatcccag ctactcagga ggctgaggct ggagaattgc ttgaacccag agatagagg    2760 ttgcagtggg ctgagatgat gccactgcac tccagcctgg gcgatggagc gagactctgt    2820
ctcaaaaaat aaaataaaag tattgaaatt aacaataagt aattaatagc atgggtggta    2880
cctggatgta gtaaatggt gaagatgaaa cacaagttga tggagagagg agcattgaga    2940
cctgagttct catttggact ctgtcactgt gagactctgg gcaagtgacc ctcctctttg    3000
gtgctcagtc tcaactatct gtaaaatgaa agtgtgagtt tacccttcca gctttacatt    3060
ctagcatttt atgagggaag ggctggatga acagatgatg aggagttgga ggaagaaaac    3120
atgatgggct ttgaaaagga gcaggaaggg aagcagaaga ataggaggaa gaggccaagt    3180
gctaaacata gccccaaaca gcactgggac cagctgaagt cagccagctt caggactcca    3240
ggggagctgc tggagtcccc atatcctatg ggatctttgg gaagaggaat gactcaggca    3300
tcaagcccca aggaattctg ttctgttcag agaatattgt gagtttacag taccattgct    3360
ttgtaaaaat accagaatga ttctctgggt gcgattataa tcagctcagt tgacaattta    3420
cttgaaaaca aacatgccaa atatcatgca ggttccactt tctgttttga cttgcacttc    3480
agtttgcagc ctctgtcctg gatgactttt acctttctgc tgaagaagtt gcaacggaga    3540
tttcaagatc ccttcaaatt gcacaattct gttttttaggt ccatccagaa ccacccactg    3600
catgcagaga aaaacagtac ctaataaaca gtcagtgctg ttctttgtgc cagccaggtg    3660
agatgccaac cctctagccc catcatggag tccccctttg ctttggtggc agacgcagac    3720
cccatatgtt aactgtaaac tcaaatctga aacgacccat ttcccagccc tgcttcactg    3780
tcagaatgtt ctggttccct ctctaccagg taaaactctg tctaccctga actagggatc    3840
ccagcttctc catcttcctc gcctgattat aaggatccaa agactttcat ctttgaatcc    3900
cctaccctaa agcctggcct gatcattgtg tggttagtgt ctgactcatg gagttggcca    3960
gagccctccc tcatttcctg atgttttcca ggacagaaac tggtgagtga ctgcacagag    4020
ttcactgaaa cggaatgcct tccttgcggt gaaagcgaat tcctagacac ctggaacaga    4080
gagacacact gccaccagca caaatactgc gaccccagtg cgtgcgctgt tgggaaaggg    4140
acgcttggga accgggctga tattcccgac aatgcagcca ttctaatttt atgtagccag    4200
ggtctgctct gattggttgg agtccgggct gtactgatca ttaaatgatt tgattgccat    4260
ctctacttgg aagagggtct gaggaagaaa gagcaggcaa tgtggggagt gaggctcaga    4320
gcatggccca gcaggggggtt cccatccttc ctgcccttct cttctcagac ctagggcttc    4380
gggtccagca aagggcacc tcagaaacag acaccatctg cacctgtgaa gaaggctggc    4440
actgtacgag tgaggcctgt gagagctgtg tcctgcaccg ctcatgctcg cccggctttg    4500
gggtcaagca gattggtaag tggctcatct gggaatcagt tttggagggg acagaggag    4560 cttagggccc aaggtgaggg gctgggcagt gggcacttag ccccagaggc agaggaagca    4620
gaggctccaa cctatgtcgg tatccccact ggagtgagct gcagacggga ccttgttcat    4680
```

```
tctgccttct gccatgggga tctgcctttg aagggcaatg ggagaagtcc tcctggggac    4740
tgcagctgtc gggggcagta ccacatcggg ggaagagtgc tcaaggcagg agctcttccc    4800
gtcctgcctg gccactggct gccttgtgag ccggacaggt ggtccactgt gatggttaat    4860 gtcccctcc ccaccactc ccagctacag gggtttctga taccatctgc gagccctgcc    4920
cagtcggctt cttctccaat gtgtcatctg ctttcgaaaa atgtcaccct tggacaaggt    4980
ataagcactc atcccttgtg tttcctgctc taagagtggc atggagctgc ctccattctc    5040
tccagccacc tgtcctgtcc ctgctcccag aggtccacac acactcatgt acttgtgaag    5100
catctgcaga gtggcctcat ggccaaccag acaggcacat ttccacattt tttttgcctg    5160
ctgtctcttt gaggtaatag acactgttga tctctcgctt catgagagcc tcctatcttg    5220
ggggtattgg dacacttatt ttagctttcc ttctgcccct cctgcttctc tcagttttc    5280 ctcgtcttgc tttcacctta cctggctttc tagggctttc tgggctctgg gtgctcaccc    5340
tgagggcctc cctctcttac ctccaactcc aaacccacac caggtcctgc cactggctgt    5400
ctacgtgttt tgggaactta ctgtctccac tgttgtcact ttagtttggg cctcatcact    5460
gtggtctggg tgatgccttt tctgcctcct ggcctcccrg cctctgtctc tcccctcctg    5520
ctggttctgt ctccatcctc ttgccaacat gagcgttcga cagtttcttt caaatcatga    5580
cactctccta tttgagatgc ttcctgtctc tctgttggaa ctaagactcc ttagcatggc    5640
acccaacctt cctgttgcat ttcctgctct cttttcctgca tcgcatagct tcatgctact    5700
tgcaatcctc tgaacacact gttcattctc ttccatcaaa ctcatctgcc tggaatacct    5760
taaacatggg ccccaggcca ggcgcggtgg ctcttgcctg taatctcagc actttggatg    5820
ccaaggcggg tggatcactt gaggtcagga gttcaagacc agccagcaca acatggtaaa    5880
aacccatctc tactaaaaat accaaaaaat tagctgggtg tggtggtggg cgcctgtaat    5940
cccagctcct cgggaggctg aggcaggaga atcacttgaa cccggaaggt ggagtttgca    6000
gtgagccaag atagcgccac tgcactccag cctgggcaac agagcgacat tctgtctcaa    6060
aaaacaaaca cctgccccat taacttttg catttgattt ttaaaatggg gcaagatagg    6120
cacatgggac agaaggcaca aaagagccaa agtgatgtct ttctcccatc cctgccctt    6180 aggctcccag ttctttctgg agggagccat tgttccttgc atatccttcc agagattcta    6240
catataaaca aaccaacaca cacacacaca cacacaaaca cacacaaaat ttccctcctt    6300
ttacttttgc acaaatagga gtatacattt tatttgttaa ctgtctgcct ttccctaata    6360
gattgaaaat tccttaaatg tagaaacttg gccttttttt tttcttccat tgatacatcc    6420
cctatacctg gaacagtacc tgacgcatgg taggtgctta aattttact gataaatgtt    6480 gactgataac tggaggcacc actggtatag tttttttttt tttttttttt ttttttttt    6540 tttgagacag agtctcactc tgtcgcccag gctggagtgc agtggcgcaa tctcggctca    6600
ctgcaagctc tgcctcccag gttcacgcca ttctcctgcc tcagcctcct gagtagctgg    6660
gactataggc gcccgccacc acacccggct aatttttttg tatttttagt agagacggcg    6720
tttcaccgtg ttagccagga tggtcttgat ctcctgacct cgtgatccgt ctgccttggc    6780
ctcccaaagt gctgggatta caggcgtgag ccaccgtgcc cggccaccag tggtatagta    6840
ttaatggaat cagtgcattg gcttacgtat ctgattacag ctcagtaagt gtgtgaccct    6900
cactgagcct cagtctcctc atctgaaaaa tgggaatgac cttcatttca caaggcttga    6960
gctaaaaaca tgtaaagtgt attgtaaatt cctgaatgct ctactcatgt aagactaaag    7020
```

```
taggccgggc gtggtggctc acacctgtaa ttgcagcact ttgggaggcc gaggagggca   7080
gatcatgagg tcaagagatc gagaccatcc tggctaatat ggtaaaaccc tgtctctact   7140
aaaaatacaa aaattagctg ggcgtggtgg cgcacatctg tagtcccagc tactcaggag   7200
gcggaggcag gagaattgct tgaacctggg aggtggaggt tgcagtgagc tgagatcgcg   7260
ccactgcatt ccagccagtc tggcgaaaga gcaagactct gtctcaaaaa aaaaaaaaaa   7320
aaaaaaaaaa gactaaagta catggtttct tcaaagcttc tctctctttc tcccacctta   7380
gatgattttt cctttgcaat gtcctgtgtc cattccgccc cactcctcct ggggccacct   7440
ggaccaggtc ttcatcatct catatctata tgtttgctgt gtctcctggc tggccactct   7500
tctgtaattt ctcctcctct gagctctctg ggcagctgaa tcttctcact agtgaagtcg   7560
cctggttgga tgctgatgag actgaccagc tgaatccagt tgaaaacttc acacttggca   7620
gtgatctggt tctaaagaca caattttcca tagtttccta acaccatcct gcatgccacc   7680
tgccttattt ccccacatca catcgtccca cttagcggga ctgcactgct gatccaaatt   7740
ttacatcctt tagggcccac tcaggtcata tgtcctcagg gaagtctttc tggaagaacc   7800
ttaaaccaga ggttctcaac agggggcagt tttgctccct gtggaacgtt tgccaatgtc   7860
tggacacatt tcattcgtca caaacggaga gggggatgct acagggatct ggcggataga   7920
ggccagggat gctgctgaac atctgcaatg cataggacag cccaccccca cccccacacc   7980
cccagtaaat aatgatccag cccaagtgtc actggtgctg acgttgagta accctatctt   8040
aagctgaact catcatctct ccattccagc cttggtggat tctgtctcct ctgaaccatt   8100
cccatctcac tttagcctac ctagatcaca aagcttggca ctcattatag actccctat   8160 ttattactcc ttcaagatgt gcaagaatct tttctctgca cttttaagtt ctgtaagaag   8220
agtctgtgtc gttcctataa taaccagcat aggacgttgc acgtgttgtg tgctcagtga   8280
acctggattt gttgattgtt gactgactca ctctagagtt ggaaatctta tgcttggga    8340 aacttaatat ctctttcttt ctctgtgtgt gtgcatttgt gcacgtgtct gtgcatagct   8400
gtgagaccaa agacctggtt gtgcaacagg caggcacaaa caagactgat gttgtctgtg   8460
gtgagtcctg gacaatgggc cctggagaaa gcctaggaag gtgggaactg aaggggaga    8520 tgaggcacac aggaacactg gatgggaaaa aggggagggg aggcagtttg ggggtgtggt   8580
atcacagctc tgccacttat cttgggagtc tgggcaaatc acttccctc tcttagcctc    8640 agtttcttca tctgtaaaat gggatgataa cagcacttcc ttagtaggtt ttgattttag   8700
agtgagaagg ttggcctaca gtaaagatca gataatgtaa atcagtgaaa aaggtcaggg   8760
gtaagaaaat tacattctct ttacctaacg ctaaatgacc agttaatggg tgcagcacac   8820
caacatggta catgtataca tatgtaacaa acctgcacat tatgcacatg taccctaaag   8880
cttaaagtat aataataata aaatttaaaa aaacgaaaaa tacattctct ttgcttttc    8940 tcaaaatgta ctttcctctt tgtagggctg ggactagaat gaggtgagca aggcacttgc   9000
cctcgggcgc aatatttaag aaggtgccat aaaagtgtag taatcaaggt aaattcattt   9060
tgatgcaata ttttttaaaaa taaaaattaa tgcaaagaaa tccatgatga gcaagatagc   9120
aacattttaa ataagaaca ggatccgacc ctgtgtttgc atgaccctgc ctcactcacc    9180
tcaccctaat cctggccctg gttccagtaa aaggaatagg cagccagcct gcaggccgta   9240
gtttgctgac ttggtgtccg cctgatgatt ttcaaaatat ggcattaaaa gaatgtttac   9300
cttgatgact gagtgttttg gacatccttt tcaatttgt cctgaaacaa tttcatccct    9360
tgcctcacgc tagtctccgc cctgcctttt ggtctttctt ttattttccc actttgaaaa   9420
```

```
aaaaattcgg catgagaaat actttacctt tcccctccac tcttctatac caaaagcaac    9480
atgcagacat gaatcatgct agacctcggc attgggcaga gagcagggag tggcggggag    9540
catggtgagc aggtggtgac agccactgcc accactcgct tctagatggt tcccaggtgg    9600
ggaggctgcc aactggaacc cagtcttccc agtttgtaag agaaatcaga tgtctaggtt    9660
tgaatatgtg atctcccagt ttaaaaatgt cggcaaatat ttccaaacgt taagaaaatg    9720
ttctggctcc tttaaagaca tctgccagcc acatttcccc aaggaccgcg gtttgaacct    9780
tctgatgtag atgagctctg acattggaag attctggagt ctgacaagtc acagcaggtt    9840
gagggtaggg agaaactgca ggtgaggggt gcatgctgaa gtcctgattt ctccaggtcc    9900
ccaggatcgg ctgagagccc tggtggtgat cccatcatc ttcgggatcc tgtttgccat    9960
cctcttggtg ctggtcttta tcagtgagtc ctcaggtggg gaggtgttgg gggagggagg   10020
ggagaccacc tgtttcttat ctggcctctc caactcccca tccttttttt tttttttttt   10080
tttttagaa aaggtggcca agaagccaac caataaggta ggtcacccct gagaacccgg    10140
gacagagttt tgacaaactg gaagatggc ctcacggttg cctatggggc agtaaaactg    10200
attcagagtc tgtctctgca gccagtgggg tggcagcaga attggggact gtcatcccca   10260
cccaccatgc tccttccatc cagagctcaa tcccccacag aactgcccct ggcaccactg   10320
gcagagccta acactggctg ttcttcactc ctttcctggc attcaacgcg tggggagctg   10380
catctttggg ccttggggct gggtcaaatg ggtgggagca aatgtggcag ccccttaagc   10440
ccactggctc ccactctgga agctcttcgt cgcccttggt gtggccagca ggggcagga    10500
ggcacccgag gaatcagcac tgacccgccg tctgggaaag gggggagggc ttggggaagg   10560
gatccgcttc ccagggaggg gctcctcaga ggcacagctg cccctgctgc tggggtgac    10620
ctcacacctt gcctctccag gccccccacc ccaagcagga accccaggag atcaattttc   10680
ccgacgatct tcctggctcc aacactgctg ctccagtgca ggagacttta catggatgcc   10740
aaccggtcac ccaggaggat ggcaaagaga gtcgcatctc agtgcaggag agacagtgag   10800
gctgcaccca cccaggagtg tggccacgtg ggcaaacagg cagttggcca gagagcctgg   10860
tgctgctgct gctgtggcgt gagggtgagg ggctggcact gactgggcat agctccccgc   10920
ttctgcctgc accctgcag tttgagacag gagacctggc actggatgca gaaacagttc    10980
accttgaaga acctctcact tcaccctgga gcccatccag tctcccaact tgtattaaag   11040
acagaggcag aagtttggtg gtggtggtgt tggggtatgg tttagtaata tccaccagac   11100
cttccgatcc agcagtttgg tgcccagaga ggcatcatgg tggcttccct gcgcccagga   11160
agccatatac acagatgccc attgcagcat tgtttgtgat agtgaacaac tggaagctgc   11220
ttaactgtcc atcagcagga gactggctaa ataaaattag aatatattta tacaacagaa   11280
tctcaaaaac actgttgagt aaggaaaaaa aggcatgctg ctgaatgatg ggtatggaac   11340
ttttttaaaaa agtacatgct tttatgtatg tatattgcct atggatatat gtataaatac   11400
aatatgcatc atatattgat ataacaaggg ttctggaagg gtacacagaa aacccacagc   11460
tcgaagagtg gtgacgtctg gggtggggaa gaagggtctg gggg                    11504
```

<210> SEQ ID NO 7
<211> LENGTH: 289
<212> TYPE: PRT
<213> ORGANISM: Mus musculus

<400> SEQUENCE: 7

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
    210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
        275                 280                 285

Val

<210> SEQ ID NO 8
<211> LENGTH: 16047
<212> TYPE: DNA
<213> ORGANISM: Mus musculus

<400> SEQUENCE: 8

```
ccccgccctc ttcctgggcg ggactcctag cagggacttt ggagtgactt gtggcttcag      60
caggagccct gtgatttggc tcttctgatc tcgccctgcg atggtgtctt tgcctcggct     120
gtgcgcgcta tggggctgct tgttgacagc ggtgagtggc ttgtgttcta acctccaagg     180
gagttagggc ttagagagtg agagatggaa agaggaaaga ggagacaaga ctttggagat     240
gagagatctt cctactggaa gcggcggtta gtaggatggg caagatctct cgcgtcttga     300
cacacacaca cacacacaca aatgaggtgg gctgctcctc tttccttcca gaaggtcggg     360
gttctgttcc acgaagccca caggggaacc ttagggaggg cattcctcca cagcggtgcc     420
tggacagctt tgtctgaccc aagccttggc tccggagctg actgcagaga ctggaagggg     480
```

```
ttagcagaca ggaaagcctg gctaggggga agggcgggtc tggcctgttt cctgtcactt     540
tcccattgtg gacagatgtc tgccacctgt ggttatcttc tccttgccag ttggggccac     600
tttgtctagg gaatcttgtg cgaacaagac cccaggtact ttttagggaa gaggtaattt     660
actaaccacc atacccgtat catagctgag ccaatctaga gaaatcccca agtttgtgcc     720
tctgcctcat gagcttaagg tggtacagga gacacccaga ggatgaggag gaagaagagg     780
aggaggggga ggaagaggag gagggatagc tttagaaccc aagaaggat aagagaccag      840 actaggtttc tccaggcacc agcagggctc agacccaatc aagcgcatct tggggatttc     900
tagaagccgg cacttgattc gcttttggtt taaatgtatt tctgcagttc ctcattctgg     960
aacctgggaa tcccctgact acctgagtct cagcccctct cctctggcga ggctccccta    1020
gctttcaggc agggtagatt cttccggtt ggtgacaggg acttcggtaa cttcatgggt     1080
tctgaattgt ccacccagga aggtgtcgtg gttcaggact ggctttctgc agctgggaca    1140
gtcagtgccc taagcacatc cctgtccatc agccaatgtc acctgccat cagccaatgt     1200 cacctatccc aggttggtct agttgagaat gacctttcac attcttcttt ttcttctgtt    1260
cacgcatggt ttgtgtatat gcgtacatct gtgtgggaac acacgtgtgc ttgcatgcgg    1320
tagcctgaag ttcatctcat gagtcatcct tggacacggt cccttcttag tcatccacac    1380
agggtctcaa gcaaacccag agctccccat agggcgagtc tcacacgtca gctggctctg    1440
gggaccctct gcttctgccc tctgaagctg gagttacagg gaggccacta caaagacctg    1500
gtgtttgcac gtgtttctgg agatcagaat tctggcccac ccatttatat ggcaaacacc    1560
ttgagagctc agtcatctct cttgtccttg aatctctgat cctcctgcct tcacctccct    1620
agtgcataca ccaccatgcc cagttttatg tggcacttag aatagaatct agggcttcat    1680
gcatgctagg caagacacta tacttactga gacacacccc cagccaaagg acatagactc    1740
tgacatgtgg cctgccaaga atcaccatgg aggttagccg caggaaagga gcagaagcga    1800
gacagttgct ttactagttt tcattttta ccccaggcca gtggttcctt tcgcagaggt     1860
ggtctaagac catcagaaaa cacagatatt tacattagga ttcagaacag taacaaaatt    1920
acaattatga ggtagcaaca aaaataatgt tttggttggg ggggggtca gcaccacatg     1980 aggaactgta atgggcccca gcgttaggac agttgagaac cactgctcta aataagactt    2040
ttagggagac tggatgcagg aagacggtga ggtgagagag aagtggatga gggcctttgg    2100
gagggatgga ggaagaaaca gaggtgtgat gaaggctagt ctggaccact caagaacaaa    2160
gtctgccctt gtaagcccca atctgggctc caggagggg ctgggccctg agagaaatag     2220
caggtgttct ttactgacct cttcctgtgc aggggctgt gagggagact gcatgtcacc      2280
ttcctgtgtg agggagactg catgtcacct tcatttgatg tctcccaacg tctctgttac    2340
acggatgacc aagatgaggc tcagaaaggg gaggggtttt acccaaagcc tcttgacatg    2400
gatatgaagc tatgtctgcc tgacttctga gcctgccact cacgcggcaa ggggtcttca    2460
agctgtggcc ctgagaccta ttgtggagga aggaacaatg ctctgggggc tggaaactgg    2520
ggctgactgg ccatcagagg gaaagtgtct tttccaaagg tgccattgag gatgtctact    2580
gttctagaag gaaggaagga aggaaggaag gaaggaagga aggaaggaag gaaggaaagg    2640
agggagggag ggagggaggt gggaagtctc agggaagata aaactcaggg atgatgccct    2700 gctggggca ggtgctttca ggtacatttc attaagtgat ttgctcagat acccagtttg     2760
agtgagagtt ctcaatttcc tggattctgg acagtcagac agctactagg gtgcaggaca    2820
```

```
ccagggcaga ccccccatcat ctatgtgtgc tgattaaagc tgccatttttc tgaatactac   2880 cttgctatac tgccaggcca tgggcaagtg ttacaatctc attttaaagg tgagaacaca   2940
gggctagaga gatggcttag tgggtaagag cgcacgctgg ctgccatagc cacattgggc   3000
tggtacataa attcaacaag aataataaaa acaaaggaaa cacagtctta gagaagcaaa   3060
ataattagga tggtgtactg gctagttttg tgtgtcaact tgacacaggc tggagttatc   3120
acaaagaaag gggcttcagt tggggaaatg cctccatgag atccagctgt aaggcatttt   3180
ctcaaatagt gatcaagtgg ggaggtcccc ttgtgggtgg tgccatctct gggctggtag   3240
tcttggttct ataagagagc aggctgagca agccagggga ggcaagccag taaagaacat   3300
ccctccatgg cctctgcatc agctcctgat tcctgacctg cttgaattcc agtcctggct   3360
tccttagtga tgaacagcag catgaaagtg taagctgaat aaactctttc ctccccaagt   3420
gcttcttgat cgtgatgttt gtgcaggaat agaagccctg actacacaga tgggatacag   3480
agtggtttgt cccgttctca aatgtgggct ccacgcaatc ggtagctgtg gttgtttcta   3540
aaatgtaacc tggcttcaag gagcacacga gcaagccgga gggcttagct ctgcagttaa   3600
gagcatgtgc tgcccttgca gagagctgga atccgattcc cagctcccac attccacagc   3660
ccccagatat ctgatcccct cttccgaggg tacttacacc cacacatgtt catattcata   3720
tatctaccta taatcaaaca tgaaataaat cttgtggcta gagagatgct cagaatattg   3780
ttgctctggg agaggaccca ggttcagttt tctagcaccc acgtgtggcc cacaatcatc   3840
ctcaacacca gttccaggga acccagtgcc ctcttctgac ctccaagggc accaggcacg   3900
catgtggagc atattcaggc tacacttgta cacataaaat aaataaatct aattattttt   3960
aaagtcttaa aaaacaaaca aacaaacccc caaacaccgt cgcctaaaac ctcaaggata   4020
gggttgtgac tgaaggcact tgtcatataa gcctgaggcc ctgggttcat ttcctggaac   4080
ccatgtaagg tagtgtgtgg tggcagaagt ccaagtctga catcctaagg ctcctactgt   4140
gagacaggag gtgggaacag gagaaccccg gaaactttca gcacatgcaa ccaagaacaa   4200
caaaatgatg gtggcttaag cacagtagga gatagcactg agagcagtgt tggccactga   4260
cctccgtaca cttccagtta tggcaagagc acgctccaag ctgcagacag ggcagtgggc   4320
gttgcgtgtg cacacacacc aaaacacggg cccactttat ggttcttaaa aaaagtttct   4380
acacttaaaa aaatgtagtt ttcgttatac ttatttattt atatattatt tgtatgcatg   4440
catgcatgca tgcgtgcttg agtaccaaag cgtgtgtgtg gtcagaggac aagttaggga   4500
agctggctct tcctaccatg tgattctaag gaactgaact caggctgtca ggcttggcag   4560
caagagcctt caccagctga gccatctctc cggcacctct ctctctctct ctctctctct   4620
ctctctctct ctctctctct ctctctctcc tgtttgtatt tttctttttt aaaaatattt   4680
tttcaagttt tttttttttt taaagatgta tttattttat gtgagtacac tgtcactgtc   4740
ttcagacaca ccagaagagg gcatcagatt ccattacaga tggttgtgag ctaccctgtg   4800
cttgctggga tttgaactca ggacctttgg tcagtgttct taactgctga cccatctctc   4860
cagccctgtt tgtattttttc aacacaaggt ttctctgtgt agccctggcc gttctagacc   4920
aggttggcct cgaactcaga gatccacctg cctctgccgc tgagcgctg ggattaaagg   4980 tgtgcgccac cactgctcag ctgactgttt ctggaagtgt tacagctccg ctctgaggga   5040
aacttttctc tgagtgttgt agatgtgagg agaaatcccg aaaggcttcc ctgtggaggt   5100
gttgcatctc tgaaaggaaa agcggagtat cacaaagtcc cactgctgga caaacctcag   5160
agagtggctg cctccgccca ggggcgaagc agcagagagc tgagctgcag gcagcttagg   5220
```

```
cagttctcca gggtggagtc cttctgggca gggattggtg agacttcatg ctcaaggatt   5280
ggtgggttcg catagttctt ttattttttc ccaactagga agtgggctca ggcctttccc   5340
ccagctagag tttcactgtt ctttaaaaaa catcattttg tttttatttc atgtgaattg   5400
gtgttttgcc ctgcatgttt ctctgtgtga gggtgtcaga ttccctggat ctggagttac   5460
aactggtggt tgtgagttgc catgtggatg ctgggaactg aacttgggtc tctgaaaga    5520 gtaaccagtg ctcttagcca ttgagccatc tctccagctc ctccaaatcc tttcttatt    5580 catttaaaaa attacatgta tgtatgtatg tatgtatgta tgtatgcatg tttgtacgca   5640
cacacacaca cacacacaca cacacggaga ttagatgcta acttttgaga gttggttctc   5700
tccttccatt tctgggcctt gaaattctgg ttatcagtct tggcagcaag cgccttgatt   5760
ggctgagcca tctcgctcct tggttcttca aggagtaagt ctctggcgct agctagatca   5820
tagttaatgc ctttttttt tcttttttct ttttttgaga cagggtttct ctgtgtagct    5880
ttggctgtct tggaactcac tctgtagacc aggctggact cacagagatc tgcctgcctc   5940
tgcctctgga gtgctgggat tagaggctta tgccaccaca gttggccagt taacacctct   6000
gaaagacttg ctaccaaccc accccaggct taaaagtaaa atcaagagca gacagagcga   6060
aggatctcag caaagaaagc tacgcatcga ggcttaataa ccctgttatg aatctgttga   6120 gtgtatttt agggtttctt ttaatttata ggaagtgata cttgctgacc tcttgatgca    6180
gcagtagaag atttacagtt aaaagaagtg tgcttaaatt agcaagaagc agctcatagc   6240
atgggtggtc cccggatgtt gtagaaacac atgttgagag tcccgcccct gtggactctg   6300
ttcagtgttg ccctctgtgg ggtgattctt atctctttgg tggcagggag ctgggacag    6360 aaaccgggag aagggctgag gccagcttga gccagcagtc tcgggactct ggaggaagaa   6420
ctggagttct ccctacctgc tgcgtctttg ggagcactga agagtcctgt gcatctgttc   6480
ggattagagg gttctgcgtt cttgctttgg tagatggcag taagacgatg tgacaacaga   6540
gtaaaaaaaa aaatagacct cacactctgg gggctcactt ttctgctttg gatttccaca   6600
tcagctacag cctgcgtctt ggctaacttt caacatgccg gtggaagatc ccttccagct   6660
gtccacttct gttttaggt ccatctaggg cagtgtgtta cgtgcagtga caaacagtac    6720
ctccacgatg gccagtgctg tgatttgtgc cagccaggtg agatgctagc cctcctgccc   6780
cgtaccaaga ccctttccct cttggattgc tggtggatgc agaccccata tatagactgt   6840
gaactcaagt ctaaaatgac ccatttctcc ctcttccttg atgccagaat accccaagct   6900
gtcccgtctc ttccatcttc cttactcgtg tagggtctga gatatccatt cccaaactcc   6960
aaccctctca cctccagtcc tggctccctg ggttgtgaca cagtctgtgt cacaggattg   7020
gcccaacctg cctcatatcc tcctgttttt caggaagccg actgacaagc cactgcacag   7080
ctcttgagaa gacccaatgc cacccatgtg actcaggcga attctcagcc cagtggaaca   7140
gggagattcg ctgtcaccag cacagacact gtgaacccag tgcgtggggc tgcctgggaa   7200
ggggtacttg agaaccgggt tgatgttcct aatgctgaaa tccctctgtt gtcagtggcc   7260
agggtctttc ctgtgagcta gagtctgggt tgaaggggct agttgactga catctgtact   7320
gggaagagcg agaaaaccag cagatgacgt gaggagtggg gtcctggctg cggcccagcg   7380
ggttttccca ttcttccttc tcatctccgc tcagatcaag ggcttcgggt taagaaggag   7440
ggcaccgcag aatcagacac tgtctgtacc tgtaaggaag acaacactg caccagcaag     7500 gattgcgagg catgtgctca gcacacgccc tgtatccctg gctttggagt tatggagatg   7560
```

```
ggtgagtggc ctgcctgggg aaacagctct gtgggtggga gagctggggt gagctttggg    7620
tctctggcct ccagaagctg agggcagaga aagtcccacc tgggctggga tctttcattt    7680
ggatttggac ctgggctctg ggcagcttcc tgcggggttg tggccttcag gggctgtgtt    7740
gccttggggt aagaagctga gggcaggtgt tctgtcctgc cctgcttgtc tgctggctcc    7800
cttgggagtc agacactgtg gcccaggtgt ctgctcatgc atctttccgc atccttccag    7860
ccactgagac cactgatacc gtctgtcatc cctgcccagt cggcttcttc tccaatcagt    7920
catcactttt cgaaaagtgt tatccctgga caaggtataa gggtcacctc tccctaacca    7980
atgacagggt gggtcttgtc tcagtctctt tagccacctg ctgttcagtc cctgactttc    8040
cccaccccca tggtgggtca cttactggtg aatgtgacct tgtggctggc ttaagggaca    8100
ctttgtgcag ttcttttagc ttgcttctgc ttagttaata gaagcctgtt ggtctccata    8160
tcctcttgaa gtctcttctt aaagcatcat gacactcgta ctccccttttt cagttcactt    8220
tcttggtggg tatgtgtatg tgtgcatgtg tatgcatgtg catgcatgca tgtgtgtgtg    8280
catgcatgta tgagcatata tatgcatgtg catgcatgga tgcatgtgca cacatgcatg    8340
tatgtgcatg tatgtgcatg tgcattcatg catgtgtgca tgcatgtgta tgcatgcatg    8400
tgcattcatg catgtgcatt catgcatgtg tgtgcatgtg tcagctatca gtttggtgtg    8460
ttcctcctca ggtactgtcc actgttttt gttttgttt gtttgtttgt tttgttttgt    8520
tttgttttga gagtcccaac actgggacta taaccacttg ctaccaagca tggatttttt    8580
tttttttttt atcgtgggtt ccagggcttg aactcgggcc cttgggttca cagtgctttc    8640
ctgagtgagt tatcaatgcc cccagccctt ctggactctt acttgtgttt gttgggcttt    8700
gtctgggttc tctgaccact tctttccacc tctccttggc tgtcttatct acatctatgg    8760
ctccatctcc ccctggatct gtccttcagc ccccagatgg tcaagtccca ctgctgagtg    8820
ttatggatca ccagcacctc agactctgtg catccaaaat gggcccctag ccaatccctg    8880
agccccagct gacaggcagg ttctggctcc aggcagtcac acagtgagct gcccacccctt   8940
gccttcaact ccctgtcagt caggcccata tgactgtctt gggaatccac ctcctcactc    9000
tctagagtgg tcacgtgagt tcgcacctcc tcactgtggt gtggtgatgg ctctgtctcc    9060
tcataggctc cctgcctctg gtgtctccct tggcagcttt gcaccatgct gctgttggga    9120
gcttccgtag ccccttttgg atcatgtcgc ttcatgattt aaagcactcc acgtctccct    9180
gctgcctttg ggaggaagcc cagactcccg ggactggggc tgggccttcc agctacagtt    9240
cctgtctctc cccccacacc tcgcaccctg cacttgcacc ccgggcacac tgtttattct    9300
tttgcttcaa agtctcctgt ttgggagaaa acaatatata tgccctattc tgttttttat    9360
agttcacatt taatgttttt taaatgggca aacctgtcac ctcaggctgt ttcctcacta    9420
ctccttcaga gagagagaga cagagagaga cagagacaga gagagacaga gacagagaga    9480
gacagagaga gacagagaca gagactcaga gacagtcaga gagacaaaga tagagacaga    9540
gaaagagaca atcagtgaga gacagaggga tagagagaga cagagagtca gagagacaga    9600
gacagataga gagacagaaa gacagagaca gagaggtggg gggaggagat agggggagac    9660
agagggacag agagacagaa ggacagagaa actgctaata aacaaacaca ttgacatacc    9720
actcccctct gccatgatac acatatgcac acacacacat acacacacac acacacacac    9780
acacacacac acacacacac acacacacac acacacacca cagtggtttc tcttgtggtt    9840
atagtgcttg cttgcaggtc acactcaccg tcctcactgg tgggtttagt tgttcataga    9900
agttcccgtc ccggagtcaa atgtgcaact gccgcactgc cccacttagc tggttcatgc    9960
```

```
tgctgtttca acttttatcc cctttggaga cccttcggat cttctctggg gacccccaaa   10020
tctgcctcag tttgtgtgag accctcaggg atgcccctaa tctcgggagg cttcagccaa   10080
cttgtaaagg tgctgagggc ctttctcaca caaggctaga gcacgcacgc attttctctg   10140
aagcctctct tccaccacat cccggttttc cttcgccatg tcccttgcca tgtcccctct   10200
gtcccctcct cccaggacct tccatccaca ccacacatct ccactcctgt cctgcctctg   10260
gctgcccact ctgctgcaac ggtcctctca ccagtcaggt cactccctag ctgcctgcct   10320
gcagctgccc tgcctgcagc tgctcatcac cgcacttgtc accatgtgac tcccctcctg   10380
tcacactgtt cctacttagc tgggtcccac tttcccatcc ttcaatgcct tctgatgccc   10440
cccttcatgg ggaagtcttc ccagaagacc ctgaaagcag agcttcttaa cggggaccag   10500
tttggctctc tgtgggggcg ttggccacat ctgatcatct tttggatgct gtacttggcg   10560
gggaggctgt ttctggcatt tggttagtgg aggcaaaggt gctgctaaat agtctgtgaa   10620
acaaaggcca tttcccagca caaaatacct gcagattggc catttccatt tcaatatgac   10680
cgtaaccttt cctttctgtg gtttctgttc ttcacttaat gatcatcttg ggatgctgca   10740
ctctaagtca cgtgctcagt gaacaaggac ttgctgcttg ctgggggact cccctgggct   10800
tggaagtctt atggcgggga gccctgtttc tgtctgtctg tctgcatgtg tgtgtgtaca   10860
tgcacataca tgtgtacaca tgtgtctttg tgcagctgtg aggataagaa cttggaggtc   10920
ctacagaaag gaacgagtca gactaatgtc atctgtggtg agtccagggg agaatggcct   10980
tgccaagtct ttgggaagca gggaactggg gagagactga ggcacgcagg aacactgact   11040
gggataggag tgagaccaag aggcagtttg gggtacagta ccttagctcc cgtcttggga   11100
gctgggtaag tcacatccct tgtctgagcc tcagtttctt caattgtgaa ataggcccac   11160
agcagctcct tcctccctta cctgggtcgt gtaagtggca ttggaatttt gcagtttgga   11220
agctgctgcc ccttgcttga ggttcaggtt cactgtgaca gtgtcacctg gtaaccccag   11280
tttggatgct aggatgtaaa acttgaccat cccctaatgg atcacaatct cagataacaa   11340
tagagaccag gccacttttg aatgagtgaa gacagagaag ggtaagagag ctaggtctga   11400
tgagcgggcc tgtcagcgca gctaattaga ggcaagagct ttgtaagttc aaggctagcc   11460
tgggcagctt agaaagatac tggttcaaca tagaaagggg ctgctgagat gggtcagtaa   11520
gttaagctct tgcctgatgg cccagcttcc atccccagca tccatggaaa ggtagaagga   11580
gaggatcagc tcctaaaagt tgtcctctga ccgctgcatg tacagcacaa cacagcacag   11640
cacatgtgag tgtgcataca tcatgcacac acatcataca tacatcatgt gcacatatca   11700
tgcacacaca tcatgtgcac acatcataca cacatcatgc acacatca tgtgcacaca   11760 tcatgcacac acatcataca tacatcatgt gcacatatta tgcacacaca tcatgtgcac   11820
acatcatgca tacacatcat acacacacat catgcacaca catcatgtgc acatatcata   11880
cacacatcac gtacacacat catgcacaca catcatacac acatatcatg tgcacccatc   11940
atgtgcacac atcatacaca catcatgtac atgcacaccc acaatagtga taaataaaag   12000
tttaaatatg tttctagggc tggggaggtg gcacttgctg ttctgacaga ggacctgggt   12060
tcagtttcct gagcccatgt cattgcagta taaaactgtc catgactcca gctcctggtg   12120
atctgatatc tctgctggcg ctaggcacat acatgatgca cgtacatacc tctagcactt   12180
tctgatatac ataaataaaa atagatacaa attaaaagac attaaaaaaa aaagtaagaa   12240
gatagctggg ggtggggctc agtggtggag cagttgtcca gcatgctgag gtcctgggtt   12300
```

```
agaccccac  acttgcctag  catatgtgag  gtcctgggtt  agaccccac  acttgcctag   12360 catatgtaag  gtcctggggtt agaccccac  acttgtccag  gatatatgag gtcctgggtt   12420 agaccccac  acttgcctag  tatatgtgag  gtcctgggtt  agaccccac  acttgtccag   12480 gatatgtgag  gtcctgggtt  agaccagtgc  cacaaagtaa  aaagaaaat  aaagtgcag   12540 tctctttgct  ttttctcaag  attgcctttt  tgtcttggaa  aggcgtgagt  ggatggagtg   12600
tgaaaagcac  ttgagttcat  gtgtaacatt  taagaagaca  tcgagaaggg  acagtaagca   12660
agagaaaaca  ttttgagatg  atgctagaaa  aaccaaaaac  acttttaata  aatctgaaac   12720
caaaaaacat  gttgatgcac  aacatagcaa  aattttaaat  taagtaagag  ctgggctggc   12780
gagatggctc  agcgggtaag  agcactgact  gctcttccag  aggtcctgag  ttcaaatccc   12840
agcaaccaca  tggtggctca  caaccaccca  taatgagatc  tgatgccctc  ttctggtgtg   12900
tctgaagtca  gctacagtgt  acttacatat  aataataaat  aaatctttaa  aaagtaagag   12960
ctgaccttgc  cagactcgag  accctgccta  ccttcttcat  cctaaccttg  gccctggttc   13020
caatacaagt  ttatctaaaa  gccaggtagc  cacctatgga  cctgtgtttg  tttcactggt   13080
gtctgcctcc  cgacccatga  gctgggtgtg  gtggtacagg  catgagagcc  ccaagtttaa   13140
ggccagcctg  aaccacttag  tgagaccctg  tctcaaagaa  gacttacctt  catgacagtg   13200
tgtgtgtgtg  tgtgtgtgtg  tgtgtgtata  cacaccccctt gcctctaaga  gtacctgcct   13260
tttggtcttt  tcatttgtca  cttagaatag  cagtgcagac  acagagatac  tttgtttctc   13320
tccgccatac  ttccatagca  gatgtaacaa  tttgggggct  agtgtaggga  ggggtaaagc   13380
aggcaggcag  gctgtcccctt caagacacag  ctgacgaaca  caccagatgg  gaagttggct   13440
cactgggggc  ttctcattcc  aactgcaatc  tcccagagct  agagactgct  caaagggtag   13500
gagtatttac  tatgcaagca  tgagctaggt  gtggccacac  cacatgtgac  tgtgaccttc   13560
ataccatgtg  taggggggtg  gcactagaag  gagaattgta  gggtgttgcc  tcccagacta   13620
gctccaggct  caagagactc  tgtctcagca  gaaggtgcaa  tatggtggat  caggacacca   13680
gcaccctcct  ttggcctctg  catgtgtgca  cagatgcaca  catctaaaca  cataccaggc   13740
ccacatacac  cgtaccccac  caccacacaa  agatggactc  tctcaattta  taaacactgg   13800
caaataccat  aaagcgtttt  aaaagttccc  ctagtgacca  cattacccac  aatgctactg   13860
cttaaaagct  ctgacctgga  ttctgggagt  gtacagatgc  tttgggcaag  gagtgggagc   13920
acctgccagt  gagagcacct  gccagtggga  gcacactcca  ttgggagcac  ccgccagtgg   13980
gagcatctgc  cagtggggtc  cactcaagtc  tgtttctcca  ggtttaaagt  cccggatgcg   14040
agccctgctg  gtcattcctg  tcgtgatggg  catcctcatc  accattttcg  gggtgtttct   14100
ctatatcagt  gagtgctcag  gagaggaaag  ggagggaggg  ttcagccctg  tcgaaccagc   14160
ctcctgactc  accctcgcaa  tgtcccacac  cccttcttct  tctcactaga  aaggtggtc   14220 aagaaaccaa  aggataatga  ggtaagccat  ccctgaggga  gagatgctgg  aaagagtgac   14280
tggtgggcag  ggagggaggc  tcacggcgta  gggagacaga  ctcagtaagc  agagagcttg   14340
tattggatcc  ttgagtgtgg  acccatggaa  aaggcccatt  acacccacgc  tggtgggggc   14400
ggggagaggg  ggggaggatg  gacacaggga  tcttaggagc  ttgctagcca  accatgggct   14460
actccaggtt  ccaagagaaa  ccctgactcg  gaaaataagg  gttaagagtg  caagaagaca   14520
caagatgttg  acctctagcc  tctaataatg  tgtacatggg  tgtgtggacc  ctctacgcca   14580
tgagcataca  cccaatacca  cgccacactc  cgcgcgcgca  catgcgcgca  cacacatgcc   14640
caaacaggtt  tagggtccgt  tccctggaac  atataggtgg  gctactcgca  ccccaccca   14700
```

```
gccctgctct cagtctccat cgcttcctcc tactcaacta cttcccctta gggcagagct    14760
gggcaccact ggcagagaaa ctctggctgt gctttcctcc agccttgaat gctggggatg    14820
ggagtcggcg gcggggggtg ggggtggggg gtggggqtgg gtggatcccg ccttcagggg    14880
ccagtaggtg gaaccaaagg ggcagtttct cctgctggtc tgcagtggct ctggaaattt    14940
cctgccaaat ttcatgtgtc cagcagggqg cagaaggcat ccaagaaatc agttttggta    15000 caccccatc ctcccacccc attggaaagg acttgaagga gggattctat tcctcagagg     15060
cagggtggct ctgtggctag aggtgacatt ggaccttata ccttgactcc ccagatctta    15120 cccctgcgg ctcgacggca agatcccag gagatggaag attatcccgg tcataacacc      15180
gctgctccag tgcaggagac gctgcacggg tgtcagcctg tcacacagga ggatggtaaa    15240
gagagtcgca tctcagtgca ggagcggcag gtgacagaca gcatagcctt gaggcccctg    15300
gtctgaaccc tggaactgct ttggaggcga tggctcggct cgggagcagg ggcctggctc    15360
tgaggactgc ttgctgacct ttgaagtttg agatgagcca agacagagcc cagtgcagct    15420
aactctcatg cctgccccct atcatttctc aacttgcttt ttaaggatgg agggagagct    15480
cgggcatcgg gggtccacag tgataccctac caagtgcagc agtgcaggac ccagagtcgt    15540
cttgctgcgg cgttcactgt aaggagtcat ggacacagga gtccgtggcc cacagcttgt    15600
gctgctagag ggcacctggt tgcccatcag cagggtactg gctaaataaa tctgtaatta    15660
tttatacaat gacatctcag aaactctagc aggtggggca gaaaacaggt agtagaatga    15720
tgggtagaga aatagcttt aaaacacatt ccaaggcagg taagatggct tttgtgagta      15780
aaggagcttg ctgcccaaac ccggttacct gattttgatc cctgggactt catggtaaaa    15840
gggagagaac caaatccaga gggttgtcat ttgacctcca tgtgtgctct gtggtaatgt    15900
accccgtgtg tgcacatgtg cacatatcct aaaatggatg tggtggtgta ttgtagaaat    15960
tatttaatcc cgccctgggg tttctacctg tgtgttacca tttagttctt gaataaaaga    16020
cacactcaac ctttatattt acaataa                                         16047
```

<210> SEQ ID NO 9  
<211> LENGTH: 23  
<212> TYPE: DNA  
<213> ORGANISM: Artificial Sequence  
<220> FEATURE:  
<223> OTHER INFORMATION: single guide RNA (sgRNA) for Exon 1 of AIRE

<400> SEQUENCE: 9
gcaccgcacc gagatcgcgg tgg                                              23

<210> SEQ ID NO 10  
<211> LENGTH: 23  
<212> TYPE: DNA  
<213> ORGANISM: Artificial Sequence  
<220> FEATURE:  
<223> OTHER INFORMATION: single guide RNA (sgRNA) for Exon 3 of AIRE

<400> SEQUENCE: 10
acctaaacca gtcccggaaa ggg                                              23

<210> SEQ ID NO 11  
<211> LENGTH: 15  
<212> TYPE: PRT  
<213> ORGANISM: Artificial Seqeunce  
<220> FEATURE:  
<223> OTHER INFORMATION: Peptide tag

```
<400> SEQUENCE: 11

Gly Leu Asn Asp Ile Phe Glu Ala Gln Lys Ile Glu Trp His Glu
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: Peptide tag

<400> SEQUENCE: 12

His His His His His His
1               5

<210> SEQ ID NO 13
<211> LENGTH: 198
<212> TYPE: PRT
<213> ORGANISM: Homo sapiens

<400> SEQUENCE: 13

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Pro Arg Gln Leu
                165                 170                 175

Arg Arg Ile Leu Leu Pro Leu Tyr Glu Val Asp Asp Leu Arg Asp Ala
                180                 185                 190

Phe Arg Thr Trp Gly Arg
            195
```